(12) United States Patent
Herron et al.

(10) Patent No.: US 9,711,731 B2
(45) Date of Patent: Jul. 18, 2017

(54) BLUE LUMINESCENT COMPOUNDS

(71) Applicant: E. I. DU PONT DE NEMOURS AND COMPANY, Wilmington, DE (US)

(72) Inventors: Norman Herron, Newark, DE (US); Weishi Wu, Landenberg, PA (US); Weiying Gao, Landenberg, PA (US); Kalindi Dogra, Wilmington, DE (US); Samuel R. Diamond, Wilmington, DE (US); Juergen Weber, Lincoln University, PA (US); Mark A. Guidry, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 15/030,920

(22) PCT Filed: Oct. 20, 2014

(86) PCT No.: PCT/US2014/061311
§ 371 (c)(1),
(2) Date: Apr. 21, 2016

(87) PCT Pub. No.: WO2015/061198
PCT Pub. Date: Apr. 30, 2015

(65) Prior Publication Data
US 2016/0254450 A1    Sep. 1, 2016

Related U.S. Application Data

(60) Provisional application No. 61/895,709, filed on Oct. 25, 2013.

(51) Int. Cl.
*H01L 51/00* (2006.01)
*C09K 11/06* (2006.01)
(Continued)

(52) U.S. Cl.
CPC ........ *H01L 51/006* (2013.01); *C07C 211/61* (2013.01); *C07D 207/325* (2013.01);
(Continued)

(58) Field of Classification Search
None
See application file for complete search history.

(56) References Cited

U.S. PATENT DOCUMENTS 8,465,848 B2   6/2013  Smith
2008/0160348 A1  7/2008  Smith

FOREIGN PATENT DOCUMENTS

JP   2008214271 A    9/2008
JP   2011037838 A *  2/2011   ............... C07F 7/10
(Continued)

OTHER PUBLICATIONS

International Search Report. International Application No. PCT/US2014/061311. International Filing Date: Oct. 20, 2014. Publication No. WO2015061198. Mail Date: Jan. 19, 2015.
English Abstract of JP2008214271. Application No. JP20070053980 Title: Novel BENZO[C]FLUORENE Derivative and Its Application. Applicant: Tosoh Corp. Publication Date: Sep. 18, 2008.
English Abstract of KR20110005917. Application No. KR20110000006. Title: Omni-Directional Dual Polarization Antenna With Conical Beam Pattern. Applicant: Lee Eun Hyung, Feb. 1, 2017.

*Primary Examiner* — Kristin Vajda

(57) ABSTRACT

There is provided a compound having Formula I:

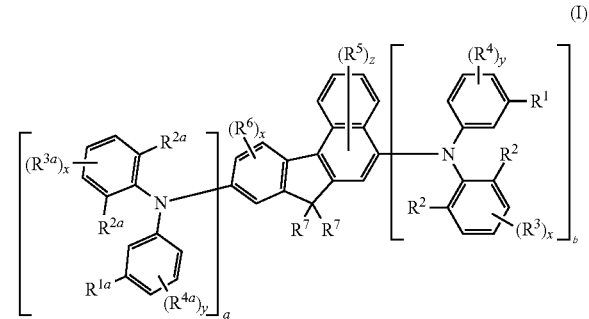

In the formula: $R^1$, $R^{1a}$, $R^2$, and $R^{2a}$ are the same or different and are H, D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, or deuterosiloxy, with the proviso that at least one of $R^1$ and $R^{1a}$ is heteroaryl or deuterated heteroaryl; $R^3$, $R^{3a}$, $R^4$, $R^{4a}$, $R^5$, and $R^6$ are the same or different at each occurrence and are D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, or deuterosiloxy, where adjacent groups selected from $R^3$, $R^{3a}$, $R^4$, and $R^{4a}$ can be joined together to form a fused ring; $R^7$ is the same or different at each occurrence and is alkyl, aryl, or deuterated analogs thereof, where two alkyl $R^7$ groups can be joined together to make a cycloalkyl spiro ring, and where two $R^7$ phenyl groups can be joined to form a spiro fluorene group; a and b are the same or different and are 0 or 1, with the proviso that a+b≥1; x is an integer of 0-3; y is an integer of 0-4; and z is an integer of 0-5.

21 Claims, 2 Drawing Sheets

(51) Int. Cl.
  *C07D 209/86* (2006.01)
  *C07D 405/14* (2006.01)
  *C07D 333/20* (2006.01)
  *C07D 333/76* (2006.01)
  *C07D 235/20* (2006.01)
  *C07C 211/61* (2006.01)
  *C07D 263/32* (2006.01)
  *C07D 207/325* (2006.01)
  *C07D 519/00* (2006.01)
  *C07D 307/52* (2006.01)
  *C07D 307/91* (2006.01)
  *H01L 51/50* (2006.01)

(52) U.S. Cl.
  CPC ......... *C07D 209/86* (2013.01); *C07D 235/20* (2013.01); *C07D 263/32* (2013.01); *C07D 307/52* (2013.01); *C07D 307/91* (2013.01); *C07D 333/20* (2013.01); *C07D 333/76* (2013.01); *C07D 405/14* (2013.01); *C07D 519/00* (2013.01); *C09K 11/06* (2013.01); *H01L 51/0052* (2013.01); *H01L 51/0054* (2013.01); *H01L 51/0061* (2013.01); *H01L 51/0072* (2013.01); *C07C 2103/40* (2013.01); *C09K 2211/1007* (2013.01); *C09K 2211/1011* (2013.01); *C09K 2211/1014* (2013.01); *C09K 2211/1022* (2013.01); *C09K 2211/1029* (2013.01); *H01L 51/0058* (2013.01); *H01L 51/5012* (2013.01)

(56) References Cited

FOREIGN PATENT DOCUMENTS

KR  WO 2010062107 A1 *  6/2010  ......... H01L 51/0058
KR  1020110000006           1/2011

\* cited by examiner

BLUE LUMINESCENT COMPOUNDS

RELATED APPLICATION DATA

This application claims the benefit under 35 U.S.C. §119 (e) of U.S. Provisional Application No. 61/895,709, filed Oct. 25, 2013, which is incorporated by reference herein in its entirety.

BACKGROUND INFORMATION

Field of the Disclosure

This disclosure relates in general to blue luminescent compounds and their use in electronic devices.

Description of the Related Art

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules, such as anthracene, thiadiazole derivatives, and coumarin derivatives are known to show electroluminescence. Metal complexes, particularly iridium and platinum complexes are also known to show electroluminescence. In some cases these small molecule compounds are present as a dopant in a host material to improve processing and/or electronic properties.

There is a continuing need for new luminescent compounds.

SUMMARY

There is provided a compound having Formula I, as described below in the detailed description.

There is also provided a compound having Formula I-a, as described below in the detailed description.

There is also provided a compound having Formula I-b, as described below in the detailed description.

There is also provided a compound having Formula I-c, as described below in the detailed description.

There is also provided a compound having Formula I-d, as described below in the detailed description.

There is also provided a compound having Formula II, as described below in the detailed description.

There is also provided a compound having Formula II-a, as described below in the detailed description.

There is also provided a compound having Formula II-b, as described below in the detailed description.

There is also provided a compound having Formula II-c, as described below in the detailed description.

There is also provided a compound having Formula III, as described below in the detailed description.

There is also provided a compound having Formula III-a, as described below in the detailed description.

There is also provided a compound having Formula III-b, as described below in the detailed description.

There is also provided a compound having Formula III-c, as described below in the detailed description.

There is also provided a compound having Formula III-d, as described below in the detailed description.

There is also provided a compound having Formula III-e, as described below in the detailed description.

There is also provided an organic electronic device comprising a first electrical contact, a second electrical contact and a photoactive layer therebetween, the photoactive layer comprising a compound having Formula I, Formula I-a, Formula I-b, Formula I-c, Formula I-d, Formula II, Formula II-a, Formula II-b, Formula II-c, Formula III, Formula III-a, Formula III-b, Formula III-c, Formula III-d, or Formula III-e.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
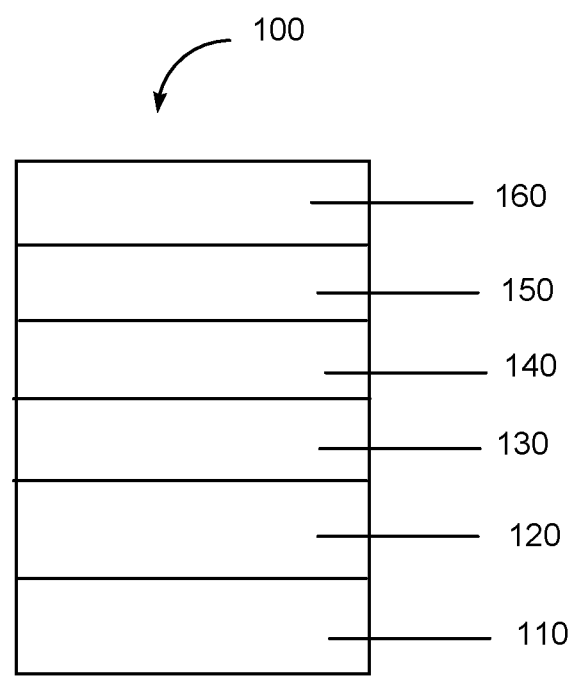
FIG. 1 includes an illustration of an organic light-emitting device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Compound Having Formula I, Formula I-a, Formula I-b, Formula I-c, or Formula I-d, the Compound Having Formula II, Formula II-a, Formula II-b, or Formula II-c, the Compound Having Formula III, Formula III-a, Formula III-b, Formula III-c, Formula III-d, or Formula III-e, Devices, and finally Examples.

1. Definitions and Clarification of Terms

Before addressing details of embodiments described below, some terms are defined or clarified.

The term "adjacent" as it refers to substituent groups refers to groups that are bonded to carbons that are joined together with a single or multiple bond. Exemplary adjacent R groups are shown below:

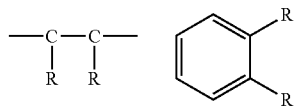

The term "alkoxy" is intended to mean the group RO—, where R is an alkyl group.

The term "alkyl" is intended to mean a group derived from an aliphatic hydrocarbon and includes a linear, a branched, or a cyclic group. In some embodiments, an alkyl has from 1-20 carbon atoms.

The term "aromatic compound" is intended to mean an organic compound comprising at least one unsaturated cyclic group having delocalized pi electrons.

The term "aryl" is intended to mean a group derived from an aromatic hydrocarbon having one point of attachment. The term includes groups which have a single ring and those which have multiple rings which can be joined by a single bond or fused together. Exemplary aryl groups include, but are not limited to phenyl, naphthyl, anthracenyl, phenanthrenyl, and combinations of two or more such groups linked together covalently. The term "alkylaryl" is intended to mean an aryl group having one or more alkyl substituents.

The term "aryloxy" is intended to mean the group RO—, where R is an aryl group.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport materials facilitate negative charge. Although light-emitting materials may also have some charge transport properties, the term "charge transport layer, material, member, or structure" is not intended to include a layer, material, member, or structure whose primary function is light emission.

The term "deuterated" is intended to mean that at least one hydrogen ("H") has been replaced by deuterium ("D"). The term "deuterated analog" refers to a structural analog of a compound or group in which one or more available hydrogens have been replaced with deuterium. In a deuterated compound or deuterated analog, the deuterium is present in at least 100 times the natural abundance level. The term "% deuterated" or "% deuteration" is intended to mean the ratio of deuterons to the sum of protons plus deuterons, expressed as a percentage.

The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material.

The prefix "hetero" indicates that one or more carbon atoms have been replaced with a different atom. In some embodiments, the different atom is N, O, or S.

The term "host material" is intended to mean a material, usually in the form of a layer, to which a dopant may be added. The host material may or may not have electronic characteristic(s) or the ability to emit, receive, or filter radiation.

The terms "luminescent material", "emissive material" and "emitter" are intended to mean a material that emits light when activated by an applied voltage (such as in a light-emitting diode or light-emitting electrochemical cell). The term "blue luminescent material" is intended to mean a material capable of emitting radiation that has an emission maximum at a wavelength in a range of approximately 445-490 nm.

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating or printing. Discontinuous deposition techniques include, but are not limited to, ink jet printing, gravure printing, and screen printing.

The term "organic electronic device" or sometimes just "electronic device" is intended to mean a device including one or more organic semiconductor layers or materials.

The term "photoactive" refers to a material or layer that emits light when activated by an applied voltage (such as in a light emitting diode or chemical cell) or responds to radiant energy and generates a signal with or without an applied bias voltage (such as in a photodetector or a photovoltaic cell).

The term "siloxane" refers to the group $R_3SiOR_2Si$—, where R is the same or different at each occurrence and is H, D, C1-20 alkyl, deuterated alkyl, fluoroalkyl, aryl, or deuterated aryl. In some embodiments, one or more carbons in an R alkyl group are replaced with Si.

The term "siloxy" refers to the group $R_3SiO$—, where R is the same or different at each occurrence and is H, D, C1-20 alkyl, deuterated alkyl, fluoroalkyl, aryl, or deuterated aryl.

The term "silyl" refers to the group $R_3Si$—, where R is the same or different at each occurrence and is H, D, C1-20 alkyl, deuterated alkyl, fluoroalkyl, aryl, or deuterated aryl. In some embodiments, one or more carbons in an R alkyl group are replaced with Si.

All groups may be unsubstituted or substituted. The substituent groups are discussed below. In a structure where a substituent bond passes through one or more rings as shown below,

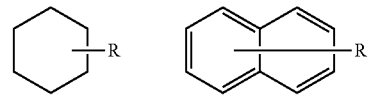

it is meant that the substituent R may be bonded at any available position on the one or more rings.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the disclosed subject matter hereof, is described as consisting essentially of certain features or elements, in which embodiment features or elements that would materially alter the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present.

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation"

convention as seen in the *CRC Handbook of Chemistry and Physics,* 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic cell, and semiconductive member arts.

2. Compounds Having Formula I, Formula I-a, Formula I-b, Formula I-c, or Formula I-d The compounds having Formula I, Formula I-a, Formula I-b, Formula I-c, or Formula I-d have the core benzofluorene structure shown below, where the numbers indicate the positions on the core.

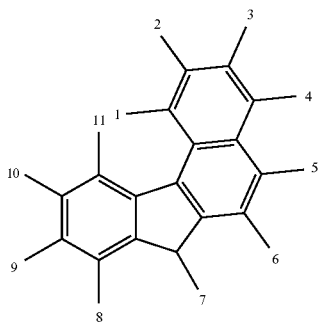

refers to a c.i.e. y-coordinate of less than 0.10, according to the C.I.E. chromaticity scale (Commission Internationale de L'Eclairage, 1931). In some embodiments, the compounds having Formula I, Formula I-a, Formula I-b, Formula I-c, or Formula I-d have a photoluminescence y-coordinate of less than 0.10; in some embodiments, less than 0.090.

In some embodiments, devices including the compounds of Formula I, Formula I-a, Formula I-b, Formula I-c, or Formula I-d have improved efficiencies. In some embodiments, the efficiency of a device including Formula I is greater than 4.5 cd/A at 1000 nits; in some embodiments, greater than 5.0 cd/A at 1000 nits.

In some embodiments, devices including the compounds of Formula I, Formula I-a, Formula I-b, Formula I-c, or Formula I-d have increased lifetime. In some embodiments, devices including the compounds of Formula I have a T70 greater than 1000 hours at 50° C. As used herein, T70 refers to the time to reach 70% of initial luminance. In some embodiments, devices including the compounds of Formula I have a T70 greater than 1500 hours at 50° C.

In some embodiments, electroluminescent devices including the compounds of Formula I, Formula I-a, Formula I-b, Formula I-c, or Formula I-d as emissive materials have deep blue color. In some embodiments, the x-coordinate is less than 0.15 and the y-coordinate is less than 0.10; in some embodiments, the y-coordinate is less than 0.090.

In some embodiments, the compounds have Formula I:

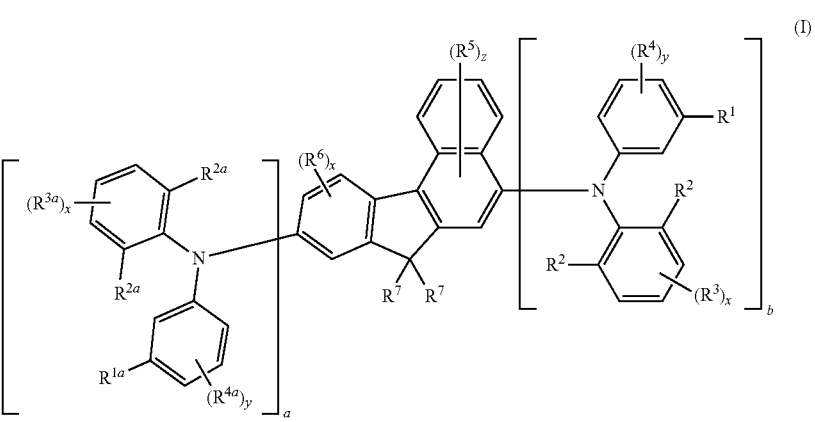

In some embodiments, the compounds having Formula I, Formula I-a, Formula I-b, Formula I-c, or Formula I-d are useful as emissive materials. In some embodiments, the compounds are blue emissive materials. They can be used alone or as a dopant in a host material.

In some embodiments, the compounds having Formula I, Formula I-a, Formula I-b, Formula I-c, or Formula I-d have deep blue color. As used herein, the term "deep blue color"

wherein:
$R^1$, $R^{1a}$, $R^2$, and $R^{2a}$ are the same or different at each occurrence and are selected from the group consisting of H, D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, with the proviso that at least one of $R^1$ and $R^{1a}$ is heteroaryl or deuterated heteroaryl;

$R^3$, $R^{3a}$, $R^4$, $R^{4a}$, $R^5$, and $R^6$ are the same or different at each occurrence and are selected from the group consisting of D, F, CN, alkyl, fluoroalkyl, aryl, heteroaryl, silyl, deuterated alkyl, deuterated partially-fluorinated alkyl, deuterated aryl, deuterated heteroaryl deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, wherein adjacent groups selected from $R^3$, $R^{3a}$, $R^4$, and $R^{4a}$ can be joined together to form a fused ring;

$R^7$ is the same or different at each occurrence and is selected from the group consisting of alkyl, aryl, and deuterated analogs thereof, where two alkyl $R^7$ groups can be joined together to make a cycloalkyl spiro ring, and where two $R^7$ phenyl groups can be joined to form a spiro fluorene group;

a and b are the same or different and are 0 or 1, with the proviso that a+b≥1;

x is an integer of 0-3;

y is an integer of 0-4; and z is an integer of 0-5.

In some embodiments of Formula I, the compound is deuterated. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula I, deuteration is present on the core benzofluorene group.

In some embodiments of Formula I, deuteration is present on one or more substituent groups.

In some embodiments of Formula I, deuteration is present on the core benzofluorene group and one or more substituent groups.

In Formula I, there is at least one of $R^1$ and $R^{1a}$ is heteroaryl or deuterated heteroaryl, so that there is at least one heteroaryl or deuterated heteroaryl group present in the compound. When a=0, $R^1$ is heteroaryl or deuterated heteroaryl. When b=0, $R^{1a}$ is heteroaryl or deuterated heteroaryl.

In some embodiments of Formula I, both $R^1$ and $R^{1a}$ are heteroaryl or deuterated heteroaryl.

In some embodiments of Formula I, at least one of $R^1$ and $R^{1a}$ is a heteroaryl having at least one ring atom which is selected from the group consisting of N, O, and S.

In some embodiments, at least one of $R^1$ and $R^{1a}$ is an N-heteroaryl or deuterated N-heteroaryl having at least one ring atom which is N.

In some embodiments, the N-heteroaryl is selected from the group consisting of pyrrole, pyridine, pyrimidine, carbazole, imidazole, benzimidazole, imidazolobenzimidazole, triazole, benzotriazole, triazolopyridine, indolocarbazole, phenanthroline, quinoline, isoquinoline, quinoxaline, substituted derivatives thereof, and deuterated analogs thereof.

In some embodiments, the N-heteroaryl is a carbazole or deuterated carbazole.

In some embodiments, the N-heteroaryl is a carbazole or deuterated carbazole having formula Cz-1:

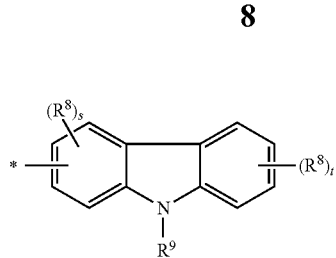

wherein:

$R^8$ is the same or different at each occurrence and is selected from the group consisting of D, alkyl, silyl, aryl, deuterated alkyl, deuterated silyl, and deuterated aryl;

$R^9$ is selected from the group consisting of aryl and deuterated aryl;

s is an integer of 0-3;

t is an integer of 0-4; and

* represents the point of attachment.

In some embodiments, the N-heteroaryl is a carbazole or deuterated carbazole having formula Cz-2:

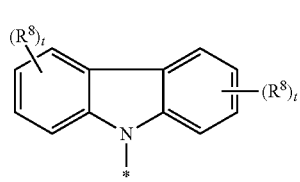

where $R^8$, $R^9$, t, and * are as defined above for Cz-1.

In some embodiments, the N-heteroaryl is a carbazole or deuterated carbazole having formula Cz-3:

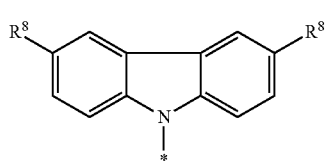

where $R^8$ and * are as defined above for Cz-1.

In some embodiments, the N-heteroaryl is a carbazole or deuterated carbazole having formula Cz-4:

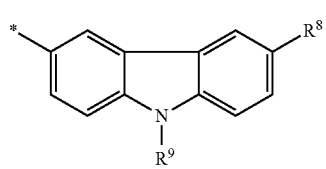

where $R^8$, $R^9$, and * are as defined above for Cz-1.

In some embodiments, the N-heteroaryl is a carbazole or deuterated carbazole having formula Cz-5:

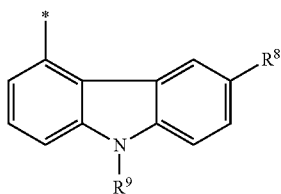
Cz-5 where $R^8$, $R^9$, and * are as defined above for Cz-1.

In some embodiments of Formula I, at least one of $R^1$ and $R^{1a}$ is an S-heteroaryl having at least one ring atom which is S.

In some embodiments, the S-heteroaryl is selected form the group consisting of thiophene, benzothiophene, dibenzothiophene, and deuterated analogs thereof.

In some embodiments, the S-heteroaryl is a dibenzothiophene or deuterated dibenzothiophene.

In some embodiments, the S-heteroaryl is a dibenzothiophene or deuterated dibenzothiophene having formula DBT-1

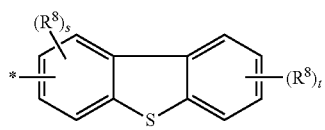
DBT-1 where $R^8$, $R^9$ and * are as defined above for Cz-1.

In some embodiments, the S-heteroaryl is a dibenzothiophene or deuterated dibenzothiophene having formula DBT-2

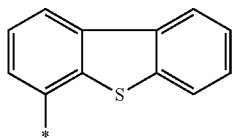
DBT-2 wherein * represents the point of attachment.

In some embodiments, the S-heteroaryl is a dibenzothiophene or deuterated dibenzothiophene having formula DBT-3:

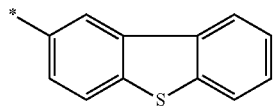
DBT-3 wherein * represents the point of attachment.

In some embodiments of Formula I, at least one of $R^1$ and $R^{1a}$ is an O-heteroaryl having at least one ring atom that is O.

In some embodiments, the O-heteroaryl is selected from the group consisting of furan, benzofuran, dibenzofuran, and deuterated analogs thereof.

In some embodiments, the O-heteroaryl is a dibenzofuran or deuterated dibenzofuran.

In some embodiments, the O-heteroaryl is a dibenzofuran or deuterated dibenzofuran having formula DBF-1:

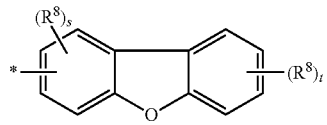
DBF-1 where $R^8$, $R^9$ and * are as defined above for Cz-1.

In some embodiments, the O-heteroaryl is a dibenzofuran or deuterated dibenzofuran having formula DBF-2

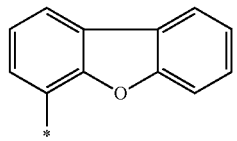
DBF-2 wherein * represents the point of attachment.

In some embodiments, the O-heteroaryl is a dibenzofuran or deuterated dibenzofuran having formula DBF-3:

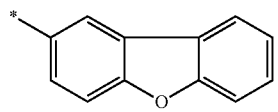
DBF-3 wherein * represents the point of attachment.

In some embodiments of Formula I, at least one of $R^1$ and $R^{1a}$ is an N,O-heteroaryl having at least one ring atom that is N and at least one ring atom that is O.

In some embodiments, the N,O-heteroaryl is selected from the group consisting of oxazole, benzoxazole, and deuterated analogs thereof.

In some embodiments, the N,O-heteroaryl is a benzoxazole or deuterated benzoxazole having formula BzO-1:

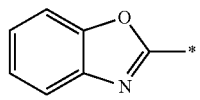
BzO-1 wherein * represents the point of attachment.

In some embodiments of Formula I, at least one of $R^1$ and $R^{1a}$ is an N,S-heteroaryl having at least one ring atom that is N and at least one ring atom that is S.

In some embodiments, the N,S-heteroaryl is selected from the group consisting of thiazole, benzothiazole, and deuterated analogs thereof.

In some embodiments, the N,S-heteroaryl is a benzothiazole or deuterated benzothiazole having formula BT-1:

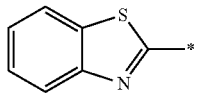

BT-1

In some embodiments of Formula I, $R^1$ and $R^{1a}$ are the same.

In some embodiments of Formula I, $R^2$ and $R^{2a}$ are H or D at each occurrence.

In some embodiments of Formula I, at least one $R^2$ is selected from alkyl and deuterated alkyl.

In some embodiments of Formula I, at least one $R^{2a}$ is selected from alkyl and deuterated alkyl.

In some embodiments, the alkyl or deuterated alkyl has 1-12 carbons; in some embodiments, 3-8 carbons; in some embodiments, 1-4 carbons.

In some embodiments of Formula I, one $R^2$ and $R^{2a}$ group is alkyl or deuterated alkyl, and the other $R^2$ and $R^{2a}$ group is H or D.

In some embodiments of Formula I, $R^2$ is alkyl or deuterated alkyl at each occurrence.

In some embodiments of Formula I, $R^{2a}$ is alkyl or deuterated alkyl at each occurrence.

In some embodiments of Formula I, at least one $R^2$ is selected from aryl and deuterated aryl.

In some embodiments of Formula I, at least one $R^{2a}$ is selected from aryl and deuterated aryl.

In some embodiments of Formula I, at least one $R^2$ is selected from the group consisting of phenyl, naphthyl, phenyl substituted with one or more alkyl groups, naphthyl substituted with one or more alkyl groups, and deuterated analogs thereof.

In some embodiments of Formula I, at least one $R^{2a}$ is selected from the group consisting of phenyl, naphthyl, phenyl substituted with one or more alkyl groups, naphthyl substituted with one or more alkyl groups, and deuterated analogs thereof.

In some embodiments of Formula I, $R^2$ and $R^{2a}$ are the same.

In Formula I, x can be the same or different at each occurrence.

In some embodiments of Formula I, at least one x is non-zero.

In some embodiments of Formula I, at least one $R^3$ is present and is selected from the group consisting of alkyl and deuterated alkyl having 1-12 carbons; in some embodiments, 3-8 carbons; in some embodiments 1-4 carbons.

In some embodiments of Formula I, at least one $R^{3a}$ is present and is selected from the group consisting of alkyl and deuterated alkyl having 1-12 carbons; in some embodiments, 3-8 carbons; in some embodiments 1-4 carbons.

In some embodiments of Formula I, at least one $R^3$ is present and is selected from the group consisting of phenyl, naphthyl, anthracenyl, combinations of such groups linked together covalently, and deuterated analogs thereof, where the groups may be further substituted with alkyl or deuterated alkyl groups.

In some embodiments of Formula I, at least one $R^{3a}$ is present and is selected from the group consisting of phenyl, naphthyl, anthracenyl, combinations of such groups linked together covalently, and deuterated analogs thereof, where the groups may be further substituted with alkyl or deuterated alkyl groups.

In some embodiments of Formula I, at least one $R^3$ is present and is selected from the group consisting of phenyl, terphenyl, quaterphenyl, naphthyl, and deuterated analogs thereof.

In some embodiments of Formula I, at least one $R^{3a}$ is present and is selected from the group consisting of phenyl, terphenyl, quaterphenyl, naphthyl, and deuterated analogs thereof.

In some embodiments, x with respect to $R^3$ is 0.
In some embodiments, x with respect to $R^3$ is 1 or 2.
In some embodiments, x with respect to $R^3$ is 3.
In some embodiments, x with respect to $R^{3a}$ is 0.
In some embodiments, x with respect to $R^{3a}$ is 1 or 2.
In some embodiments, x with respect to $R^{3a}$ is 3.

In Formula I, y is the same or different at each occurrence.

In some embodiments of Formula I, at least one y is non-zero.

In some embodiments of Formula I, at least one $R^4$ is present and is selected from the group consisting of alkyl and deuterated alkyl having 1-12 carbons; in some embodiments, 3-8 carbons; in some embodiments 1-4 carbons.

In some embodiments of Formula I, at least one $R^{4a}$ is present and is selected from the group consisting of alkyl and deuterated alkyl having 1-12 carbons; in some embodiments, 3-8 carbons; in some embodiments 1-4 carbons.

In some embodiments of Formula I, y with respect to $R^4$ is 0 or 1.

In some embodiments of Formula I, y with respect to $R^4$ is 2.

In some embodiments of Formula I, y with respect to $R^4$ is 3.

In some embodiments of Formula I, y with respect to $R^4$ is 4.

In some embodiments of Formula I, y with respect to $R^{4a}$ is 0 or 1.

In some embodiments of Formula I, y with respect to $R^{4a}$ is 2.

In some embodiments of Formula I, y with respect to $R^{4a}$ is 3.

In some embodiments of Formula I, y with respect to $R^{4a}$ is 4.

In some embodiments of Formula I, one or more of $R^5$ is D.

In some embodiments of Formula I, one of $R^5$ is alkyl or deuterated alkyl.

In some embodiments of Formula I, z=0
In some embodiments of Formula I, z=1.
In some embodiments of Formula I, z=2.
In some embodiments of Formula I, z=3.
In some embodiments of Formula I, z=4.
In some embodiments of Formula I, z=5.
In some embodiments of Formula I, z>2.

In some embodiments of Formula I, one or more of $R^6$ is D.

In some embodiments of Formula I, one of $R^6$ is alkyl or deuterated alkyl.

In some embodiments of Formula I, x with respect to $R^6$ is 0 or 1.

In some embodiments of Formula I, x with respect to $R^6$ is 2.

In some embodiments of Formula I, x with respect to $R^6$ is 3.

In some embodiments of Formula I, $R^7$ is selected from the group consisting of alkyl and deuterated alkyl having 1-12 carbons; in some embodiments, 3-8 carbons; in some embodiments 1-4 carbons.

In some embodiments of Formula I, the two $R^7$ groups are joined together to form a 5- or 6-membered aliphatic ring.

In some embodiments of Formula I, $R^7$ is selected from the group consisting of aryl and deuterated aryl.

In some embodiments of Formula I, $R^7$ is selected from the group consisting of phenyl and deuterated phenyl.

In some embodiments of Formula I, the two $R^7$ groups are phenyl groups which are joined together to form a spirofluorene group.

In some embodiments of Formula I, a=0 and b=1. When a=0 the 9-position is H or $R^6$.

In some embodiments of Formula I, a=1 and b=0. When b=0 the 5-position is H or $R^5$.

In some embodiments of Formula I, a=b=1.

Any of the above embodiments of Formula I can be combined with one or more of the other embodiments, so long as they are not mutually exclusive. For example, the embodiment in which $R^{1a}$ is carbazole or deuterated carbazole can be combined with the embodiment where $R^{2a}$ is an alkyl or deuterated alkyl having 3-8 carbons and the embodiment where b=0. The same is true for the other non-mutually-exclusive embodiments discussed above. The skilled person would understand which embodiments were mutually exclusive and would thus readily be able to determine the combinations of embodiments that are contemplated by the present application.

In some embodiments, the compounds have Formula I-a:

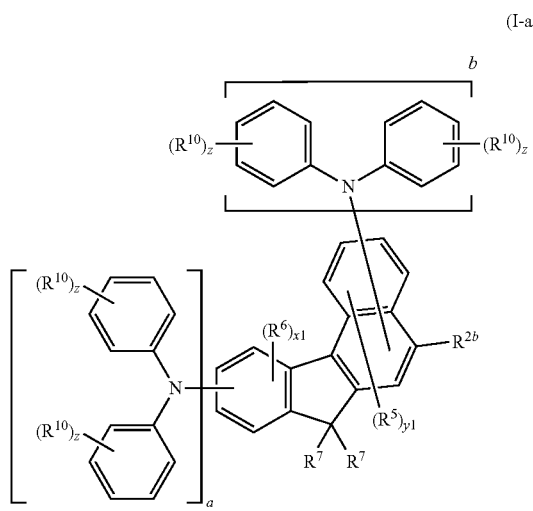

(I-a)

wherein:

$R^{2b}$ is selected from the group consisting of H, D, F, CN, alkyl, fluoroalkyl, aryl, heteroaryl, silyl, deuterated alkyl, deuterated partially fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy;

$R^5$ and $R^6$ are the same or different at each occurrence and are selected from the group consisting of D, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy;

$R^7$ is the same or different at each occurrence and is selected from the group consisting of alkyl, aryl, and deuterated analogs thereof, where two alkyl $R^7$ groups can be joined together to make a cycloalkyl spiro ring, and where two $R^7$ phenyl groups can be joined to form a spiro fluorene group;

$R^{10}$ is the same or different at each occurrence and is selected from the group consisting of D, F, CN, alkyl, fluoroalkyl, aryl, heteroaryl, silyl, deuterated alkyl, deuterated partially fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, where adjacent $R^{10}$ groups can be joined together to form a fused ring;

a and b are the same or different and are 0 or 1, with the proviso that a+b≥1;

x1 is an integer of 0-4, with the proviso that when a=1, x1 is 0-3;

y1 is an integer of 0-5, with the proviso that when b=1, y1 is 0-4; and z is the same or different at each occurrence and is an integer of 0-5.

In some embodiments of Formula I-a, the compound is deuterated. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula I-a, deuteration is present on the core benzofluorene group.

In some embodiments of Formula I-a, deuteration is present on one or more substituent groups.

In some embodiments of Formula I-a, deuteration is present on the core benzofluorene group and one or more substituent groups.

In some embodiments of Formula I-a, a=1 and b=0.
In some embodiments of Formula I-a, a=0 and b=1.
In some embodiments of Formula I-a, a=b=1.
In some embodiments of Formula I-a, a=1 and the amino nitrogen is bonded to position 8 on the benzofluorene core.
In some embodiments of Formula I-a, a=1 and the amino nitrogen is bonded to position 9 on the benzofluorene core.
In some embodiments of Formula I-a, a=1 and the amino nitrogen is bonded to position 10 on the benzofluorene core.
In some embodiments of Formula I-a, a=1 and the amino nitrogen is bonded to position 11 on the benzofluorene core.
In some embodiments of Formula I-a, b=1 and the amino nitrogen is bonded to position 1 on the benzofluorene core.
In some embodiments of Formula I-a, b=1 and the amino nitrogen is bonded to position 2 on the benzofluorene core.
In some embodiments of Formula I-a, b=1 and the amino nitrogen is bonded to position 3 on the benzofluorene core.
In some embodiments of Formula I-a, b=1 and the amino nitrogen is bonded to position 4 on the benzofluorene core.
In some embodiments of Formula I-a, b=1 and the amino nitrogen is bonded to position 6 on the benzofluorene core.
In some embodiments of Formula I-a, $R^{2b}$ is H or D.
In some embodiments of Formula I-a, $R^{2b}$ is selected from the group consisting of alkyl and deuterated alkyl having 1-12 carbons; in some embodiments, 3-8 carbons; in some embodiments 1-4 carbons.

In some embodiments of Formula I-a, y1=0.
In some embodiments of Formula I-a, y1=1.
In some embodiments of Formula I-a, y1=2.
In some embodiments of Formula I-a, y1=3.
In some embodiments of Formula I-a, y1=4.
In some embodiments of Formula I-a, y1=5.
In some embodiments of Formula I-a, y1>1.
In some embodiments of Formula I-a, $R^5$ is as described above for Formula I.
In some embodiments of Formula I-a, x1=0.
In some embodiments of Formula I-a, x1=1.
In some embodiments of Formula I-a, x1=2.
In some embodiments of Formula I-a, x1=3.
In some embodiments of Formula I-a, x1=4.
In some embodiments of Formula I-a, x1>1.
In some embodiments of Formula I-a, $R^6$ is as described above for Formula I.
In some embodiments of Formula I-a, $R^7$ is as described above for Formula I.
In some embodiments of Formula I-a, at least one z is non-zero.
In some embodiments of Formula I-a, at least one z is 0 or 1.
In some embodiments of Formula I-a, at least one z is 2.
In some embodiments of Formula I-a, at least one z is 3.
In some embodiments of Formula I-a, at least one z is 4.
In some embodiments of Formula I-a, at least one z is 5.
In some embodiments of Formula I-a, at least one $R^{10}$ group is present and is selected from the group consisting of aryl, heteroaryl, and deuterated analogs thereof.
In some embodiments of Formula I-a, at least one $R^{10}$ group is present and is selected from the group consisting of heteroaryl and deuterated heteroaryl, where the heteroaryl has at least one ring atom which is selected from the group consisting of N, O, and S.
In some embodiments of Formula I-a, at least one $R^{10}$ group is present and is an N-heteroaryl selected from the group consisting of pyrrole, pyridine, pyrimidine, carbazole, imidazole, benzimidazole, imidazolobenzimidazole, triazole, benzotriazole, triazolopyridine, substituted derivatives thereof, and deuterated analogs thereof.
In some embodiments of Formula I-a, at least one $R^{10}$ group is present and is an S-heteroaryl selected form the group consisting of thiophene, benzothiophene, dibenzothiophene, and deuterated analogs thereof.
In some embodiments of Formula I-a, at least one $R^{10}$ group is present and is an O-heteroaryl selected from the group consisting of furan, benzofuran, dibenzofuran, and deuterated analogs thereof.
In some embodiments of Formula I-a, at least one $R^{10}$ group is present and is an N,O-heteroaryl selected from the group consisting of oxazole, benzoxazole, and deuterated analogs thereof.
In some embodiments of Formula I-a, at least one $R^{10}$ group is present and is an N,S-heteroaryl selected from the group consisting of thiazole, benzothiazole, and deuterated analogs thereof.
In some embodiments of Formula I-a, at least one $R^{10}$ group is present and is selected from the group consisting of Cz-1, Cz-2, Cz-3, DBT-1, DBT-2, DBF-1, DBF-2, BzO-1, BT-1, and deuterated analogs thereof, as those groups are defined above.
In some embodiments of Formula I-a, at least one $R^{10}$ group is present and is selected from the group consisting of phenyl, naphthyl, anthracenyl, combinations of such groups linked together covalently, and deuterated analogs thereof, where the groups may be further substituted with alkyl or deuterated alkyl groups.

In some embodiments of Formula I-a, at least one $R^{10}$ is present and is selected from the group consisting of phenyl, terphenyl, quaterphenyl, naphthyl, and deuterated analogs thereof.

In some embodiments of Formula I-a, at least one $R^{10}$ group is present and is selected from alkyl and deuterated alkyl having 1-12 carbons; in some embodiments, 3-8 carbons; in some embodiments 1-4 carbons.

Any of the above embodiments of Formula I-a can be combined with one or more of the other embodiments, so long as they are not mutually exclusive. For example, the embodiment in which at least one z is non-zero can be combined with the embodiments in which $R^{10}$ is carbazole or deuterated carbazole and with the embodiment where a=b=1. The same is true for the other non-mutually-exclusive embodiments discussed above. The skilled person would understand which embodiments were mutually exclusive and would thus readily be able to determine the combinations of embodiments that are contemplated by the present application.

In some embodiments, the compound has Formula I-b:

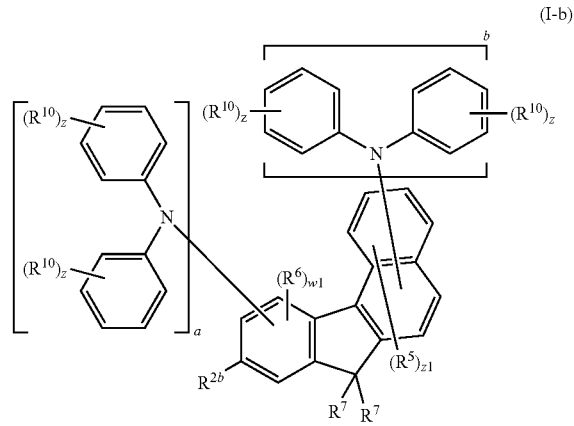

(I-b)

wherein:
$R^{2b}$ is selected from the group consisting of H, D, F, CN, alkyl, fluoroalkyl, aryl, heteroaryl, silyl, deuterated alkyl, deuterated partially-fluorinated alkyl, deuterated aryl, deuterated heteroaryl and deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy;

$R^5$ and $R^6$ are the same or different at each occurrence and are selected from the group consisting of D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy;

$R^7$ is the same or different at each occurrence and is selected from the group consisting of alkyl, aryl, and deuterated analogs thereof, where two alkyl $R^7$ groups can be joined together to make a cycloalkyl spiro ring, and where two $R^7$ phenyl groups can be joined to form a spiro fluorene group;

$R^{10}$ is the same or different at each occurrence and is selected from the group consisting of D, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, where adjacent $R^{10}$ groups can be joined together to form a fused ring;

a and b are the same or different and are 0 or 1, with the proviso that a+b≥1;

w1 is an integer of 0-3, with the proviso that when a=1, w is 0-2;

z is the same or different at each occurrence and is an integer of 0-5; and z1 is an integer of 0-6, with the proviso that when b=1, z is 0-5.

In some embodiments of Formula I-b, the compound is deuterated. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula I-b, deuteration is present on the core benzofluorene group.

In some embodiments of Formula I-b, deuteration is present on one or more substituent groups.

In some embodiments of Formula I-b, deuteration is present on the core benzofluorene group and one or more substituent groups.

In some embodiments of Formula I-b, a=1 and b=0.
In some embodiments of Formula I-b, a=0 and b=1.
In some embodiments of Formula I-b, a=b=1.
In some embodiments of Formula I-b, a=1 and the amino nitrogen is bonded to position 8 on the benzofluorene core.
In some embodiments of Formula I-b, a=1 and the amino nitrogen is bonded to position 10 on the benzofluorene core.
In some embodiments of Formula I-b, a=1 and the amino nitrogen is bonded to position 11 on the benzofluorene core.
In some embodiments of Formula I-b, b=1 and the amino nitrogen is bonded to position 1 on the benzofluorene core.
In some embodiments of Formula I-b, b=1 and the amino nitrogen is bonded to position 2 on the benzofluorene core.
In some embodiments of Formula I-b, b=1 and the amino nitrogen is bonded to position 3 on the benzofluorene core.
In some embodiments of Formula I-b, b=1 and the amino nitrogen is bonded to position 4 on the benzofluorene core.
In some embodiments of Formula I-b, b=1 and the amino nitrogen is bonded to position 5 on the benzofluorene core.
In some embodiments of Formula I-b, b=1 and the amino nitrogen is bonded to position 6 on the benzofluorene core.
In some embodiments of Formula I-b, $R^{2b}$ is as described above for Formula I-a.
In some embodiments of Formula I-a, z1=0.
In some embodiments of Formula I-a, z1=1.
In some embodiments of Formula I-a, z1=2.
In some embodiments of Formula I-a, z1=3.
In some embodiments of Formula I-a, z1=4.
In some embodiments of Formula I-a, z1=5.
In some embodiments of Formula I-a, z1=6.
In some embodiments of Formula I-a, z1>1.
In some embodiments of Formula I-b, $R^5$ is as described above for Formula I.
In some embodiments of Formula I-a, w1=0.
In some embodiments of Formula I-a, w1=1.
In some embodiments of Formula I-a, w1=2.
In some embodiments of Formula I-a, w1=3.
In some embodiments of Formula I-a1, w1>1.

In some embodiments of Formula I-b, $R^6$ is as described above for Formula I.
In some embodiments of Formula I-b, $R^7$ is as described above for Formula I.
In some embodiments of Formula I-b, at least one z is non-zero.
In some embodiments of Formula I-b, z is 0 or 1.
In some embodiments of Formula I-b, at least one z is 2.
In some embodiments of Formula I-b, $R^{10}$ is as described above for Formula I-a.

Any of the above embodiments of Formula I-b can be combined with one or more of the other embodiments, so long as they are not mutually exclusive. For example, the embodiment in which the compound is 50% deuterated can be combined with the embodiment where $R^{10}$ is an O-heteroaryl and the embodiment where w1=0. The same is true for the other non-mutually-exclusive embodiments discussed above. The skilled person would understand which embodiments were mutually exclusive and would thus readily be able to determine the combinations of embodiments that are contemplated by the present application.

In some embodiments, the compound has Formula I-c:

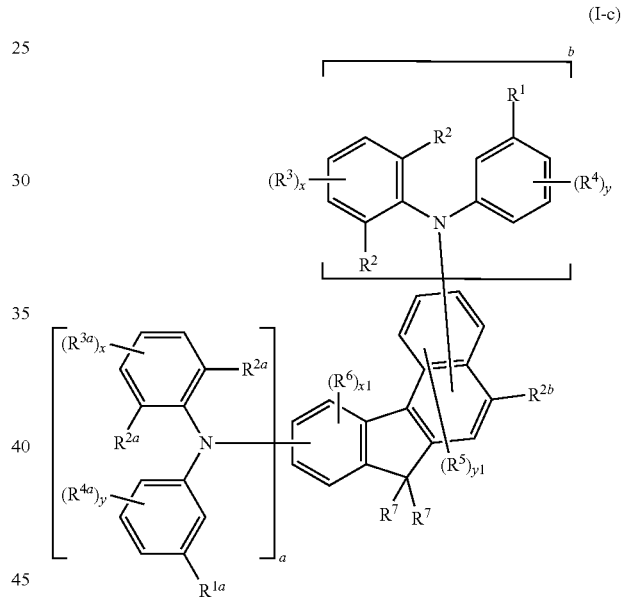

(I-c)

wherein:

$R^1$, $R^{1a}$, $R^2$, $R^{2a}$, and $R^{2b}$ are the same or different at each occurrence and are selected from the group consisting of H, D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, with the proviso that at least one of $R^1$ and $R^{1a}$ is heteroaryl or deuterated heteroaryl;

$R^3$, $R^{3a}$, $R^4$, $R^{4a}$, $R^5$, and $R^6$ are the same or different at each occurrence and are selected from the group consisting of D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, wherein adjacent groups selected from $R^3$, $R^{3a}$, $R^4$, and $R^{4a}$ can be joined together to form a fused ring;

R⁷ is the same or different at each occurrence and is selected from the group consisting of alkyl, aryl, and deuterated analogs thereof, where two alkyl R⁷ groups can be joined together to make a cycloalkyl spiro ring, and where two R⁷ phenyl groups can be joined to form a spiro fluorene group;

a and b are the same or different and are 0 or 1, with the proviso that a+b≥1;

x is the same or different at each occurrence and is an integer of 0-3;

x1 is an integer of 0-4, with the proviso that when a=1, x1 is 0-3;

y is the same or different at each occurrence and is an integer of 0-4; and y1 is an integer of 0-5, with the proviso that when b=1, y1 is 0-4.

In some embodiments of Formula I-c, the compound is deuterated. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula I-c, deuteration is present on the core benzofluorene group.

In some embodiments of Formula I-c, deuteration is present on one or more substituent groups.

In some embodiments of Formula I-c, deuteration is present on the core benzofluorene group and one or more substituent groups.

In some embodiments of Formula I-c, a=1 and b=0.
In some embodiments of Formula I-c, a=0 and b=1.
In some embodiments of Formula I-c, a=b=1.
In some embodiments of Formula I-c, a=1 and the amino nitrogen is bonded to position 8 on the benzofluorene core.
In some embodiments of Formula I-c, a=1 and the amino nitrogen is bonded to position 9 on the benzofluorene core.
In some embodiments of Formula I-c, a=1 and the amino nitrogen is bonded to position 10 on the benzofluorene core.
In some embodiments of Formula I-c, a=1 and the amino nitrogen is bonded to position 11 on the benzofluorene core.
In some embodiments of Formula I-c, b=1 and the amino nitrogen is bonded to position 1 on the benzofluorene core.
In some embodiments of Formula I-c, b=1 and the amino nitrogen is bonded to position 2 on the benzofluorene core.
In some embodiments of Formula I-c, b=1 and the amino nitrogen is bonded to position 3 on the benzofluorene core.
In some embodiments of Formula I-c, b=1 and the amino nitrogen is bonded to position 4 on the benzofluorene core.
In some embodiments of Formula I-c, b=1 and the amino nitrogen is bonded to position 6 on the benzofluorene core.
In some embodiments of Formula I-c, R¹ is as described above for Formula I.
In some embodiments of Formula I-c, R¹ᵃ is as described above for Formula I.
In some embodiments of Formula I-c, R² is as described above for Formula I.
In some embodiments of Formula I-c, R²ᵃ is as described above for Formula I.
In some embodiments of Formula I-c, R²ᵇ is as described above for Formula I-a.
In some embodiments of Formula I-c, x is as described above for Formula I.

In some embodiments of Formula I-c, R³ is as described above for Formula I.
In some embodiments of Formula I-c, R³ᵃ is as described above for Formula I.
In some embodiments of Formula I-c, y is as described above for Formula I.
In some embodiments of Formula I-c, R⁴ is as described above for Formula I.
In some embodiments of Formula I-c, R⁴ᵃ is as described above for Formula I.
In some embodiments of Formula I-c, y1=0.
In some embodiments of Formula I-c, y1=1.
In some embodiments of Formula I-c, y1=2.
In some embodiments of Formula I-c, y1=3.
In some embodiments of Formula I-c, y1=4.
In some embodiments of Formula I-c, y1=5.
In some embodiments of Formula I-c1, y1>1.
In some embodiments of Formula I-c, R⁵ is as described above for Formula I.
In some embodiments of Formula I-c, x1=0.
In some embodiments of Formula I-c, x1=1.
In some embodiments of Formula I-c, x1=2.
In some embodiments of Formula I-c, x1=3.
In some embodiments of Formula I-c, x1=4.
In some embodiments of Formula I-c, x1>1.
In some embodiments of Formula I-c, R⁶ is as described above for Formula I.
In some embodiments of Formula I-c, R⁷ is as described above for Formula I.

Any of the above embodiments of Formula I-c can be combined with one or more of the other embodiments, so long as they are not mutually exclusive. For example, the embodiment in which R¹ is deuterated aryl can be combined with the embodiment where R²ᵇ is an alkyl or deuterated alkyl having 3-8 carbons and the embodiment where a=0. The same is true for the other non-mutually-exclusive embodiments discussed above. The skilled person would understand which embodiments were mutually exclusive and would thus readily be able to determine the combinations of embodiments that are contemplated by the present application.

In some embodiments, the compound has Formula I-d:

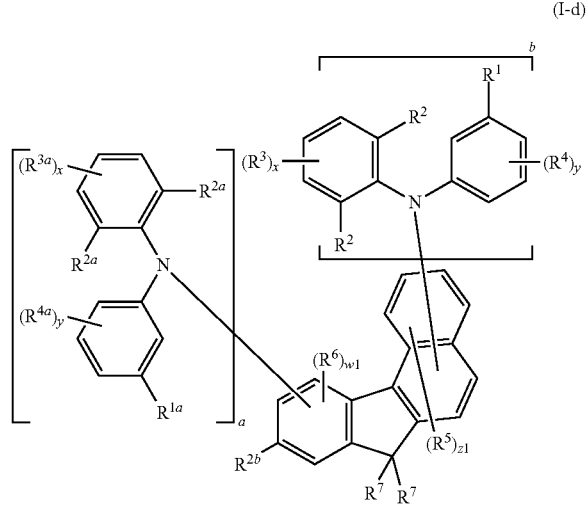

(I-d)

wherein:
- $R^1$, $R^{1a}$, $R^2$, $R^{2a}$, and $R^{2b}$ are the same or different at each occurrence and are selected from the group consisting of H, D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, with the proviso that at least one of $R^1$ and $R^{1a}$ is heteroaryl or deuterated heteroaryl;
- $R^3$, $R^{3a}$, $R^4$, $R^{4a}$, $R^5$, and $R^6$ are the same or different at each occurrence and are selected from the group consisting of D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, wherein adjacent groups selected from $R^3$, $R^{3a}$, $R^4$, and $R^{4a}$ can be joined together to form a fused ring;
- $R^7$ is the same or different at each occurrence and is selected from the group consisting of alkyl, aryl, and deuterated analogs thereof, where two alkyl $R^7$ groups can be joined together to make a cycloalkyl spiro ring, and where two $R^7$ phenyl groups can be joined to form a spiro fluorene group;
- a and b are the same or different and are 0 or 1, with the proviso that $a+b \geq 21$;
- w1 is an integer of 0-3, with the proviso that when a=1, w1 is 0-2;
- x is the same or different at each occurrence and is an integer of 0-3;
- y is the same or different at each occurrence and is an integer of 0-4; and
- z1 is an integer of 0-6, with the proviso that when b=1, z1 is 0-5. In some embodiments of Formula I-d, the compound is deuterated. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula I-d, deuteration is present on the core benzofluorene group.

In some embodiments of Formula I-d, deuteration is present on one or more substituent groups.

In some embodiments of Formula I-d, deuteration is present on the core benzofluorene group and one or more substituent groups.

In some embodiments of Formula I-d, a=1 and b=0.
In some embodiments of Formula I-d, a=0 and b=1.
In some embodiments of Formula I-d, a=b=1.
In some embodiments of Formula I-d, a=1 and the amino nitrogen is bonded to position 8 on the benzofluorene core.
In some embodiments of Formula I-d, a=1 and the amino nitrogen is bonded to position 10 on the benzofluorene core.
In some embodiments of Formula I-d, a=1 and the amino nitrogen is bonded to position 11 on the benzofluorene core.
In some embodiments of Formula I-d, b=1 and the amino nitrogen is bonded to position 1 on the benzofluorene core.
In some embodiments of Formula I-d, b=1 and the amino nitrogen is bonded to position 2 on the benzofluorene core.
In some embodiments of Formula I-d, b=1 and the amino nitrogen is bonded to position 3 on the benzofluorene core.
In some embodiments of Formula I-d, b=1 and the amino nitrogen is bonded to position 4 on the benzofluorene core.
In some embodiments of Formula I-d, b=1 and the amino nitrogen is bonded to position 5 on the benzofluorene core.
In some embodiments of Formula I-d, b=1 and the amino nitrogen is bonded to position 6 on the benzofluorene core.
In some embodiments of Formula I-d, $R^1$ is as described above for Formula I.
In some embodiments of Formula I-d, $R^{1a}$ is as described above for Formula I.
In some embodiments of Formula I-d, $R^2$ is as described above for Formula I.
In some embodiments of Formula I-d, $R^{2a}$ is as described above for Formula I.
In some embodiments of Formula I-d, $R^{2b}$ is as described above for Formula I-a.
In some embodiments of Formula I-d, $R^3$ is as described above for Formula I.
In some embodiments of Formula I-d, $R^{3a}$ is as described above for Formula I.
In some embodiments of Formula I-d, $R^4$ is as described above for Formula I.
In some embodiments of Formula I-d, $R^{4a}$ is as described above for Formula I.
In some embodiments of Formula I-d, $R^5$ is as described above for Formula I.
In some embodiments of Formula I-d, $R^6$ is as described above for Formula I.
In some embodiments of Formula I-d, $R^7$ is as described above for Formula I.
In some embodiments of Formula I-d, x is as described above for Formula I.
In some embodiments of Formula I-d, y is as described above for Formula I.

Any of the above embodiments of Formula I-d can be combined with one or more of the other embodiments, so long as they are not mutually exclusive. For example, the embodiment in which $R^{1a}$ is silyl can be combined with the embodiment where $R^7$ is an alkyl or deuterated alkyl having 3-8 carbons. The same is true for the other non-mutually-exclusive embodiments discussed above. The skilled person would understand which embodiments were mutually exclusive and would thus readily be able to determine the combinations of embodiments that are contemplated by the present application. The compounds of Formula I, Formula I-a, Formula I-b, Formula I-c, and Formula I-d can be made using any technique that will yield a C—C or C—N bond. A variety of such techniques are known, such as Suzuki, Yamamoto, Stille, and Pd- or Ni-catalyzed C—N couplings.

The deuterated analog compounds can be prepared in a similar manner using deuterated precursor materials or, more generally, by treating the non-deuterated compound with deuterated solvent, such as d6-benzene, in the presence of a Lewis acid H/D exchange catalyst, such as aluminum trichloride or ethyl aluminum chloride, or acids such as $CF_3COOD$, DCl, etc. Deuteration reactions have also been described in published PCT application WO2011/053334.

Exemplary preparations are given in the Examples.

Examples of compounds having Formula I include, but are not limited to, the compounds shown below.

Compound 1
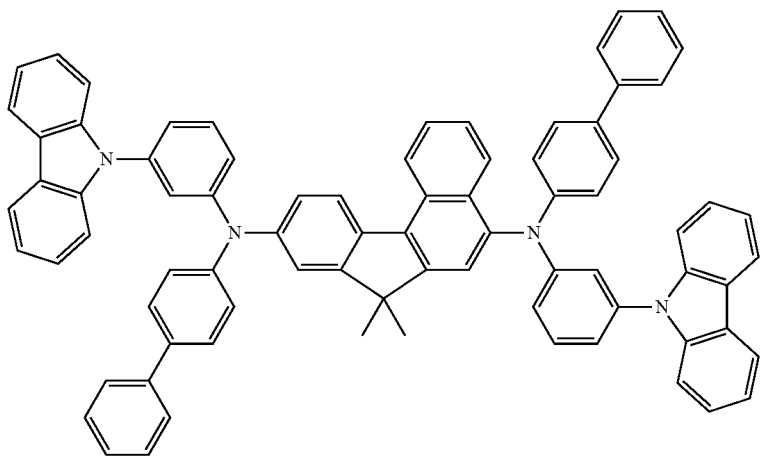
Compound 2
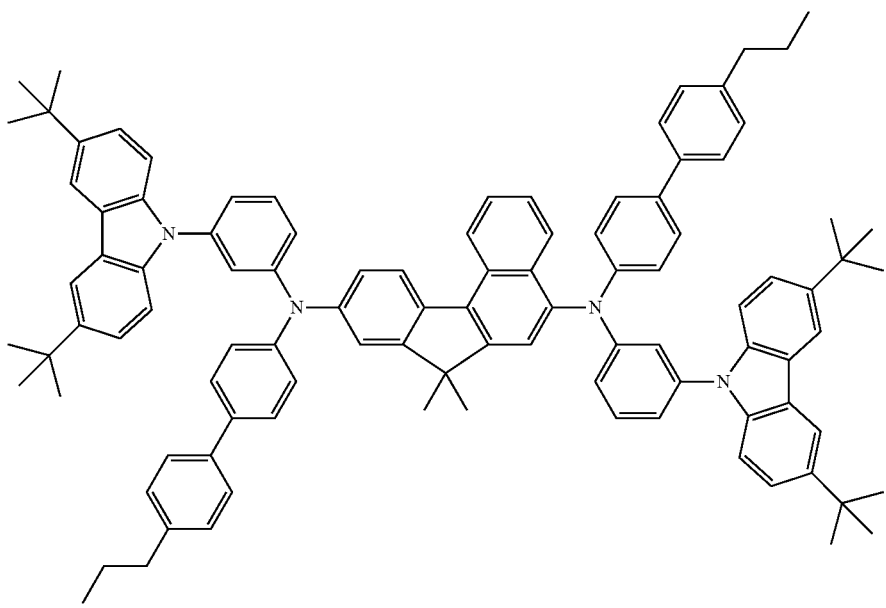
Compound 3
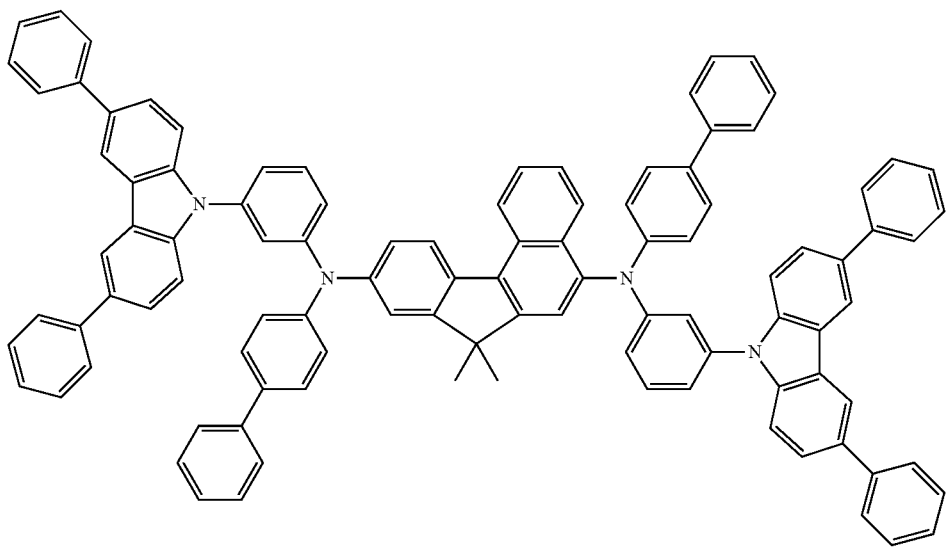

Compound 4
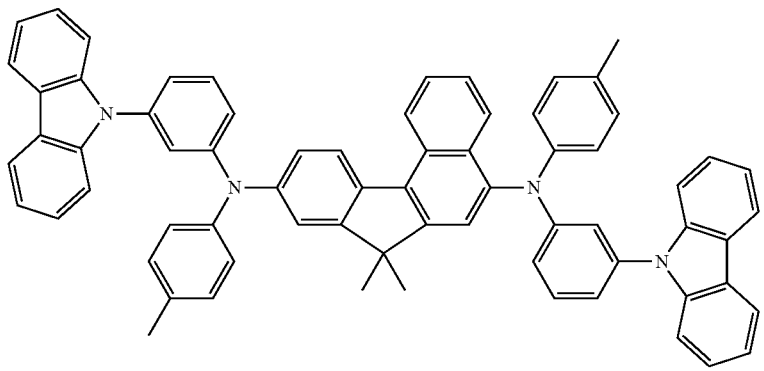
Compound 5
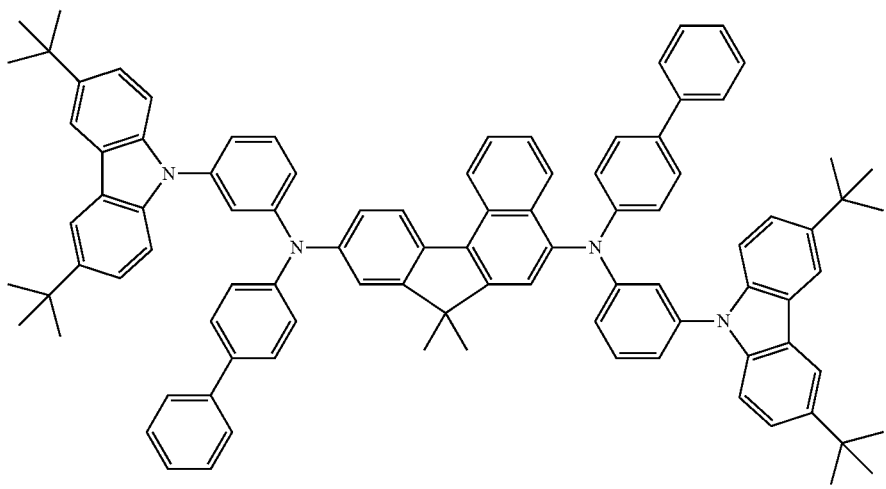
Compound 6
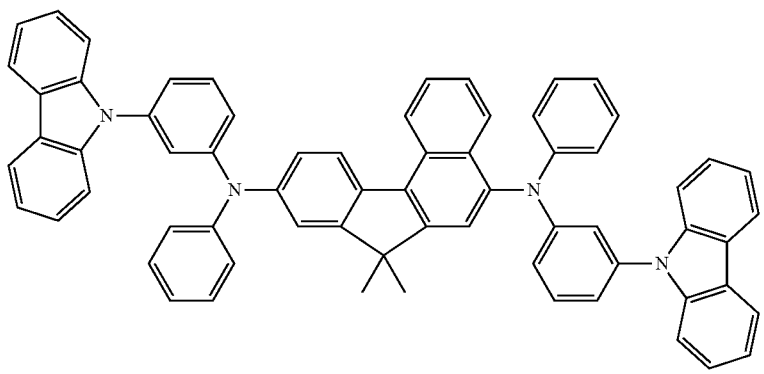

Compound 7
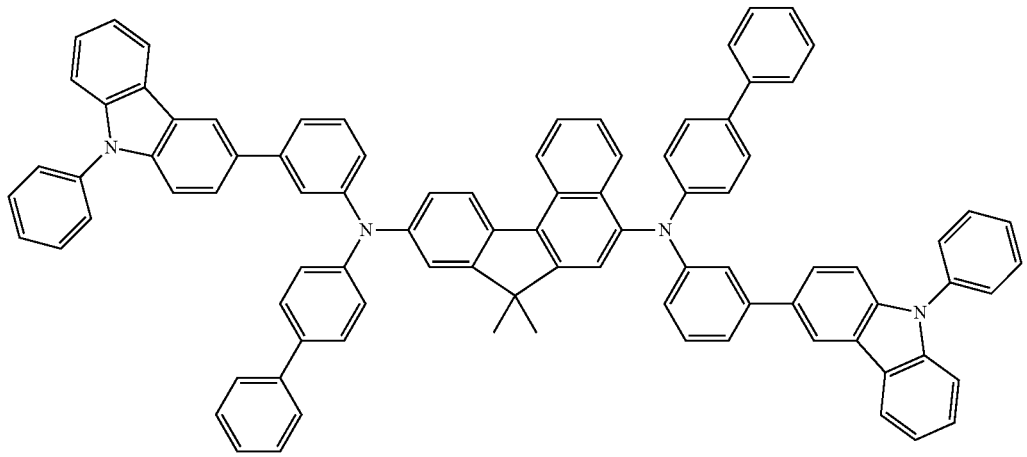
Compound 8
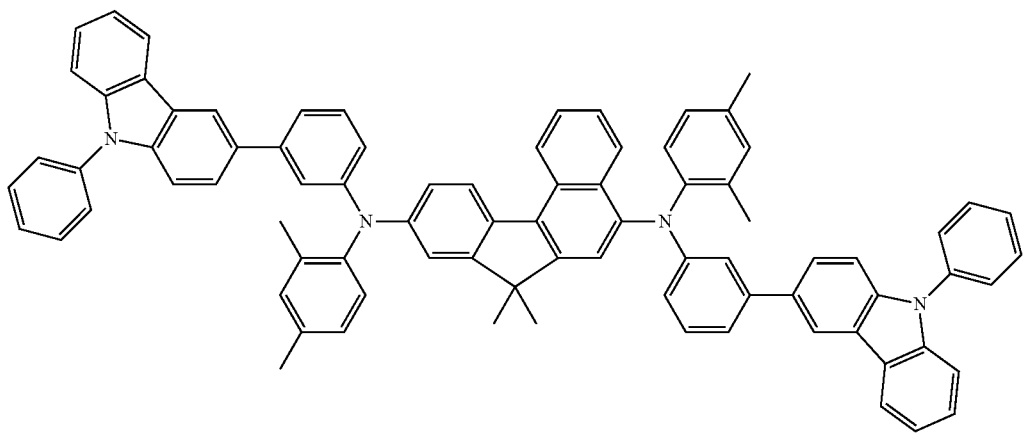
Compound 9
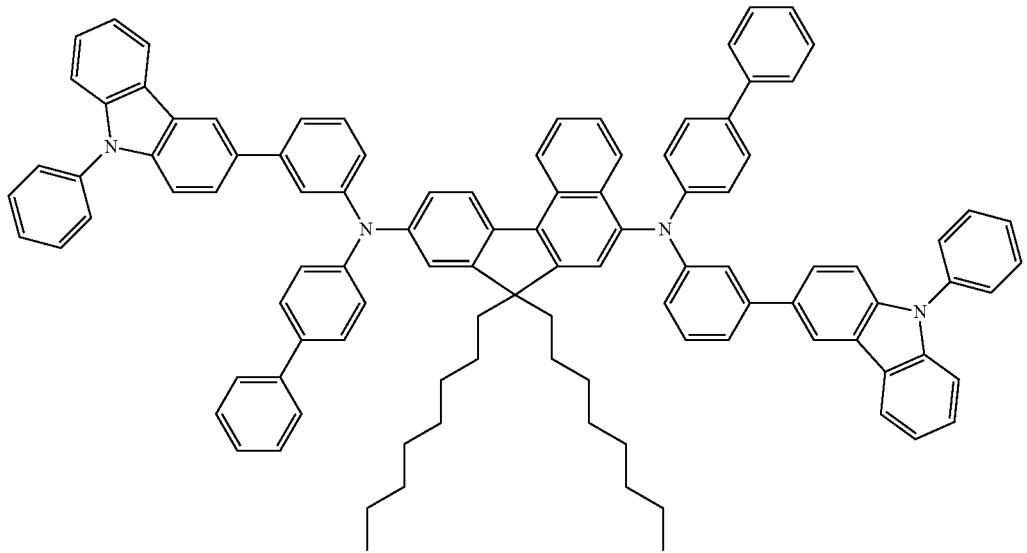

Compound 10
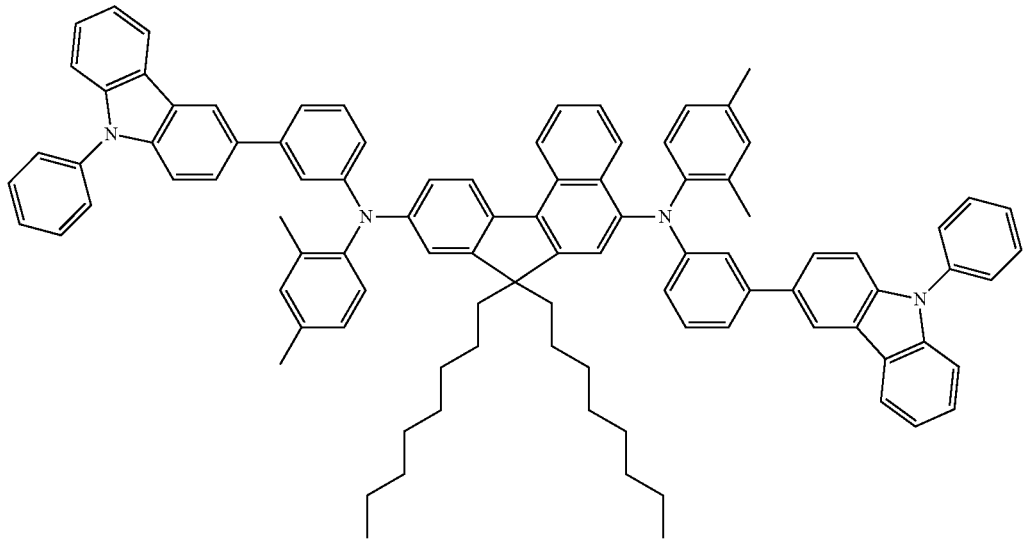
Compound 11
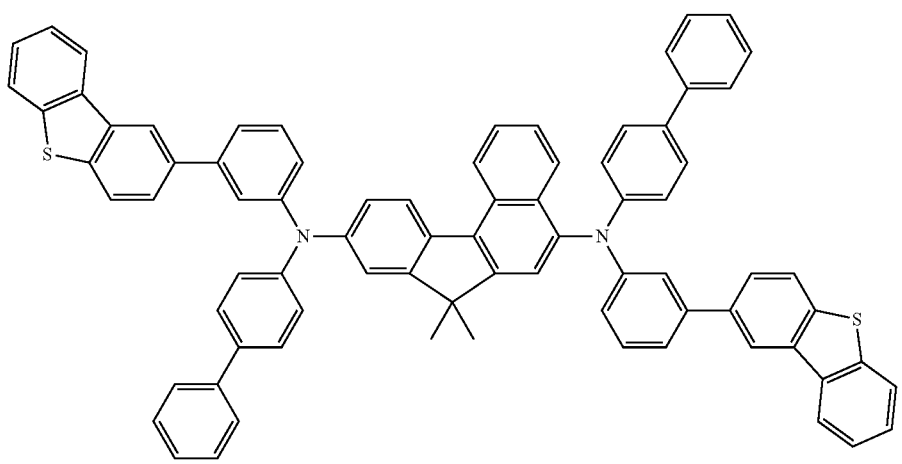
Compound 12
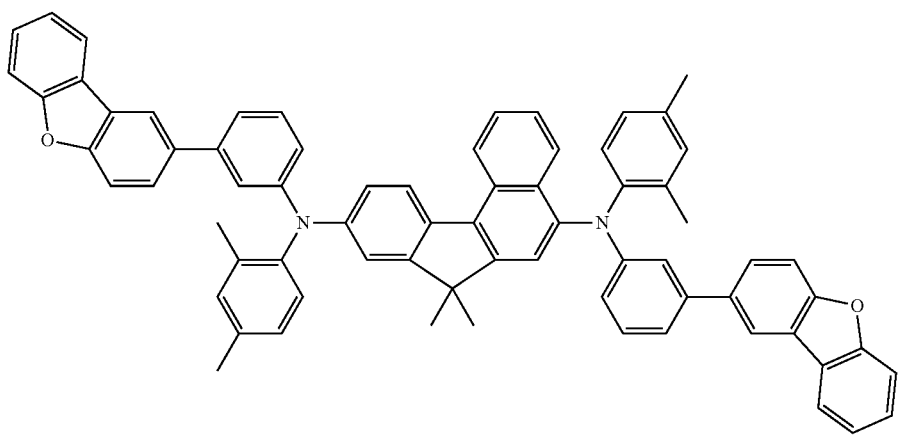

-continued
Compound 13
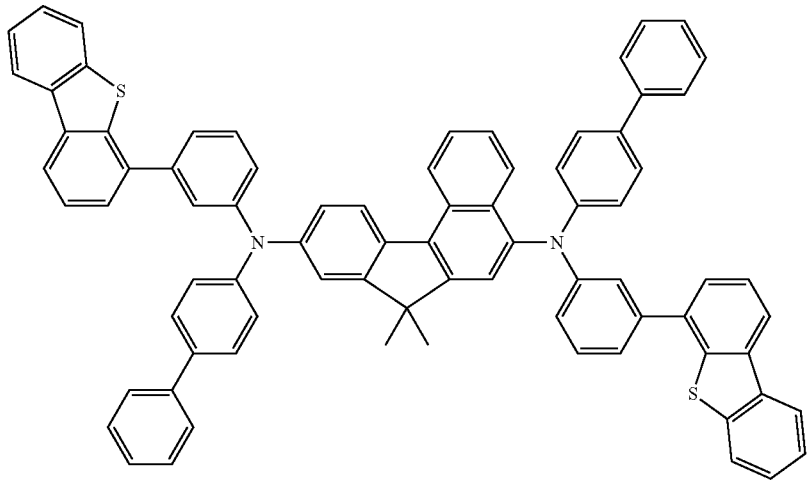
Compound 14
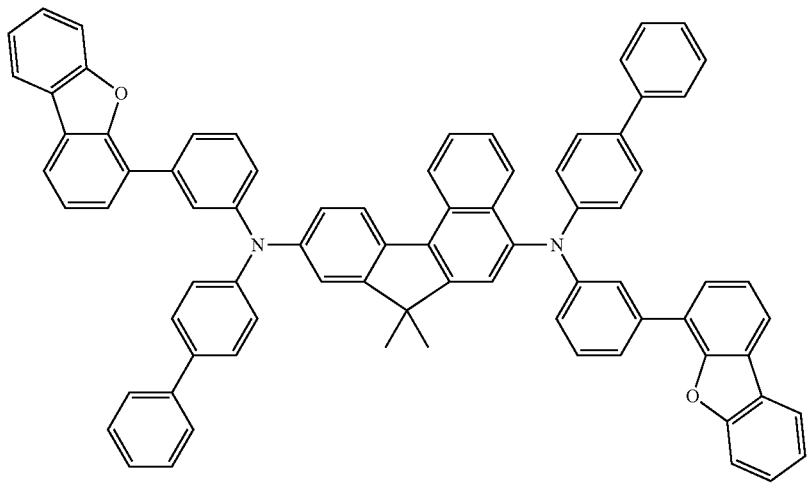
Compound 15
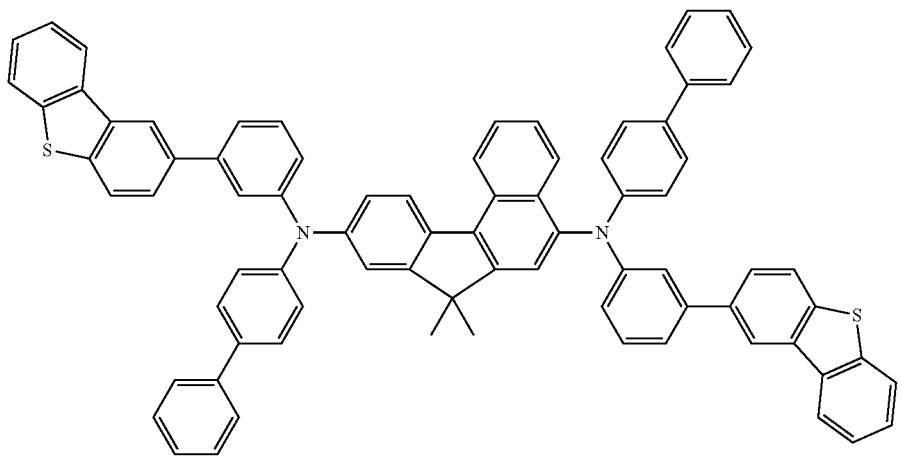

Compound 16
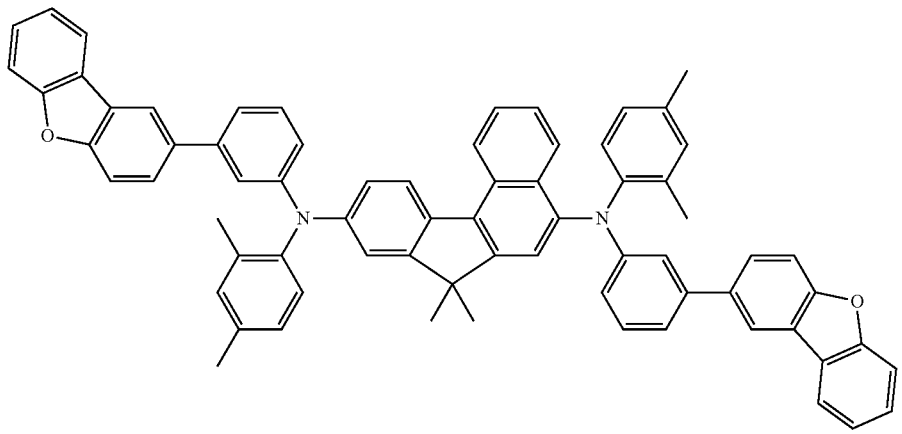
Compound 17
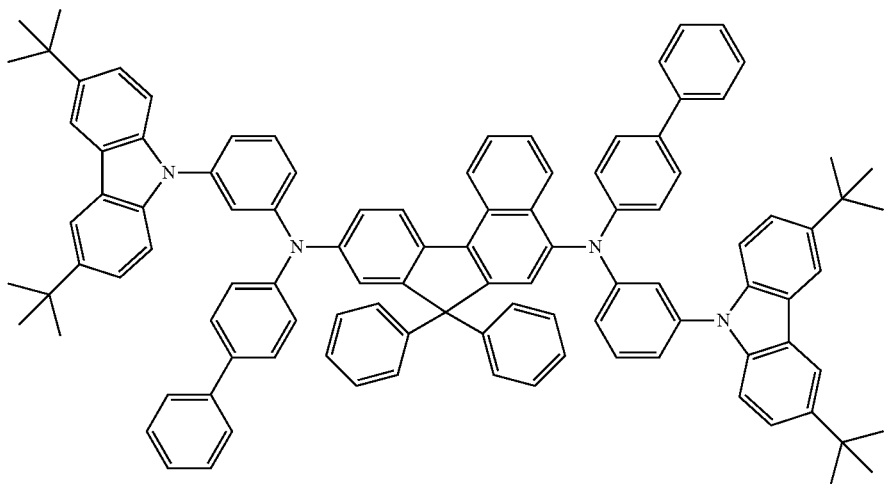
Compound 18
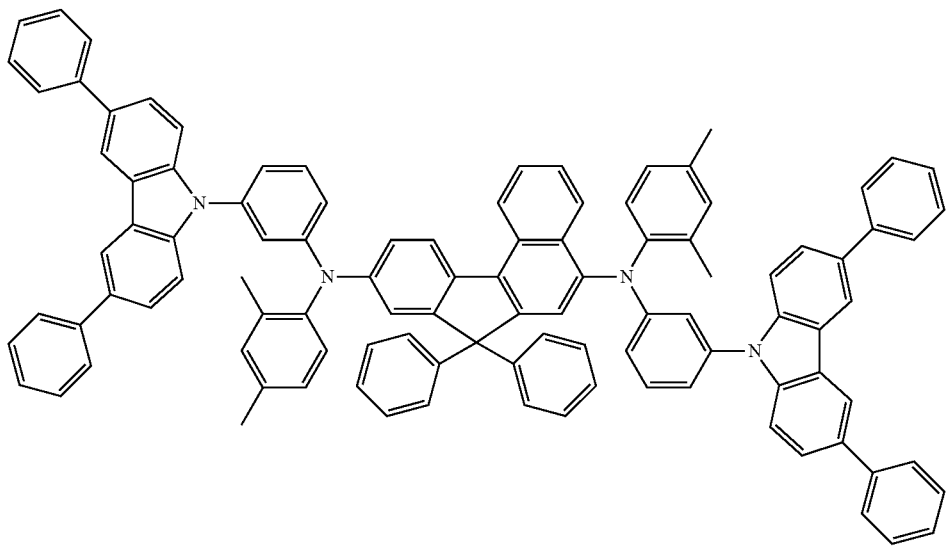

Compound 19
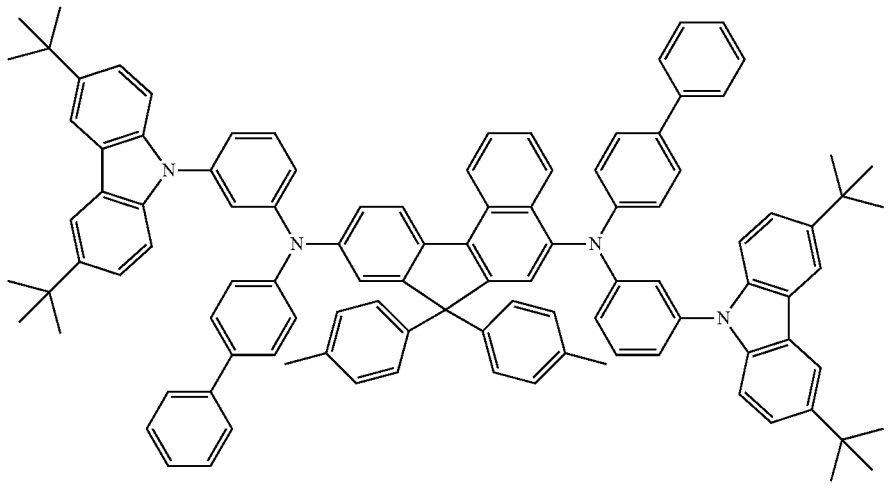
Compound 20
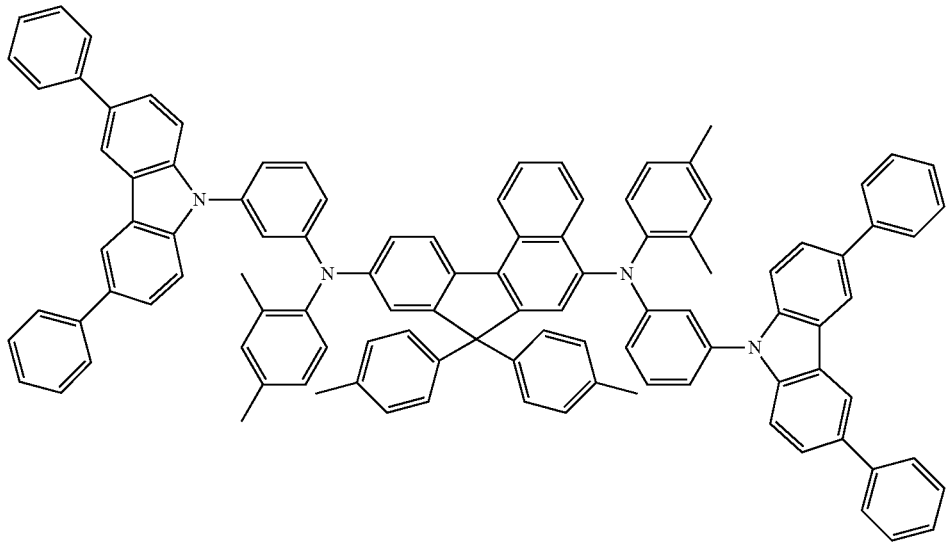
Compound 21
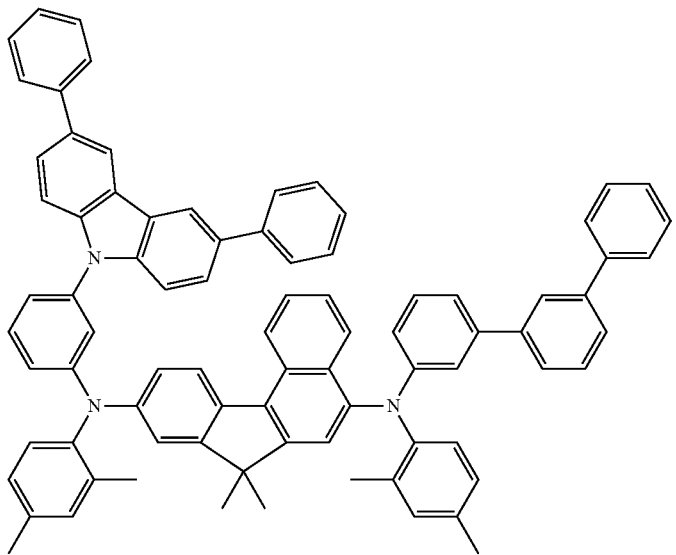

-continued
Compound 22
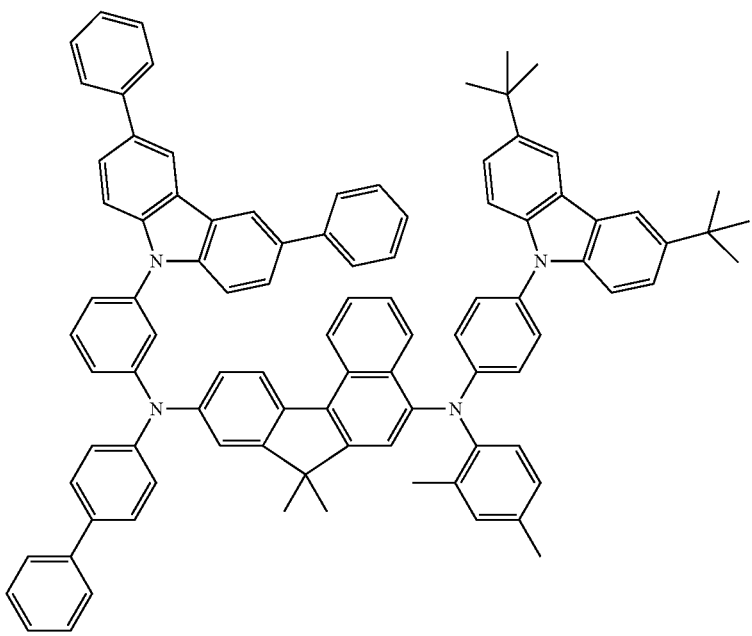
Compound 23
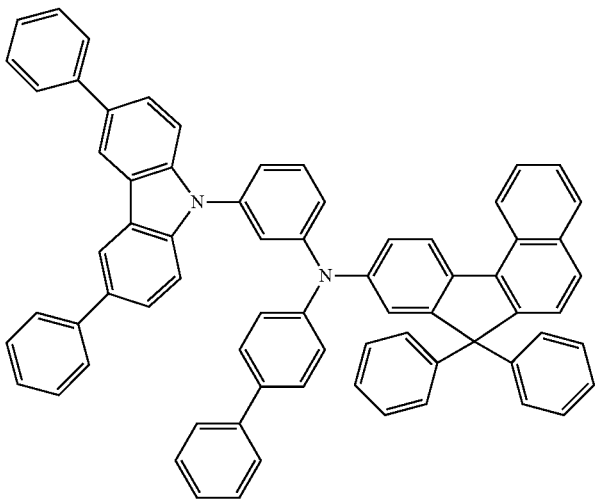
Compound 24
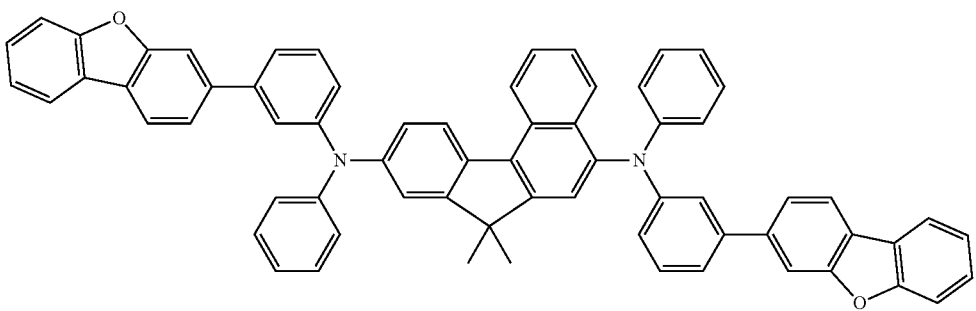

-continued
Compound 25
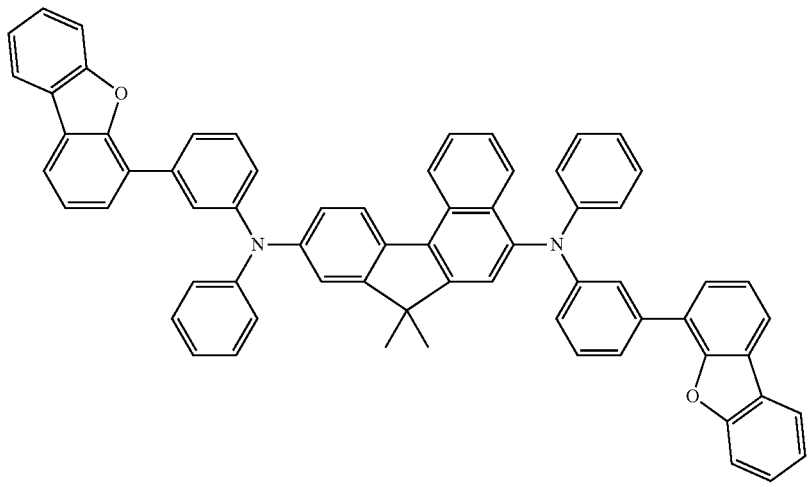
Compound 26
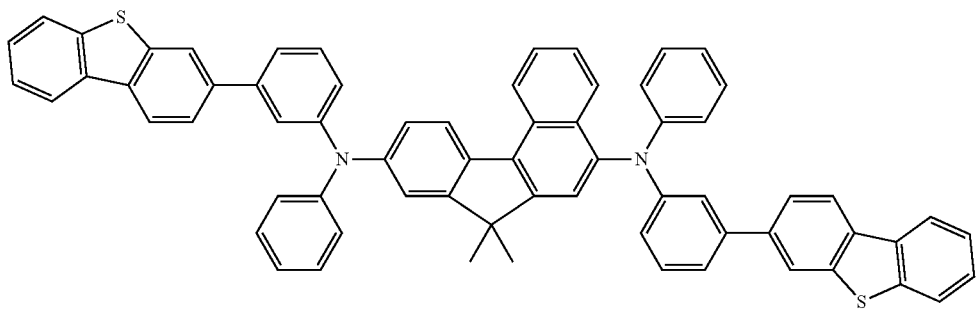
Compound 27
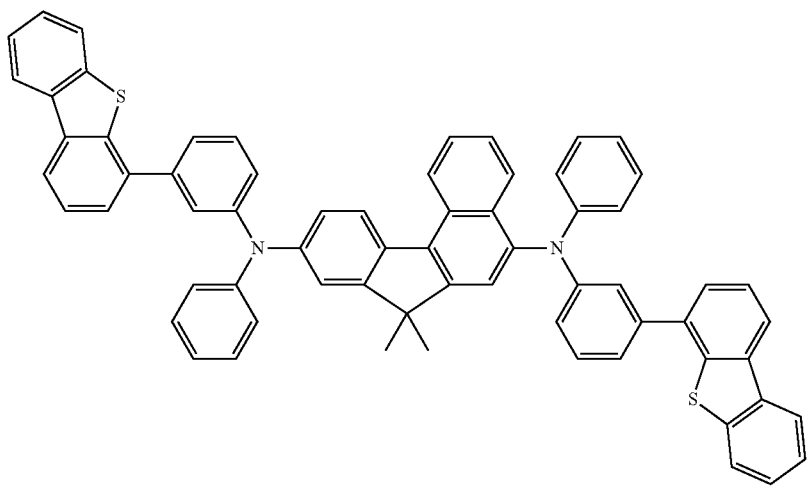
Compound 28
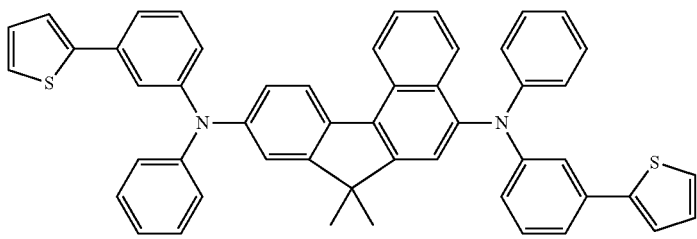

Compound 29
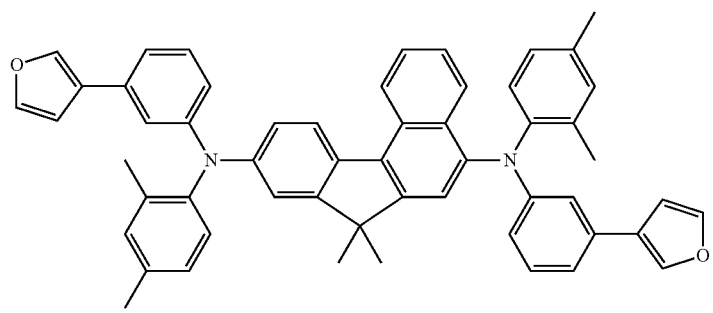
Compound 30
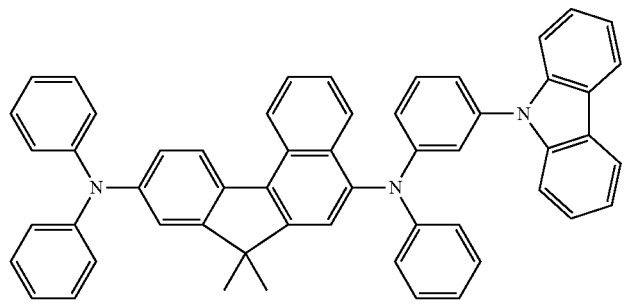
Compound 31
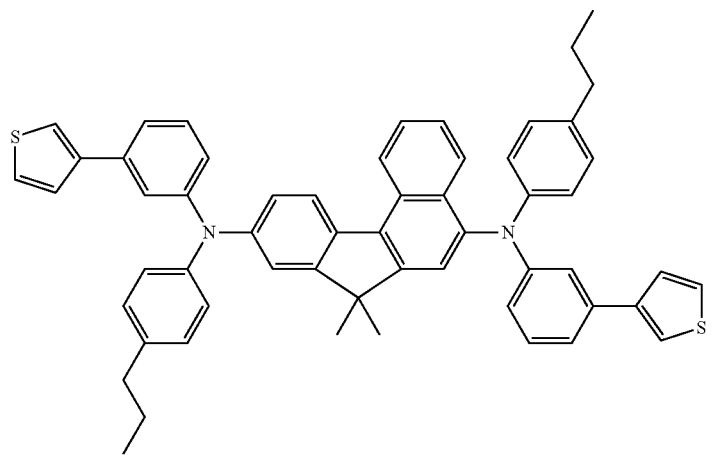
Compound 32
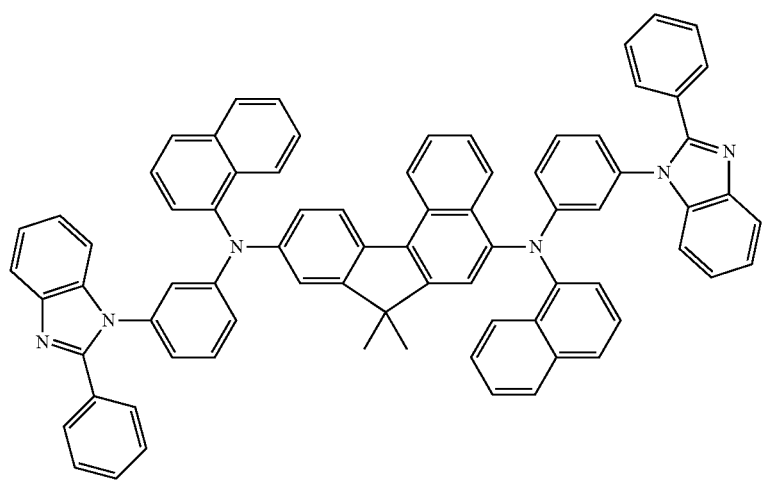

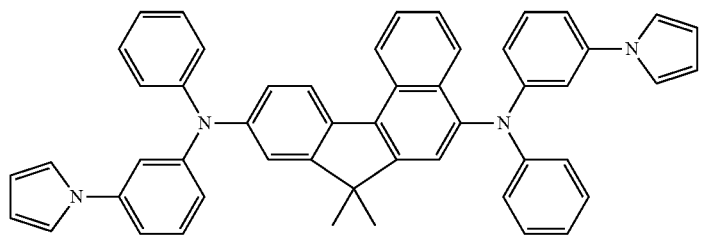
Compound 33
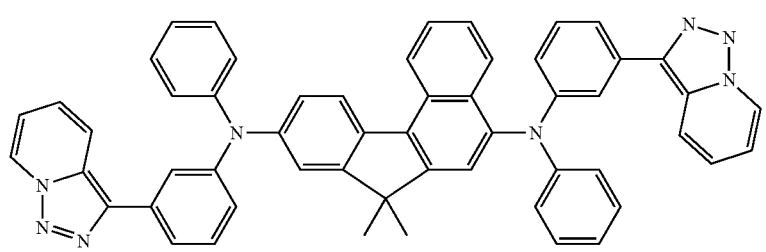
Compound 34
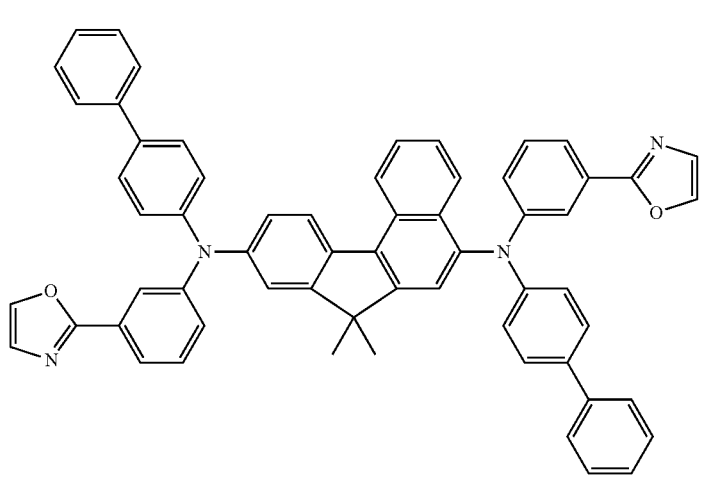
Compound 35
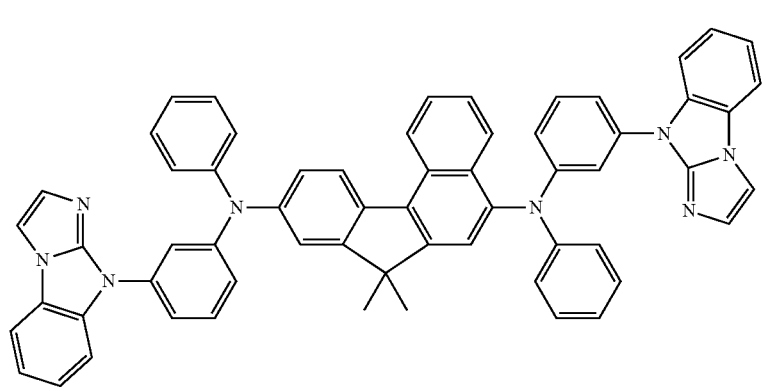
Compound 36

Compound 37
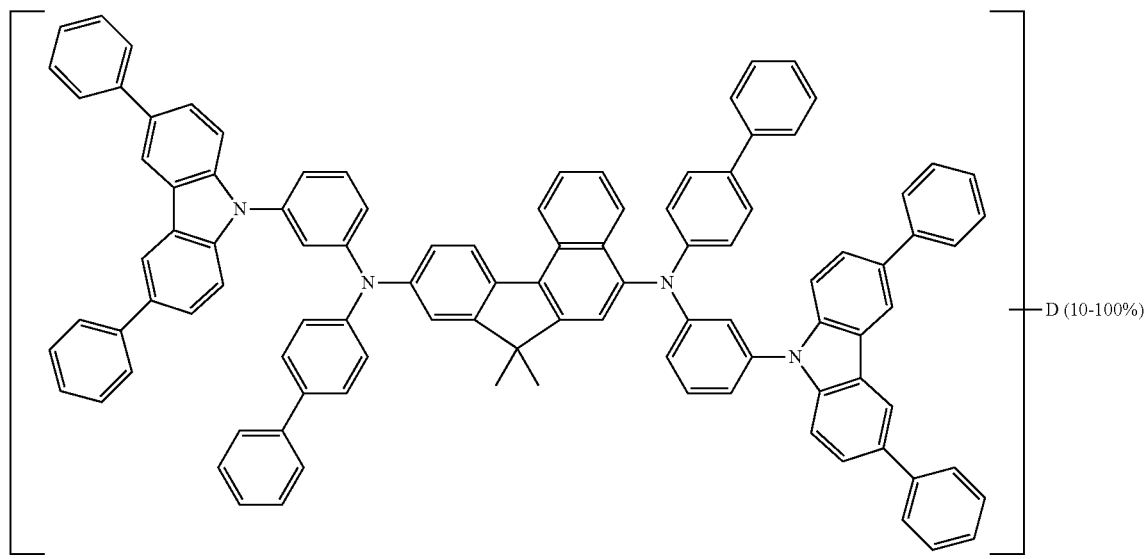
D (10-100%)
Compound 38
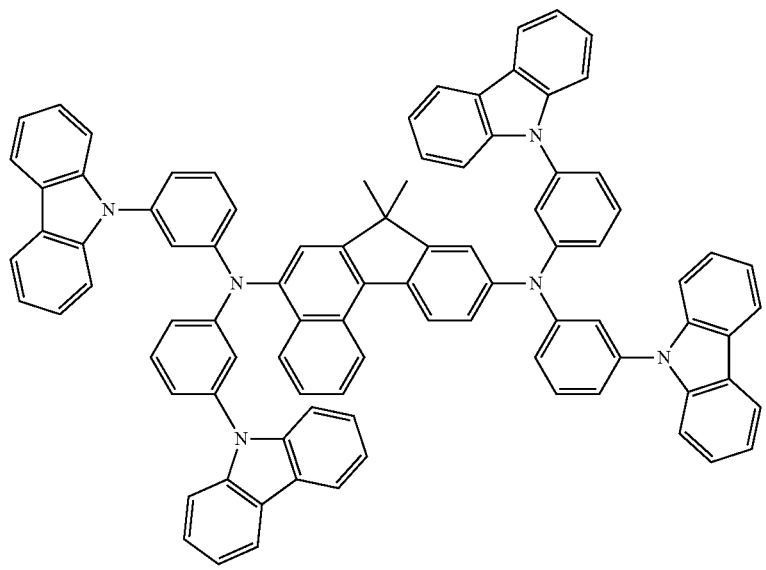
Compound 39
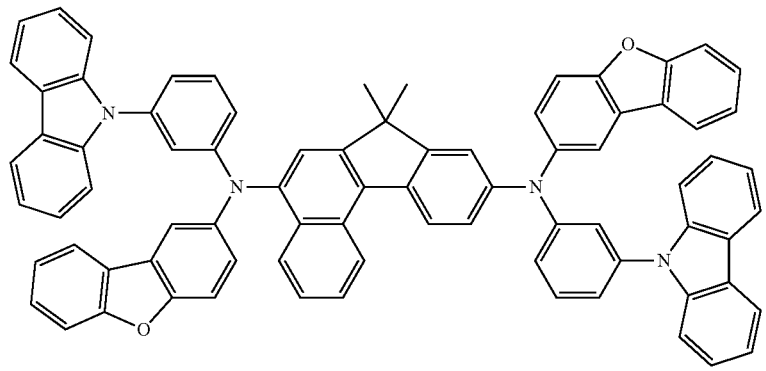

3. Compounds Having Formula II, Formula II-a, Formula II-b, or Formula II-c

The compounds having Formula II, Formula II-a, Formula II-b, or Formula II-c have the core benzofluorene structure shown below, where the numbers indicate the positions on the core.

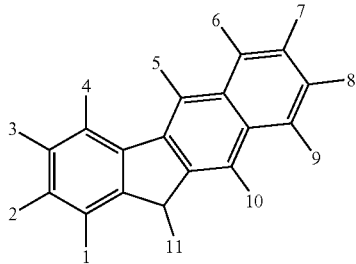

In some embodiments, the compounds having Formula II, Formula II-a, Formula II-b, or Formula II-c are useful as emissive materials. In some embodiments, the compounds are blue emissive materials. They can be used alone or as a dopant in a host material.

In some embodiments, the compounds having Formula II, Formula II-a, Formula II-b, or Formula II-c have deep blue color. In some embodiments, the compounds having Formula II, Formula II-a, Formula II-b, or Formula II-c have a photoluminescence y-coordinate of less than 0.10; in some embodiments, less than 0.090.

In some embodiments, devices including the compounds of Formula II, Formula II-a, Formula II-b, or Formula II-c have improved efficiencies. In some embodiments, the efficiency of a device including Formula II is greater than 4.5 cd/A at 1000 nits; in some embodiments, greater than 5.0 cd/A at 1000 nits.

In some embodiments, devices including the compounds of Formula II, Formula II-a, Formula II-b, or Formula II-c have increased lifetime. In some embodiments, devices including the compounds of Formula II may have a T70 greater than 1000 hours at 50° C. As used herein, T70 refers to the time to reach 70% of initial luminance. In some embodiments, devices including the compounds of Formula II may have a T70 greater than 1500 hours at 50° C.

In some embodiments, electroluminescent devices including the compounds of Formula II, Formula II-a, Formula II-b, or Formula II-c as emissive materials have deep blue color. In some embodiments, the x-coordinate is less than 0.15 and the y-coordinate is less than 0.10; in some embodiments, the y-coordinate is less than 0.090.

In some embodiments, the compounds have Formula II:

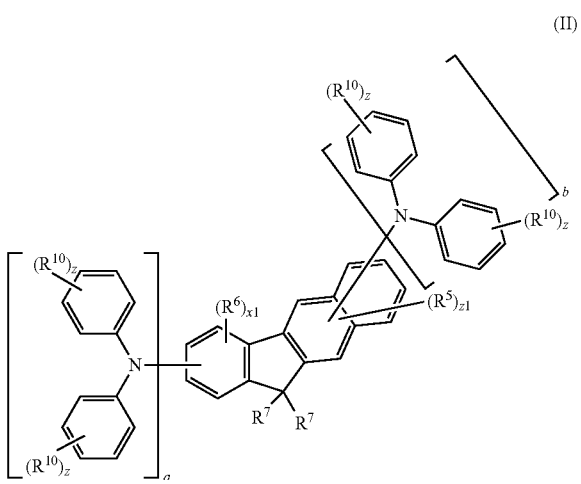

(II)

wherein:
$R^5$ and $R^6$ are the same or different at each occurrence and are selected from the group consisting of D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy;

$R^7$ is the same or different at each occurrence and is selected from the group consisting of alkyl, aryl, and deuterated analogs thereof, where two alkyl $R^7$ groups can be joined together to make a cycloalkyl spiro ring, and where two $R^7$ phenyl groups can be joined to form a spiro fluorene group;

$R^{10}$ is the same or different at each occurrence and is selected from the group consisting of D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, where adjacent R10 groups can be joined together to form a fused ring;

a and b are the same or different and are 0 or 1, with the proviso that a+b≥1;

x is the same or different at each occurrence and is an integer of 0-3;

x1 is an integer of 0-4, with the proviso that when a=1, x1 is 0-3;

y is the same or different at each occurrence and is an integer of 0-4;

z is the same or different at each occurrence and is an integer of 0-5; and z1 is an integer of 0-6, with the proviso that when b=1, z1 is 0-5.

In some embodiments of Formula II, the compound is deuterated. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula II, deuteration is present on the core benzofluorene group.

In some embodiments of Formula II, deuteration is present on one or more substituent groups.

In some embodiments of Formula II, deuteration is present on the core benzofluorene group and one or more substituent groups.

In some embodiments of Formula II, a=1 and b=0.
In some embodiments of Formula II, a=0 and b=1.
In some embodiments of Formula II, a=b=1.
In some embodiments of Formula II, a=1 and the amino nitrogen is bonded to position 1 on the benzofluorene core.
In some embodiments of Formula II, a=1 and the amino nitrogen is bonded to position 2 on the benzofluorene core.
In some embodiments of Formula II, a=1 and the amino nitrogen is bonded to position 3 on the benzofluorene core.
In some embodiments of Formula II, a=1 and the amino nitrogen is bonded to position 4 on the benzofluorene core.
In some embodiments of Formula II, b=1 and the amino nitrogen is bonded to position 5 on the benzofluorene core.

In some embodiments of Formula II, b=1 and the amino nitrogen is bonded to position 6 on the benzofluorene core.

In some embodiments of Formula II, b=1 and the amino nitrogen is bonded to position 7 on the benzofluorene core.

In some embodiments of Formula II, b=1 and the amino nitrogen is bonded to position 8 on the benzofluorene core.

In some embodiments of Formula II, b=1 and the amino nitrogen is bonded to position 9 on the benzofluorene core.

In some embodiments of Formula II, b=1 and the amino nitrogen is bonded to position 9 on the benzofluorene core.

In some embodiments of Formula II, $R^5$ is as described above for Formula I.

In some embodiments of Formula II, $R^6$ is as described above for Formula I.

In some embodiments of Formula II, $R^7$ is as described above for Formula I.

In some embodiments of Formula II, $R^{10}$ is as described above for Formula I-a.

In some embodiments, of Formula II, x1 is as described above for Formula I-a.

In some embodiments of Formula II, z is as described above for Formula I-a.

In some embodiments of Formula II, z1 is as described above for Formula I-b.

Any of the above embodiments of Formula II can be combined with one or more of the other embodiments, so long as they are not mutually exclusive. For example, the embodiment in which $R^{1a}$ is carbazole or deuterated carbazole can be combined with the embodiment where $R^{2a}$ is an alkyl or deuterated alkyl having 3-8 carbons and the embodiment where b=0. The same is true for the other non-mutually-exclusive embodiments discussed above. The skilled person would understand which embodiments were mutually exclusive and would thus readily be able to determine the combinations of embodiments that are contemplated by the present application.

In some embodiments, the compounds have Formula II-a:

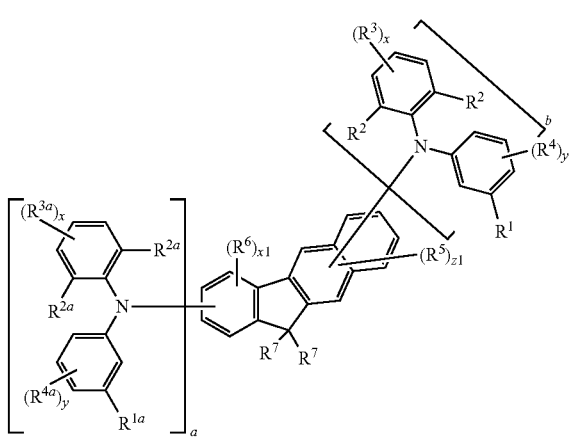

(II-a)

wherein:

$R^1$, $R^{1a}$, $R^2$, and $R^{2a}$ are the same or different at each occurrence and are selected from the group consisting of H, D, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, with the proviso that at least one of $R^1$ and $R^{1a}$ is heteroaryl or deuterated heteroaryl;

$R^3$, $R^{3a}$, $R^4$, $R^{4a}$, $R^5$, and $R^6$ are the same or different at each occurrence and are selected from the group consisting of D, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, wherein adjacent groups selected from $R^3$, $R^{3a}$, $R^4$, and $R^{4a}$ can be joined together to form a fused ring;

$R^7$ is the same or different at each occurrence and is selected from the group consisting of alkyl, aryl, and deuterated analogs thereof, where two alkyl $R^7$ groups can be joined together to make a cycloalkyl spiro ring, and where two $R^7$ phenyl groups can be joined to form a spiro fluorene group;

a and b are the same or different and are 0 or 1, with the proviso that a+b≥1;

x is the same or different at each occurrence and is an integer of 0-3;

x1 is an integer of 0-4, with the proviso that when a=1, x1 is 0-3;

y is the same or different at each occurrence and is an integer of 0-4;

z is the same or different at each occurrence and is an integer of 0-5; and z1 is an integer of 0-6, with the proviso that when b=1, z1 is 0-5.

In some embodiments of Formula II-a, the compound is deuterated. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula II-a, deuteration is present on the core benzofluorene group.

In some embodiments of Formula II-a, deuteration is present on one or more substituent groups.

In some embodiments of Formula II-a, deuteration is present on the core benzofluorene group and one or more substituent groups.

In some embodiments of Formula II-a, a=1 and b=0.

In some embodiments of Formula II-a, a=0 and b=1.

In some embodiments of Formula II-a, a=b=1.

In some embodiments of Formula II-a, a=1 and the amino nitrogen is bonded to position 1 on the benzofluorene core.

In some embodiments of Formula II-a, a=1 and the amino nitrogen is bonded to position 2 on the benzofluorene core.

In some embodiments of Formula II-a, a=1 and the amino nitrogen is bonded to position 3 on the benzofluorene core.

In some embodiments of Formula II-a, a=1 and the amino nitrogen is bonded to position 4 on the benzofluorene core.

In some embodiments of Formula II-a, b=1 and the amino nitrogen is bonded to position 5 on the benzofluorene core.

In some embodiments of Formula II-a, b=1 and the amino nitrogen is bonded to position 6 on the benzofluorene core.

In some embodiments of Formula II-a, b=1 and the amino nitrogen is bonded to position 7 on the benzofluorene core.

In some embodiments of Formula II-a, b=1 and the amino nitrogen is bonded to position 8 on the benzofluorene core.

In some embodiments of Formula II-a, b=1 and the amino nitrogen is bonded to position 9 on the benzofluorene core.

In some embodiments of Formula II-a, b=1 and the amino nitrogen is bonded to position 9 on the benzofluorene core.

In some embodiments of Formula II-a, $R^1$ is as described above for Formula I.

In some embodiments of Formula II-a, $R^{1a}$ is as described above for Formula I.

In some embodiments of Formula II-a, $R^2$ is as described above for Formula I.

In some embodiments of Formula II-a, $R^{2a}$ is as described above for Formula I.

In some embodiments of Formula II-a, $R^3$ is as described above for Formula I.

In some embodiments of Formula II-a, $R^{3a}$ is as described above for Formula I.

In some embodiments of Formula II-a, $R^4$ is as described above for Formula I.

In some embodiments of Formula II-a, $R^{4a}$ is as described above for Formula I.

In some embodiments of Formula II-a, $R^5$ is as described above for Formula I.

In some embodiments of Formula II-a, $R^6$ is as described above for Formula I.

In some embodiments of Formula II-a, $R^7$ is as described above for Formula I.

In some embodiments of Formula II-a, x is as described in Formula I.

In some embodiments of Formula II-a, x1 is as described in Formula I-a.

In some embodiments of Formula II-a, y is as described in Formula I.

In some embodiments of Formula II-a, z1 is as in Formula I-b,

Any of the above embodiments of Formula II-a can be combined with one or more of the other embodiments, so long as they are not mutually exclusive. For example, the embodiment in which a=1 and the amino nitrogen is bonded to position 3 on the benzofluorene core can be combined with the embodiment where $R^6$ is H or D. The same is true for the other non-mutually-exclusive embodiments discussed above. The skilled person would understand which embodiments were mutually exclusive and would thus readily be able to determine the combinations of embodiments that are contemplated by the present application.

In some embodiments, the compounds have Formula II-b:

wherein:

$R^5$ and $R^6$ are the same or different at each occurrence and are selected from the group consisting of D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy;

$R^7$ is the same or different at each occurrence and is selected from the group consisting of alkyl, aryl, and deuterated analogs thereof, where two alkyl $R^7$ groups can be joined together to make a cycloalkyl spiro ring, and where two $R^7$ phenyl groups can be joined to form a spiro fluorene group;

$R^{10}$ is the same or different at each occurrence and is selected from the group consisting of D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, where adjacent R10 groups can be joined together to form a fused ring;

a and b are the same or different and are 0 or 1, with the proviso that a+b≥1;

x is the same or different at each occurrence and is an integer of 0-3; and z is the same or different at each occurrence and is an integer of 0-5.

In some embodiments of Formula II-b, the compound is deuterated. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula II-b, deuteration is present on the core benzofluorene group.

In some embodiments of Formula II-b, deuteration is present on one or more substituent groups.

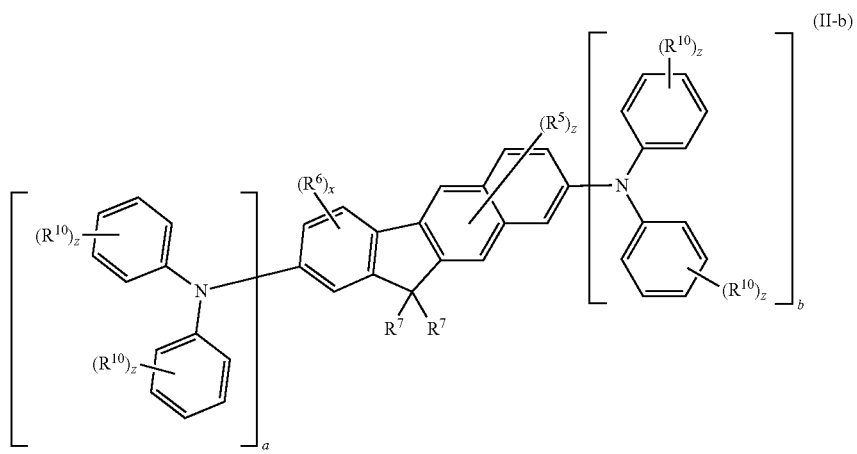

In some embodiments of Formula II-b, deuteration is present on the core benzofluorene group and one or more substituent groups.

In some embodiments of Formula II-b, a=1 and b=0. When b=0 the 8-position is H or $R^5$.

In some embodiments of Formula II-b, a=0 and b=1. When a=0 the 2-position is H or $R^6$.

In some embodiments of Formula II-b, a=b=1.

In some embodiments of Formula II-b, $R^5$ is as described above for Formula I.

In some embodiments of Formula II-b, $R^6$ is as described above for Formula I.

In some embodiments of Formula II-b, $R^7$ is as described above for Formula I.

In some embodiments of Formula II-b, at least one $R^{10}$ group is present and is selected from the group consisting of aryl, heteroaryl, and deuterated analogs thereof.

In some embodiments of Formula II-b, at least one $R^{10}$ group is present and is selected from the group consisting of heteroaryl and deuterated heteroaryl, where the heteroaryl has at least one ring atom which is selected from the group consisting of N, O, and S.

In some embodiments of Formula II-b, at least one $R^{10}$ group is present and is an N-heteroaryl selected from the group consisting of pyrrole, pyridine, pyrimidine, carbazole, imidazole, benzimidazole, imidazolobenzimidazole, triazole, benzotriazole, triazolopyridine, substituted derivatives thereof, and deuterated analogs thereof.

In some embodiments of Formula II-b, at least one $R^{10}$ group is present and is an S-heteroaryl selected form the group consisting of thiophene, benzothiophene, dibenzothiophene, and deuterated analogs thereof.

In some embodiments of Formula II-b, at least one $R^{10}$ group is present and is an O-heteroaryl selected from the group consisting of furan, benzofuran, dibenzofuran, and deuterated analogs thereof.

In some embodiments of Formula II-b, at least one $R^{10}$ group is present and is an N,O-heteroaryl selected from the group consisting of oxazole, benzoxazole, and deuterated analogs thereof.

In some embodiments of Formula II-b, at least one $R^{10}$ group is present and is an N,S-heteroaryl selected from the group consisting of thiazole, benzothiazole, and deuterated analogs thereof.

In some embodiments of Formula II-b, at least one $R^{10}$ group is present and is selected from the group consisting of Cz-1, Cz-2, Cz-3, DBT-1, DBT-2, DBF-1, DBF-2, BzO-1, BT-1, and deuterated analogs thereof, as those groups are defined above.

In some embodiments of Formula II-b, at least one $R^{10}$ group is present and is selected from the group consisting of phenyl, naphthyl, anthracenyl, combinations of such groups linked together covalently, and deuterated analogs thereof, where the groups may be further substituted with alkyl or deuterated alkyl groups.

In some embodiments of Formula II-b, at least one $R^{10}$ is present and is selected from the group consisting of phenyl, terphenyl, quaterphenyl, naphthyl, and deuterated analogs thereof.

In some embodiments of Formula II-b, at least one $R^{10}$ group is present and is selected from alkyl and deuterated alkyl having 1-12 carbons; in some embodiments, 3-8 carbons; in some embodiments 1-4 carbons.

In some embodiments of Formula II-b, x is 0.

In some embodiments of Formula II-b, x is 1.

In some embodiments of Formula II-b, x>1.

In some embodiments of Formula II-b, z with respect to $R^5$ is as described in Formula I.

In some embodiments of Formula II-b, z with respect to $R^{10}$ is as described in Formula I-a.

Any of the above embodiments of Formula II-b can be combined with one or more of the other embodiments, so long as they are not mutually exclusive. For example, the embodiment in which z=2 with respect to $R^{10}$ can be combined with the embodiment where at least one $R^{10}$ is present and is selected from the group consisting of phenyl, terphenyl, quaterphenyl, naphthyl, and deuterated analogs thereof. The same is true for the other non-mutually-exclusive embodiments discussed above. The skilled person would understand which embodiments were mutually exclusive and would thus readily be able to determine the combinations of embodiments that are contemplated by the present application.

In some embodiments, the compound has Formula II-c:

wherein:
$R^1$, $R^{1a}$, $R^2$, and $R^{2a}$ are the same or different at each occurrence and are selected from the group consisting of H, D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, with the proviso that at least one of $R^1$ and $R^{1a}$ is heteroaryl or deuterated heteroaryl;

$R^3$, $R^{3a}$, $R^4$, $R^{4a}$, $R^5$, and $R^6$ are the same or different at each occurrence and are selected from the group consisting of D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, wherein adjacent groups selected from $R^3$, $R^{3a}$, $R^4$, and $R^{4a}$ can be joined together to form a fused ring;

$R^7$ is the same or different at each occurrence and is selected from the group consisting of alkyl, aryl, and deuterated analogs thereof, where two alkyl $R^7$ groups can be joined together to make a cycloalkyl spiro ring, and where two $R^7$ phenyl groups can be joined to form a spiro fluorene group;

a and b are the same or different and are 0 or 1, with the proviso that a+b≥1;

x is the same or different at each occurrence and is an integer of 0-3;

y is the same or different at each occurrence and is an integer of 0-4; and z is an integer of 0-5.

In some embodiments of Formula II-c, the compound is deuterated.

In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula II-c, deuteration is present on the core benzofluorene group.

In some embodiments of Formula II-c, deuteration is present on one or more substituent groups.

In some embodiments of Formula II-c, deuteration is present on the core benzofluorene group and one or more substituent groups.

In some embodiments of Formula II-c, a=1 and b=0. When b=0 the 8-position is H or $R^5$.

In some embodiments of Formula II-c, a=0 and b=1. When a=0 the 2-position is H or $R^6$.

In some embodiments of Formula II-c, a=b=1.

In some embodiments of Formula II-c, $R^1$ is as described above for Formula I.

In some embodiments of Formula II-c, $R^{1a}$ is as described above for Formula I.

In some embodiments of Formula II-c, $R^2$ is as described above for Formula I.

In some embodiments of Formula II-c, $R^{2a}$ is as described above for Formula I.

In some embodiments of Formula II-c, $R^3$ is as described above for Formula I.

In some embodiments of Formula II-c, $R^{3a}$ is as described above for Formula I.

In some embodiments of Formula II-c, $R^4$ is as described above for Formula I.

In some embodiments of Formula II-c, $R^{4a}$ is as described above for Formula I.

In some embodiments of Formula II-c, $R^5$ is as described above for Formula I.

In some embodiments of Formula II-c, $R^6$ is as described above for Formula I.

In some embodiments of Formula II-c, $R^7$ is as described above for Formula I.

In some embodiments of Formula II-c, x is as described above for Formula I.

In some embodiments of Formula II-c, y is as described above for Formula I.

In some embodiments of Formula II-c, z is as described above for Formula I.

Any of the above embodiments of Formula II-c can be combined with one or more of the other embodiments, so long as they are not mutually exclusive. For example, the embodiment in which $R^1$ is carbazole or deuterated carbazole can be combined with the embodiment where $R^2$ is an alkyl or deuterated alkyl having 3-8 carbons and the embodiment where a=0. The same is true for the other non-mutually-exclusive embodiments discussed above. The skilled person would understand which embodiments were mutually exclusive and would thus readily be able to determine the combinations of embodiments that are contemplated by the present application.

The compounds of Formula II, Formula II-a, Formula II-b, and Formula II-c can be made using any technique that will yield a C—C or C—N bond. A variety of such techniques are known, such as Suzuki, Yamamoto, Stille, and Pd- or Ni-catalyzed C—N couplings.

The deuterated analog compounds can be prepared in a similar manner using deuterated precursor materials or, more generally, by treating the non-deuterated compound with deuterated solvent, such as d6-benzene, in the presence of a Lewis acid H/D exchange catalyst, such as aluminum trichloride or ethyl aluminum chloride, or acids such as $CF_3COOD$, DCl, etc. Deuteration reactions have also been described in published PCT application WO2011/053334.

Exemplary preparations are given in the Examples.

Examples of compounds having Formula II include, but are not limited to, the compounds shown below.

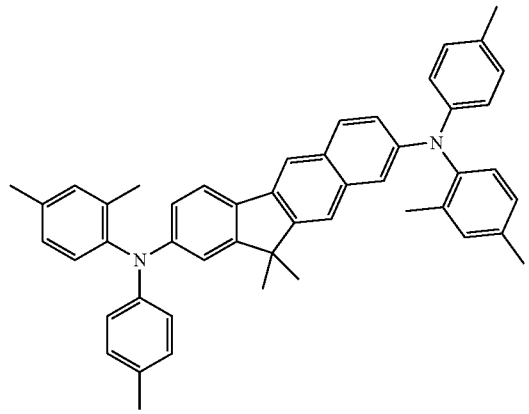

Compound 40

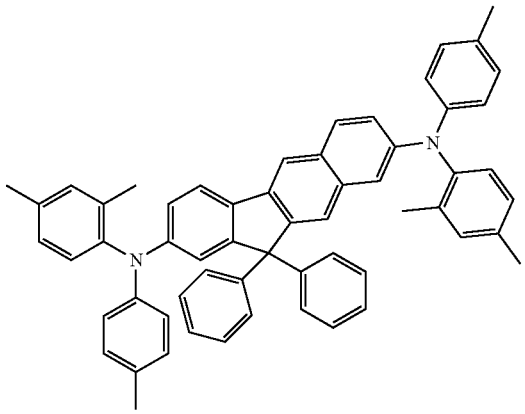

Compound 41

-continued
Compound 42
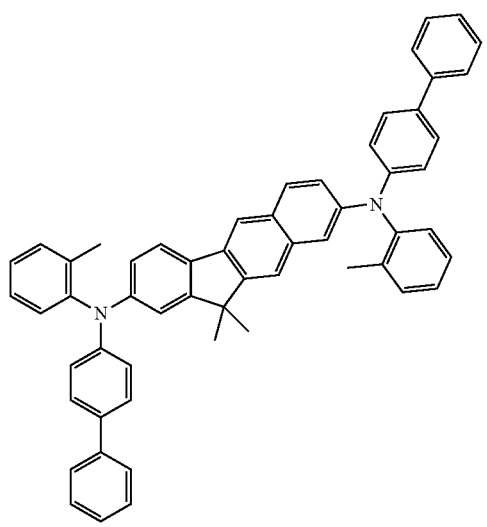
Compound 43
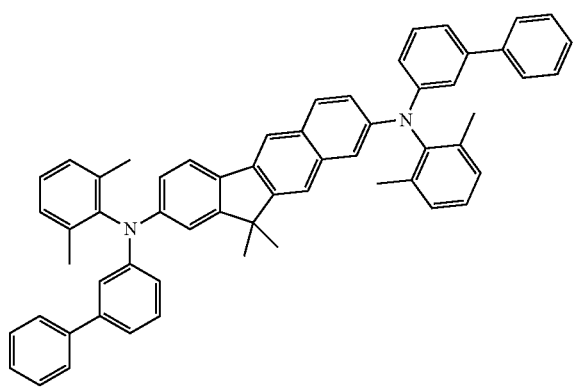
Compound 44
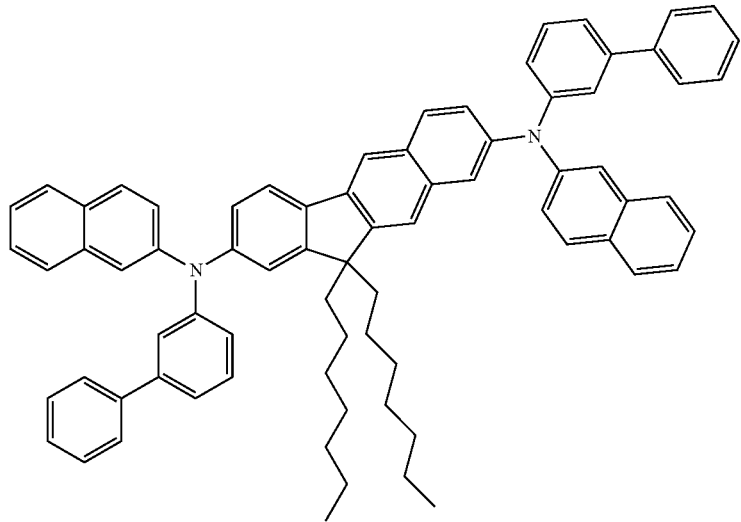

-continued
Compound 45
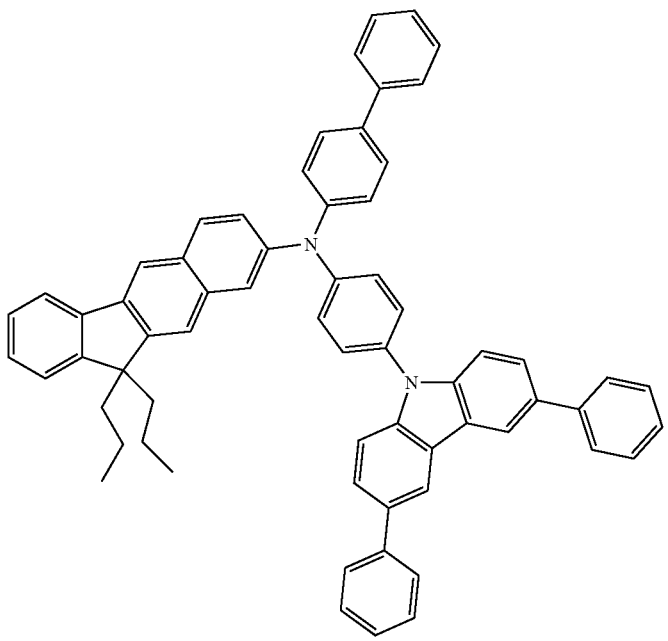
Compound 46
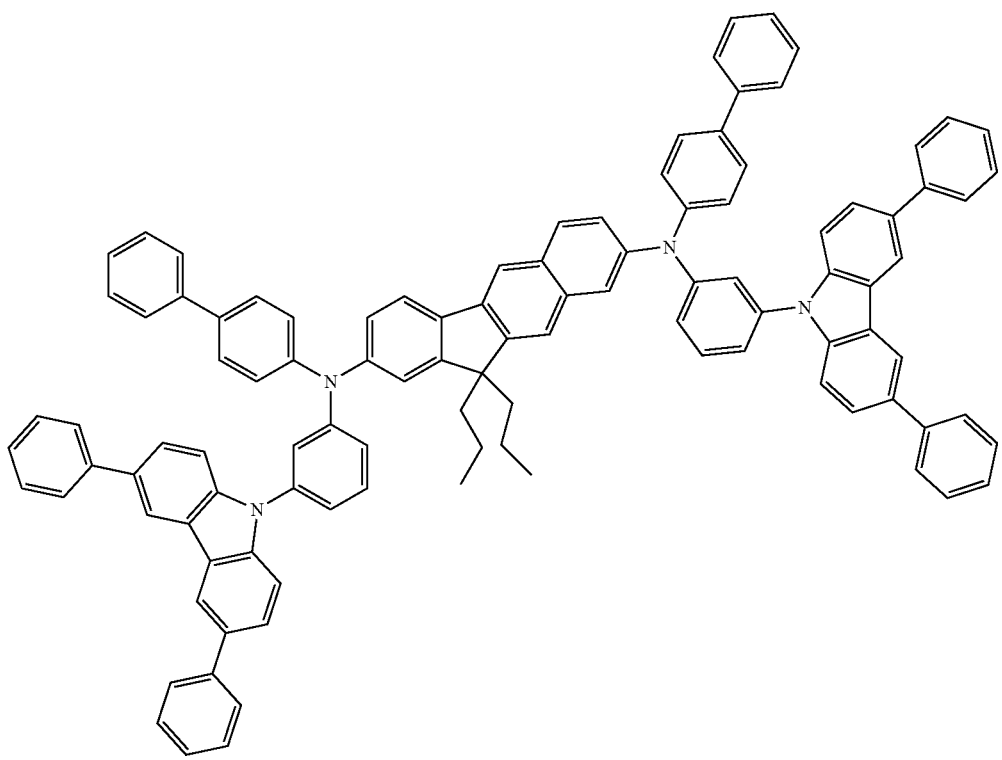

-continued
Compound 47
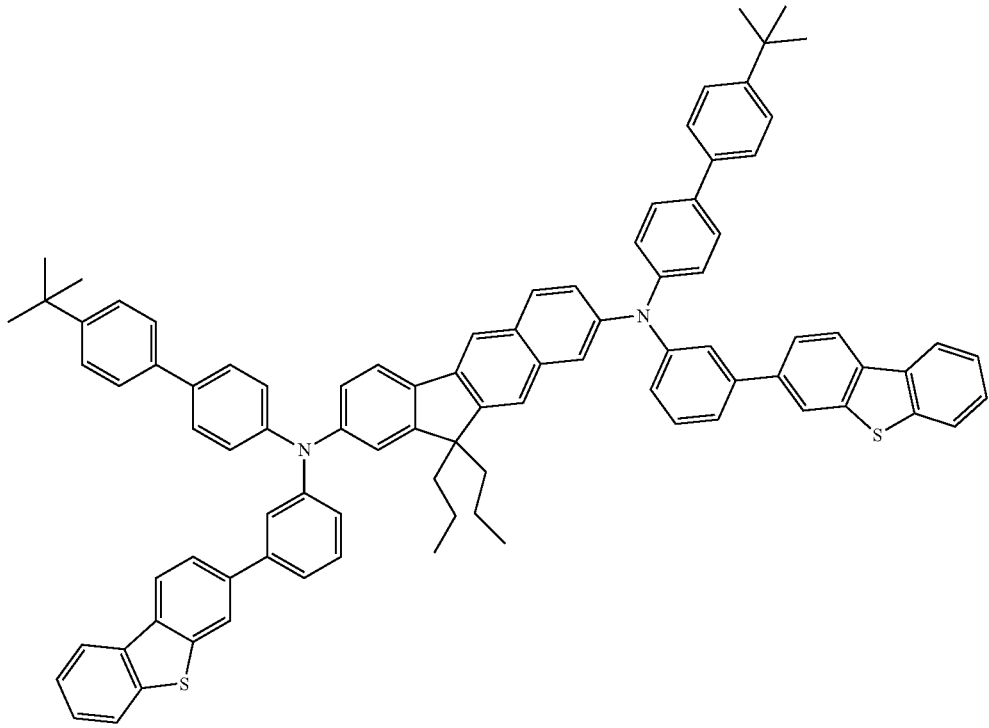
Compound 48
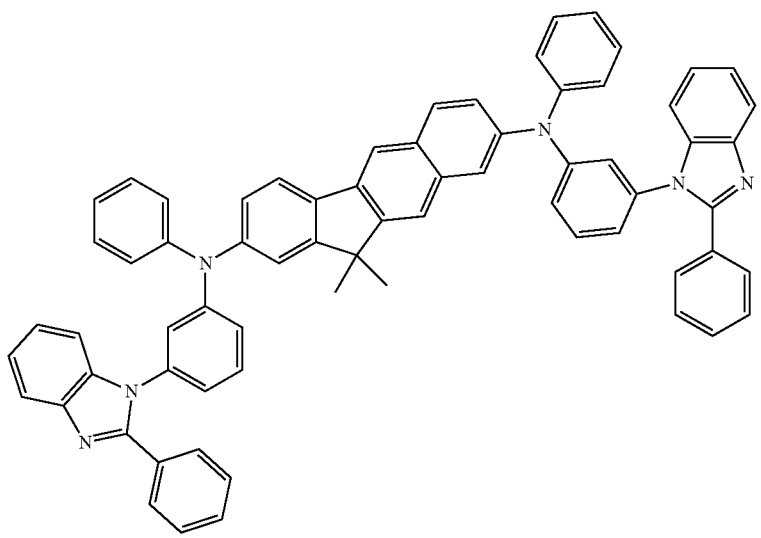

Compound 49

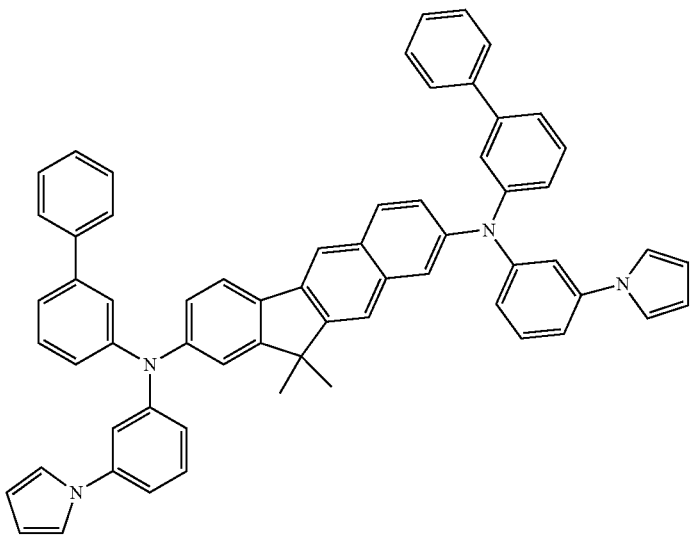

Compound 50

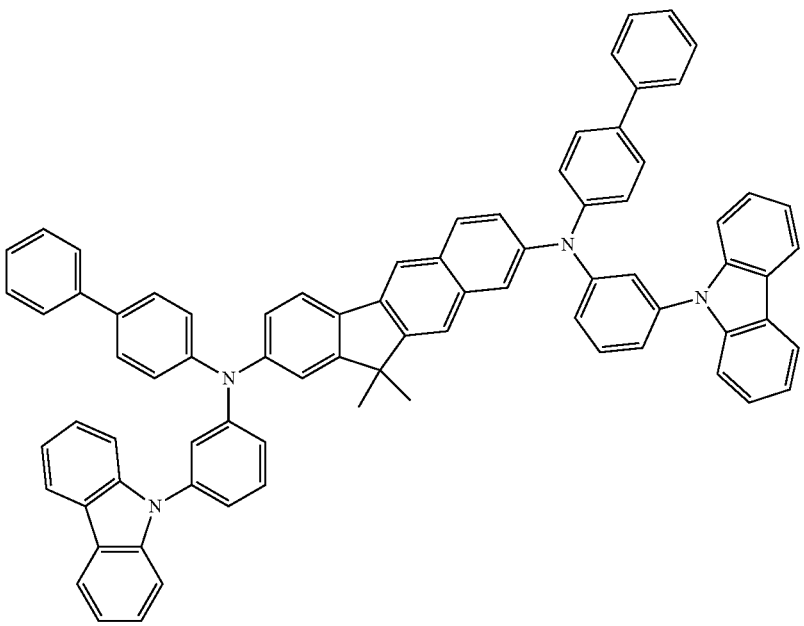

4. Compounds Having Formula III, Formula III-a, Formula III-b, Formula III-c, Formula III-d, or Formula III-e The compounds having Formula III, Formula III-a, Formula III-b, Formula III-c, Formula III-d, or Formula III-e have the core benzofluorene structure shown below, where the numbers indicate the positions on the core.

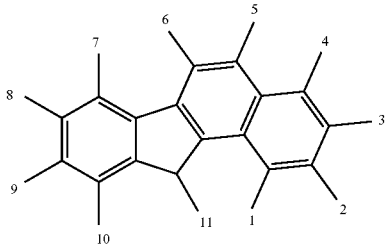

In some embodiments, the compounds having Formula III, Formula III-a, Formula III-b, Formula III-c, Formula III-d, or Formula III-e are useful as emissive materials. In some embodiments, the compounds are blue emissive materials. They can be used alone or as a dopant in a host material.

In some embodiments, the compounds having Formula III, Formula III-a, Formula III-b, Formula III-c, Formula III-d, or Formula III-e have deep blue color. In some embodiments, the compounds having Formula III, Formula III-a, Formula III-b, Formula III-c, Formula III-d, or Formula III-e have a photoluminescence y-coordinate of less than 0.10; in some embodiments, less than 0.090.

In some embodiments, devices including the compounds of Formula III, Formula III-a, Formula III-b, Formula III-c, Formula III-d, or Formula III-e have improved efficiencies. In some embodiments, the efficiency of a device including Formula III is greater than 4.5 cd/A at 1000 nits; in some embodiments, greater than 5.0 cd/A at 1000 nits.

In some embodiments, devices including the compounds of Formula III, Formula III-a, Formula III-b, Formula III-c, Formula III-d, or Formula III-e have increased lifetime. In some embodiments, devices including the compounds of Formula III have a T70 greater than 1000 hours at 50° C. As used herein, T70 refers to the time to reach 70% of initial luminance. In some embodiments, devices including the compounds of Formula III have a T70 greater than 1500 hours at 50° C.

In some embodiments, electroluminescent devices including the compounds of Formula III, Formula III-a, Formula III-b, Formula III-c, Formula III-d, or Formula III-e as emissive materials have deep blue color. In some embodiments, the x-coordinate is less than 0.15 and the y-coordinate is less than 0.10; in some embodiments, the y-coordinate is less than 0.090.

In some embodiments, the compounds have Formula III:

(III)

wherein:
- $R^5$ and $R^6$ are the same or different at each occurrence and are selected from the group consisting of D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy;
- $R^7$ is the same or different at each occurrence and is selected from the group consisting of alkyl, aryl, and deuterated analogs thereof, where two alkyl $R^7$ groups can be joined together to make a cycloalkyl spiro ring, and where two $R^7$ phenyl groups can be joined to form a spiro fluorene group;
- $R^{10}$ is the same or different at each occurrence and is selected from the group consisting of D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, where adjacent R10 groups can be joined together to form a fused ring;
- a and b are the same or different and are 0 or 1, with the proviso that a+b≥1;
- x is the same or different at each occurrence and is an integer of 0-3;
- x1 is an integer of 0-4, with the proviso that when a=1, x1 is 0-3;
- y is the same or different at each occurrence and is an integer of 0-4;
- z is the same or different at each occurrence and is an integer of 0-5; and
- z1 is an integer of 0-6, with the proviso that when b=1, z1 is 0-5.

In some embodiments of Formula III, the compound is deuterated. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula III, deuteration is present on the core benzofluorene group.

In some embodiments of Formula III, deuteration is present on one or more substituent groups.

In some embodiments of Formula III, deuteration is present on the core benzofluorene group and one or more substituent groups.

In some embodiments of Formula II, a=1 and b=0.
In some embodiments of Formula II, a=0 and b=1.
In some embodiments of Formula II, a=b=1.
In some embodiments of Formula III, a=1 and the amino nitrogen is bonded to position 7 on the benzofluorene core.
In some embodiments of Formula III, a=1 and the amino nitrogen is bonded to position 8 on the benzofluorene core.
In some embodiments of Formula III, a=1 and the amino nitrogen is bonded to position 9 on the benzofluorene core.
In some embodiments of Formula III, a=1 and the amino nitrogen is bonded to position 10 on the benzofluorene core.
In some embodiments of Formula III, b=1 and the amino nitrogen is bonded to position 1 on the benzofluorene core.
In some embodiments of Formula III, b=1 and the amino nitrogen is bonded to position 2 on the benzofluorene core.
In some embodiments of Formula III, b=1 and the amino nitrogen is bonded to position 3 on the benzofluorene core.
In some embodiments of Formula III, b=1 and the amino nitrogen is bonded to position 4 on the benzofluorene core.
In some embodiments of Formula III, b=1 and the amino nitrogen is bonded to position 5 on the benzofluorene core.
In some embodiments of Formula III, b=1 and the amino nitrogen is bonded to position 6 on the benzofluorene core.
In some embodiments of Formula III, $R^5$ is as described above for Formula I.
In some embodiments of Formula III, $R^6$ is as described above for Formula I.

In some embodiments of Formula III, $R^7$ is as described above for Formula I.

In some embodiments of Formula III, $R^{10}$ is as described above for Formula I-a.

In some embodiments, of Formula III, x1 is as described above for Formula I-a.

In some embodiments of Formula III, z is as described above for Formula I-a.

In some embodiments of Formula III, z1 is as described above for Formula I-b.

Any of the above embodiments of Formula III can be combined with one or more of the other embodiments, so long as they are not mutually exclusive. For example, the embodiment in which $R^{10}$ is carbazole or deuterated carbazole can be combined with the embodiment where x1=0. The same is true for the other non-mutually-exclusive embodiments discussed above. The skilled person would understand which embodiments were mutually exclusive and would thus readily be able to determine the combinations of embodiments that are contemplated by the present application.

In some embodiments, the compounds have Formula III-a:

a and b are the same or different and are 0 or 1, with the proviso that a+b≥1;

x is the same or different at each occurrence and is an integer of 0-3;

x1 is an integer of 0-4, with the proviso that when a=1, x1 is 0-3;

y is the same or different at each occurrence and is an integer of 0-4;

z is the same or different at each occurrence and is an integer of 0-5; and z1 is an integer of 0-6, with the proviso that when b=1, z1 is 0-5.

In some embodiments of Formula III-a, the compound is deuterated. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

(III-a)

wherein:
- $R^1$, $R^{1a}$, $R^2$, and $R^{2a}$ are the same or different at each occurrence and are selected from the group consisting of H, D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, with the proviso that at least one of $R^1$ and $R^{1a}$ is heteroaryl or deuterated heteroaryl;
- $R^3$, $R^{3a}$, $R^4$, $R^{4a}$, $R^5$, and $R^6$ are the same or different at each occurrence and are selected from the group consisting of D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, wherein adjacent groups selected from $R^3$, $R^{3a}$, $R^4$, and $R^{4a}$ can be joined together to form a fused ring;
- $R^7$ is the same or different at each occurrence and is selected from the group consisting of alkyl, aryl, and deuterated analogs thereof, where two alkyl $R^7$ groups can be joined together to make a cycloalkyl spiro ring, and where two $R^7$ phenyl groups can be joined to form a spiro fluorene group;

In some embodiments of Formula III-a, deuteration is present on the core benzofluorene group.

In some embodiments of Formula III-a, deuteration is present on one or more substituent groups.

In some embodiments of Formula III-a, deuteration is present on the core benzofluorene group and one or more substituent groups.

In some embodiments of Formula III-a, a=1 and b=0.

In some embodiments of Formula III-a, a=0 and b=1.

In some embodiments of Formula III-a, a=b=1.

In some embodiments of Formula III-a, a=1 and the amino nitrogen is bonded to position 7 on the benzofluorene core.

In some embodiments of Formula III-a, a=1 and the amino nitrogen is bonded to position 8 on the benzofluorene core.

In some embodiments of Formula III-a, a=1 and the amino nitrogen is bonded to position 9 on the benzofluorene core.

In some embodiments of Formula III-a, a=1 and the amino nitrogen is bonded to position 10 on the benzofluorene core.

In some embodiments of Formula III-a, b=1 and the amino nitrogen is bonded to position 1 on the benzofluorene core.

In some embodiments of Formula III-a, b=1 and the amino nitrogen is bonded to position 2 on the benzofluorene core.

In some embodiments of Formula III-a, b=1 and the amino nitrogen is bonded to position 3 on the benzofluorene core.

In some embodiments of Formula III-a, b=1 and the amino nitrogen is bonded to position 4 on the benzofluorene core.

In some embodiments of Formula III-a, b=1 and the amino nitrogen is bonded to position 5 on the benzofluorene core.

In some embodiments of Formula III-a, b=1 and the amino nitrogen is bonded to position 6 on the benzofluorene core.

In some embodiments of Formula III-a, $R^1$ is as described above for Formula I.

In some embodiments of Formula III-a, $R^{1a}$ is as described above for Formula I.

In some embodiments of Formula III-a, $R^2$ is as described above for Formula I.

In some embodiments of Formula III-a, $R^{2a}$ is as described above for Formula I.

In some embodiments of Formula III-a, $R^3$ is as described above for Formula I.

In some embodiments of Formula III-a, $R^{3a}$ is as described above for Formula I.

In some embodiments of Formula III-a, $R^4$ is as described above for Formula I.

In some embodiments of Formula III-a, $R^{4a}$ is as described above for Formula I.

In some embodiments of Formula III-a, $R^5$ is as described above for Formula I.

In some embodiments of Formula III-a, $R^6$ is as described above for Formula I.

In some embodiments of Formula III-a, $R^7$ is as described above for Formula I.

In some embodiments of Formula III-a, x is as described in Formula I.

In some embodiments of Formula III-a, x1 is as described in Formula I-a.

In some embodiments of Formula III-a, y is as described in Formula I.

In some embodiments of Formula III-a, z1 is as in Formula I-b.

Any of the above embodiments of Formula III-a can be combined with one or more of the other embodiments, so long as they are not mutually exclusive. For example, the embodiment in which adjacent $R^{3a}$ groups are joined together to form a fused ring can be combined with the embodiment where $R^2$ is an alkyl or deuterated alkyl having 3-8 carbons and the embodiment where a=b=1. The same is true for the other non-mutually-exclusive embodiments discussed above. The skilled person would understand which embodiments were mutually exclusive and would thus readily be able to determine the combinations of embodiments that are contemplated by the present application.

In some embodiments, the compounds have Formula III-b:

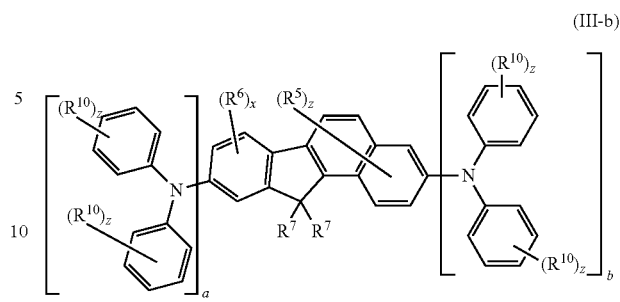

wherein:
$R^5$ and $R^6$ are the same or different at each occurrence and are selected from the group consisting of D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy;

$R^7$ is the same or different at each occurrence and is selected from the group consisting of alkyl, aryl, and deuterated analogs thereof, where two alkyl $R^7$ groups can be joined together to make a cycloalkyl spiro ring, and where two $R^7$ phenyl groups can be joined to form a spiro fluorene group;

$R^{10}$ is the same or different at each occurrence and is selected from the group consisting of D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, where adjacent R10 groups can be joined together to form a fused ring;

a and b are the same or different and are 0 or 1, with the proviso that a+b≥1;

x is the same or different at each occurrence and is an integer of 0-3; and z is the same or different at each occurrence and is an integer of 0-5.

In some embodiments of Formula III-b, the compound is deuterated. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula III-b, deuteration is present on the core benzofluorene group.

In some embodiments of Formula III-b, deuteration is present on one or more substituent groups.

In some embodiments of Formula III-b, deuteration is present on the core benzofluorene group and one or more substituent groups.

In some embodiments of Formula III-b, a=1 and b=0. When b=0 the 3-position is H or $R^5$.

In some embodiments of Formula III-b, a=0 and b=1. When a=0 the 9-position is H or $R^6$.

In some embodiments of Formula III-b, a=b=1.

In some embodiments of Formula III-b, $R^5$ is as described above for Formula I.

In some embodiments of Formula III-b, $R^6$ is as described above for Formula I.

In some embodiments of Formula III-b, $R^7$ is as described above for Formula I.

In some embodiments of Formula III-b, at least one $R^{10}$ group is present and is selected from the group consisting of aryl, heteroaryl, and deuterated analogs thereof.

In some embodiments of Formula III-b, at least one $R^{10}$ group is present and is selected from the group consisting of heteroaryl and deuterated heteroaryl, where the heteroaryl has at least one ring atom which is selected from the group consisting of N, O, and S.

In some embodiments of Formula III-b, at least one $R^{10}$ group is present and is an N-heteroaryl selected from the group consisting of pyrrole, pyridine, pyrimidine, carbazole, imidazole, benzimidazole, imidazolobenzimidazole, triazole, benzotriazole, triazolopyridine, substituted derivatives thereof, and deuterated analogs thereof.

In some embodiments of Formula III-b, at least one $R^{10}$ group is present and is an S-heteroaryl selected form the group consisting of thiophene, benzothiophene, dibenzothiophene, and deuterated analogs thereof.

In some embodiments of Formula III-b, at least one $R^{10}$ group is present and is an O-heteroaryl selected from the group consisting of furan, benzofuran, dibenzofuran, and deuterated analogs thereof.

In some embodiments of Formula III-b, at least one $R^{10}$ group is present and is an N,O-heteroaryl selected from the group consisting of oxazole, benzoxazole, and deuterated analogs thereof.

In some embodiments of Formula III-b, at least one $R^{10}$ group is present and is an N,S-heteroaryl selected from the group consisting of thiazole, benzothiazole, and deuterated analogs thereof.

In some embodiments of Formula III-b, at least one $R^{10}$ group is present and is selected from the group consisting of Cz-1, Cz-2, Cz-3, DBT-1, DBT-2, DBF-1, DBF-2, BzO-1, BT-1, and deuterated analogs thereof, as those groups are defined above.

In some embodiments of Formula III-b, at least one $R^{10}$ group is present and is selected from the group consisting of phenyl, naphthyl, anthracenyl, combinations of such groups linked together covalently, and deuterated analogs thereof, where the groups may be further substituted with alkyl or deuterated alkyl groups.

In some embodiments of Formula III-b, at least one $R^{10}$ is present and is selected from the group consisting of phenyl, terphenyl, quaterphenyl, naphthyl, and deuterated analogs thereof.

In some embodiments of Formula III-b, at least one $R^{10}$ group is present and is selected from alkyl and deuterated alkyl having 1-12 carbons; in some embodiments, 3-8 carbons; in some embodiments 1-4 carbons.

In some embodiments of Formula III-b, x is 0.

In some embodiments of Formula III-b, x is 1.

In some embodiments of Formula III-b, x>1.

In some embodiments of Formula III-b, z with respect to $R^5$ is as described in Formula I.

In some embodiments of Formula III-b, z with respect to $R^{10}$ is as described in Formula I-a.

Any of the above embodiments of Formula III-b can be combined with one or more of the other embodiments, so long as they are not mutually exclusive. For example, the embodiment in which at least one $R^{10}$ group is present and is selected from the group consisting of aryl, heteroaryl, and deuterated analogs thereof can be combined with the embodiment where at least one $R^{10}$ group is present and is selected from the group consisting of heteroaryl and deuterated heteroaryl, where the heteroaryl has at least one ring atom which is selected from the group consisting of N, O, and S. The same is true for the other non-mutually-exclusive embodiments discussed above. The skilled person would understand which embodiments were mutually exclusive and would thus readily be able to determine the combinations of embodiments that are contemplated by the present application.

In some embodiments, the compound has Formula III-c:

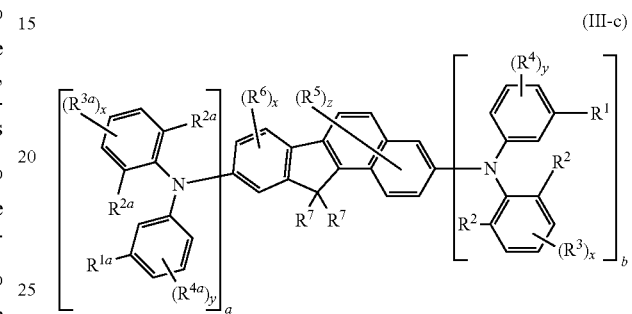

(III-c)

wherein:
$R^1$, $R^{1a}$, $R^2$, and $R^{2a}$ are the same or different at each occurrence and are selected from the group consisting of H, D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, with the proviso that at least one of $R^1$ and $R^{1a}$ is heteroaryl or deuterated heteroaryl;

$R^3$, $R^{3a}$, $R^4$, $R^{4a}$, $R^5$, and $R^6$ are the same or different at each occurrence and are selected from the group consisting of D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, wherein adjacent groups selected from $R^3$, $R^{3a}$, $R^4$, and $R^{4a}$ can be joined together to form a fused ring;

$R^7$ is the same or different at each occurrence and is selected from the group consisting of alkyl, aryl, and deuterated analogs thereof, where two alkyl $R^7$ groups can be joined together to make a cycloalkyl spiro ring, and where two $R^7$ phenyl groups can be joined to form a spiro fluorene group;

a and b are the same or different and are 0 or 1, with the proviso that a+b≥1;

x is the same or different at each occurrence and is an integer of 0-3;

y is the same or different at each occurrence and is an integer of 0-4; and z is an integer of 0-5.

In some embodiments of Formula III-c, the compound is deuterated. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula III-c, deuteration is present on the core benzofluorene group.

In some embodiments of Formula III-c, deuteration is present on one or more substituent groups.

In some embodiments of Formula III-c, deuteration is present on the core benzofluorene group and one or more substituent groups.

In some embodiments of Formula III-c, a=1 and b=0. When b=0 the 3-position is H or $R^5$.

In some embodiments of Formula III-c, a=0 and b=1. When a=0 the 9-position is H or $R^6$.

In some embodiments of Formula III-c, a=b=1.

In some embodiments of Formula III-c, $R^1$ is as described above for Formula I.

In some embodiments of Formula III-c, $R^{1a}$ is as described above for Formula I.

In some embodiments of Formula III-c, $R^2$ is as described above for Formula I.

In some embodiments of Formula III-c, $R^{2a}$ is as described above for Formula I.

In some embodiments of Formula III-c, $R^3$ is as described above for Formula I.

In some embodiments of Formula III-c, $R^{3a}$ is as described above for Formula I.

In some embodiments of Formula III-c, $R^4$ is as described above for Formula I.

In some embodiments of Formula III-c, $R^{4a}$ is as described above for Formula I.

In some embodiments of Formula III-c, $R^5$ is as described above for Formula I.

In some embodiments of Formula III-c, $R^6$ is as described above for Formula I.

In some embodiments of Formula III-c, $R^7$ is as described above for Formula I.

In some embodiments of Formula II-c, x is as described above for Formula I.

In some embodiments of Formula II-c, y is as described above for Formula I.

In some embodiments of Formula II-c, z is as described above for Formula I.

Any of the above embodiments of Formula III-c can be combined with one or more of the other embodiments, so long as they are not mutually exclusive. For example, the embodiment in which $R^1$ is a carbazole or deuterated carbazole can be combined with the embodiment in which $R^{1a}$ is carbazole or deuterated carbazole and with the embodiment where $R^{2a}$ is silyl or deuterated silyl. The same is true for the other non-mutually-exclusive embodiments discussed above. The skilled person would understand which embodiments were mutually exclusive and would thus readily be able to determine the combinations of embodiments that are contemplated by the present application.

In some embodiments, the compounds have Formula III-d:

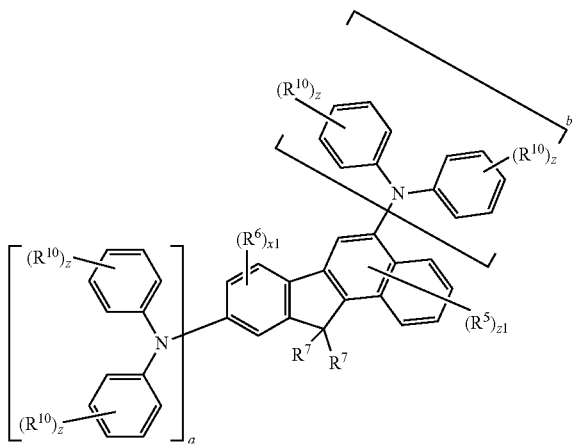

(III-d)

wherein:
$R^5$ and $R^6$ are the same or different at each occurrence and are selected from the group consisting of D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy;
$R^7$ is the same or different at each occurrence and is selected from the group consisting of alkyl, aryl, and deuterated analogs thereof, where two alkyl $R^7$ groups can be joined together to make a cycloalkyl spiro ring, and where two $R^7$ phenyl groups can be joined to form a spiro fluorene group;
$R^{10}$ is the same or different at each occurrence and is selected from the group consisting of D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, where adjacent R10 groups can be joined together to form a fused ring;
a and b are the same or different and are 0 or 1, with the proviso that a+b≥1;
x is the same or different at each occurrence and is an integer of 0-3;
x1 is an integer of 0-4, with the proviso that when a=1, x1 is 0-3;
y is the same or different at each occurrence and is an integer of 0-4;
z is the same or different at each occurrence and is an integer of 0-5; and
z1 is an integer of 0-6, with the proviso that when b=1, z1 is 0-5.

In some embodiments of Formula III-d, the compound is deuterated. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula III-d, deuteration is present on the core benzofluorene group.

In some embodiments of Formula III-d, deuteration is present on one or more substituent groups.

In some embodiments of Formula III-d, deuteration is present on the core benzofluorene group and one or more substituent groups.

In some embodiments of Formula III-d, a=1 and b=0. When b=0 the 3-position is H or $R^5$.

In some embodiments of Formula III-d, a=0 and b=1. When a=0 the 9-position is H or $R^6$.

In some embodiments of Formula III-d, a=b=1.

In some embodiments of Formula III-d, $R^5$ is as described above for Formula I.

In some embodiments of Formula III-d, $R^6$ is as described above for Formula I.

In some embodiments of Formula III-d, $R^7$ is as described above for Formula I.

In some embodiments of Formula III-d, $R^{10}$ is as described above for Formula I-a.

In some embodiments, of Formula III-d, x1 is as described above for Formula I-a.

In some embodiments of Formula III-d, z is as described above for Formula I-a.

In some embodiments of Formula III-d, z1 is as described above for Formula I-b.

Any of the above embodiments of Formula III-d can be combined with one or more of the other embodiments, so long as they are not mutually exclusive. For example, the embodiment in which $R^5$ is aryl or deuterated aryl can be combined with the embodiment where $R^6$ is H or D. The same is true for the other non-mutually-exclusive embodiments discussed above. The skilled person would understand which embodiments were mutually exclusive and would thus readily be able to determine the combinations of embodiments that are contemplated by the present application.

In some embodiments, the compounds have Formula III-e:

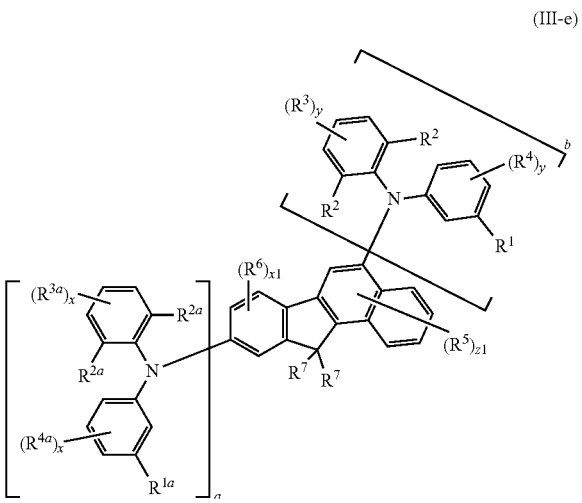

(III-e)

wherein:
$R^1$, $R^{1a}$, $R^2$, and $R^{2a}$ are the same or different at each occurrence and are selected from the group consisting of H, D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, with the proviso that at least one of $R^1$ and $R^{1a}$ is heteroaryl or deuterated heteroaryl;

$R^3$, $R^{3a}$, $R^4$, $R^{4a}$, $R^5$, and $R^6$ are the same or different at each occurrence and are selected from the group consisting of D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, wherein adjacent groups selected from $R^3$, $R^{3a}$, $R^4$, and $R^{4a}$ can be joined together to form a fused ring;

$R^7$ is the same or different at each occurrence and is selected from the group consisting of alkyl, aryl, and deuterated analogs thereof, where two alkyl $R^7$ groups can be joined together to make a cycloalkyl spiro ring, and where two $R^7$ phenyl groups can be joined to form a spiro fluorene group;

a and b are the same or different and are 0 or 1, with the proviso that a+b≥1;

x is the same or different at each occurrence and is an integer of 0-3;

x1 is an integer of 0-4, with the proviso that when a=1, x1 is 0-3;

y is the same or different at each occurrence and is an integer of 0-4;

z is the same or different at each occurrence and is an integer of 0-5; and z1 is an integer of 0-6, with the proviso that when b=1, z1 is 0-5.

In some embodiments of Formula III-e, the compound is deuterated. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula III-e, deuteration is present on the core benzofluorene group.

In some embodiments of Formula III-e, deuteration is present on one or more substituent groups.

In some embodiments of Formula III-e, deuteration is present on the core benzofluorene group and one or more substituent groups.

In some embodiments of Formula III-a, a=1 and b=0. When b=0, the 5-position is H or $R^5$.

In some embodiments of Formula III-a, a=0 and b=1. When a=0, the 9-position is H or $R^6$.

In some embodiments of Formula III-a, a=b=1.

In some embodiments of Formula III-e, $R^1$ is as described above for Formula I.

In some embodiments of Formula III-e, $R^{1a}$ is as described above for Formula I.

In some embodiments of Formula III-e, $R^2$ is as described above for Formula I.

In some embodiments of Formula III-e, $R^{2a}$ is as described above for Formula I.

In some embodiments of Formula III-e, $R^3$ is as described above for Formula I.

In some embodiments of Formula III-e, $R^{3a}$ is as described above for Formula I.

In some embodiments of Formula III-e, $R^4$ is as described above for Formula I.

In some embodiments of Formula III-e, $R^{4a}$ is as described above for Formula I.

In some embodiments of Formula III-e, $R^5$ is as described above for Formula I.

In some embodiments of Formula III-e, $R^6$ is as described above for Formula I.

In some embodiments of Formula III-e, $R^7$ is as described above for Formula I.

In some embodiments of Formula III-e, x is as described above in Formula I.

In some embodiments of Formula III-e, x1 is as described above in Formula I-a.

In some embodiments of Formula III-e, y is as described above in Formula I.

In some embodiments of Formula III-e, z1 is as described above in Formula I-b.

Any of the above embodiments of Formula III-e can be combined with one or more of the other embodiments, so long as they are not mutually exclusive. For example, the embodiment in which $R^{1a}$ is alkyl or deuterated alkyl can be combined with the embodiment where $R^{2a}$ is an alkyl or deuterated alkyl having 3-8 carbons and the embodiment where two $R^7$ phenyl groups are joined to form a spiro fluorene group. The same is true for the other non-mutually-exclusive embodiments discussed above. The skilled person would understand which embodiments were mutually exclusive and would thus readily be able to determine the combinations of embodiments that are contemplated by the present application.

The compounds of Formula III, Formula III-a, Formula III-b, Formula III-c, Formula III-d, or Formula III-e can be made using any technique that will yield a C—C or C—N bond. A variety of such techniques are known, such as Suzuki, Yamamoto, Stille, and Pd- or Ni-catalyzed C—N couplings.

The deuterated analog compounds can be prepared in a similar manner using deuterated precursor materials or, more generally, by treating the non-deuterated compound with deuterated solvent, such as d6-benzene, in the presence of a Lewis acid H/D exchange catalyst, such as aluminum trichloride or ethyl aluminum chloride, or acids such as $CF_3COOD$, DCl, etc. Deuteration reactions have also been described in published PCT application WO2011/053334.

Exemplary preparations are given in the Examples.

Examples of compounds having Formula III, Formula III-a, Formula III-b, Formula III-c, Formula III-d, or Formula III-e include, but are not limited to, the compounds shown below.

Compound 51

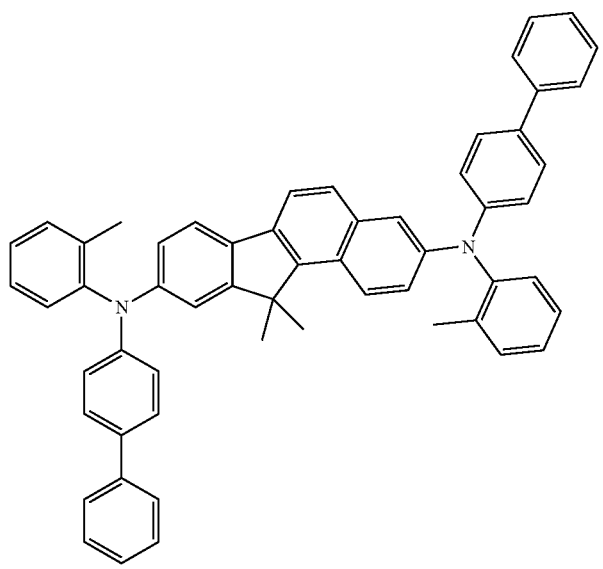

Compound 52

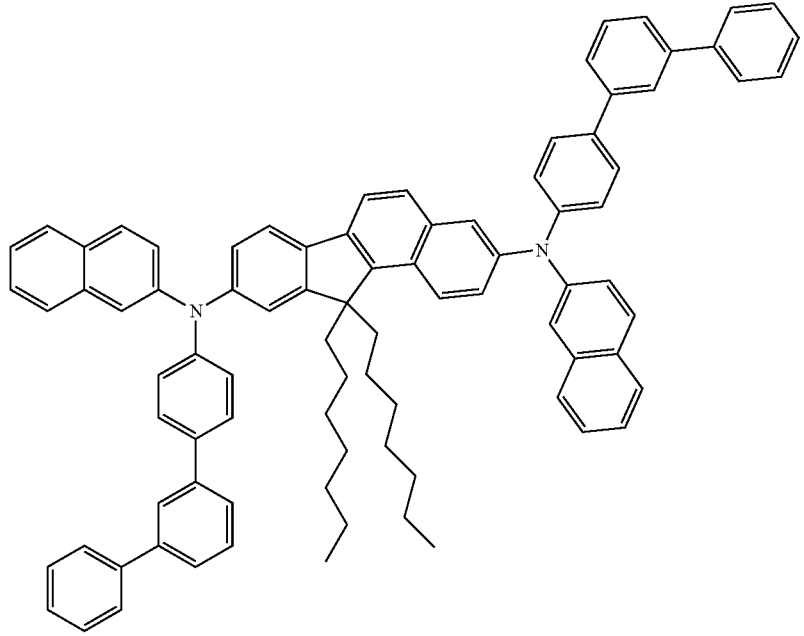

Compound 53
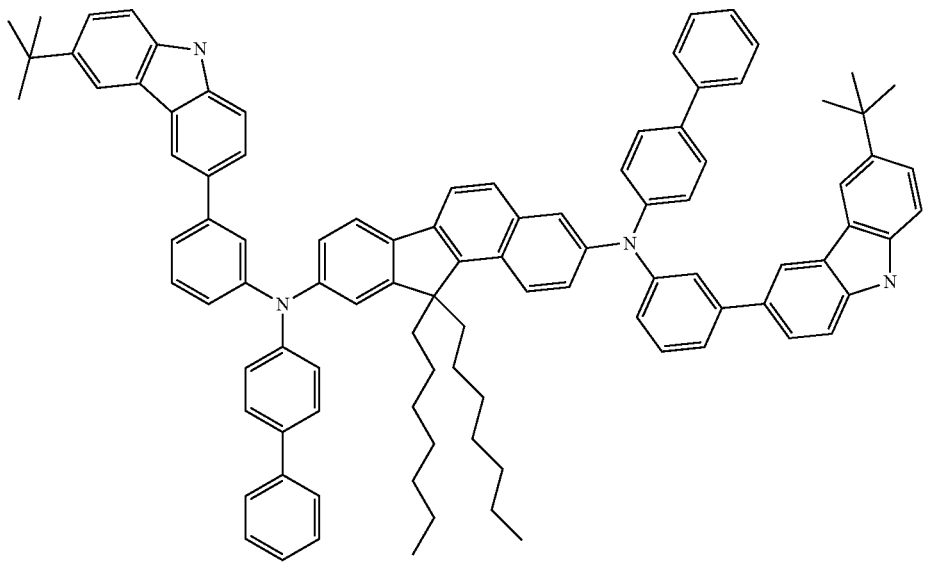
Compound 54
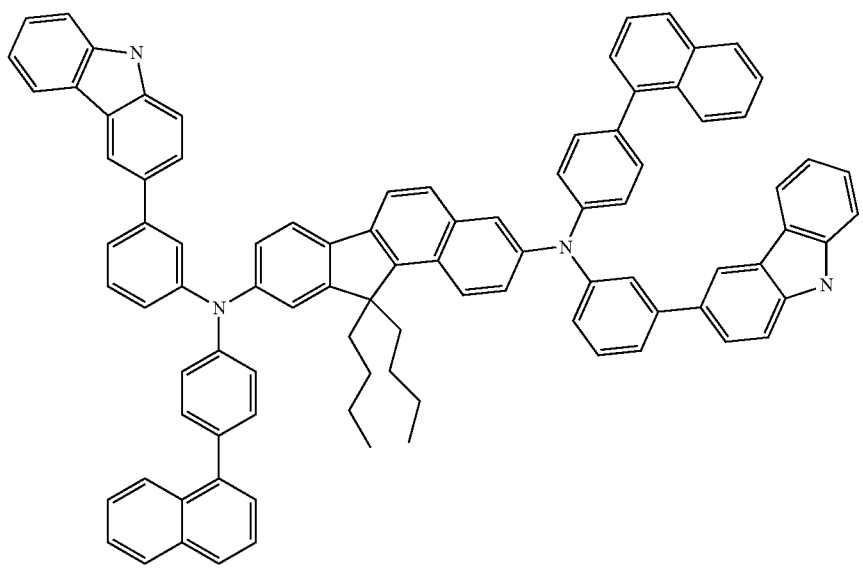
Compound 55
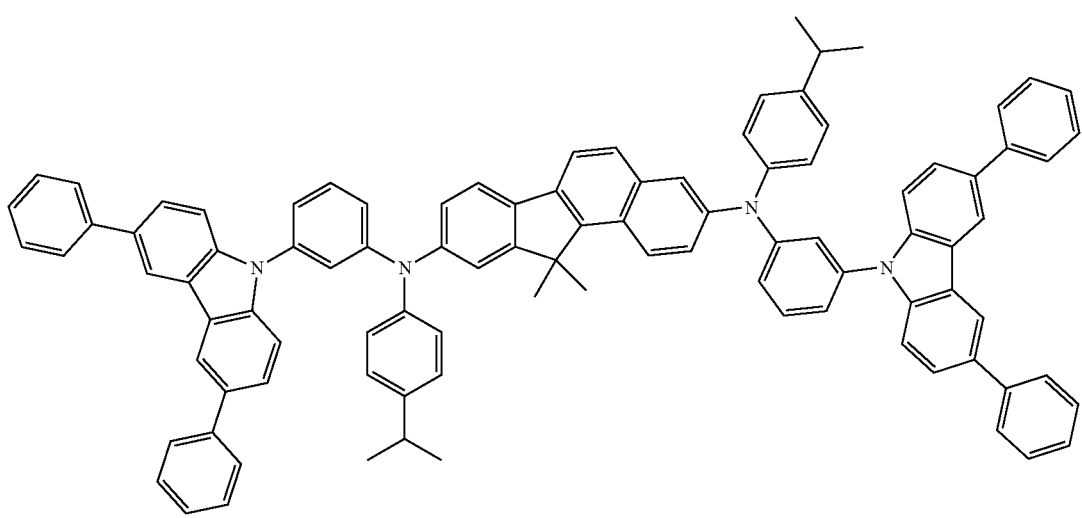

-continued
Compound 56
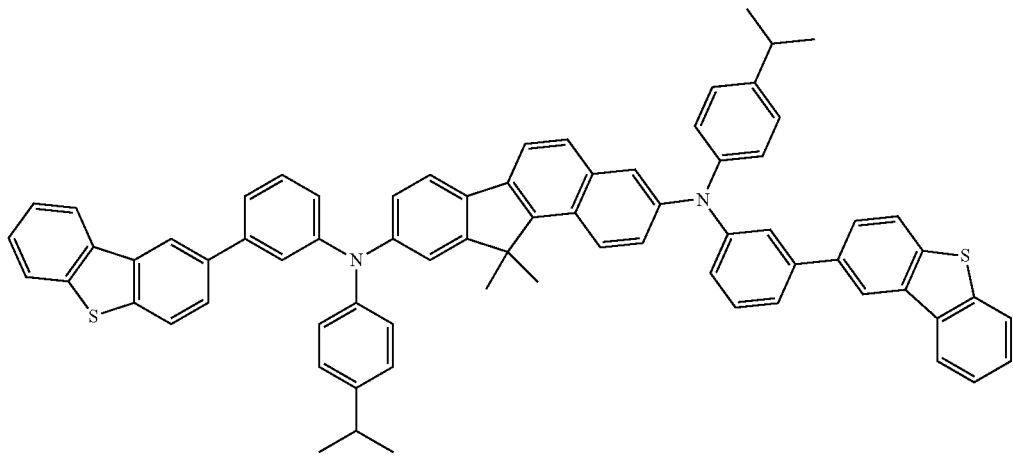
Compound 57
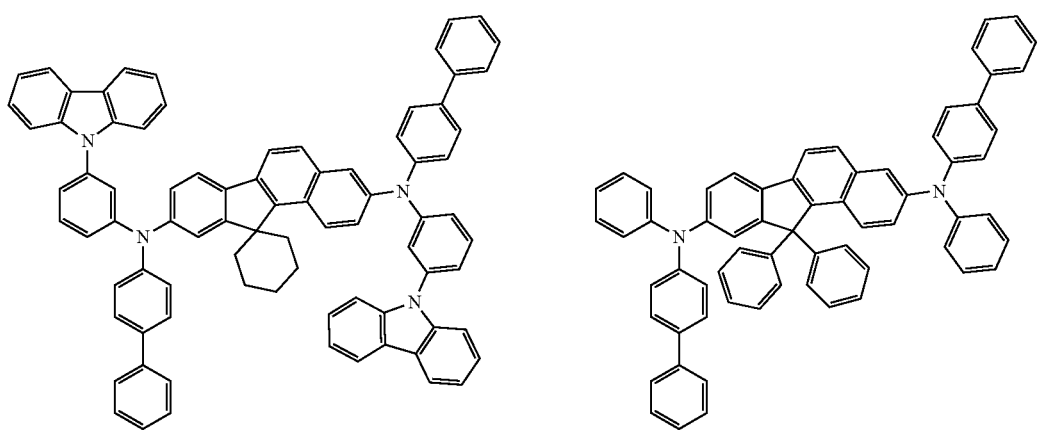
Compound 58
Compound 59
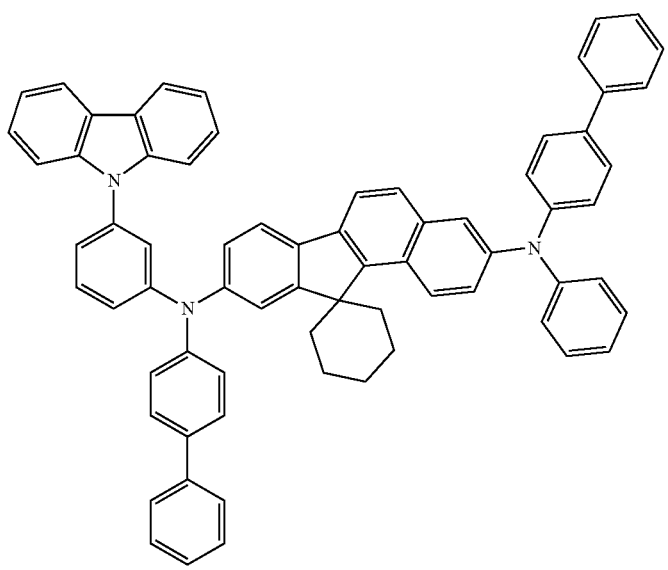

-continued

Compound 60

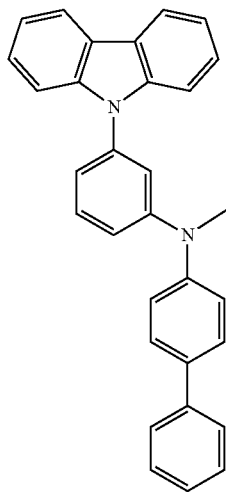

Compound 61

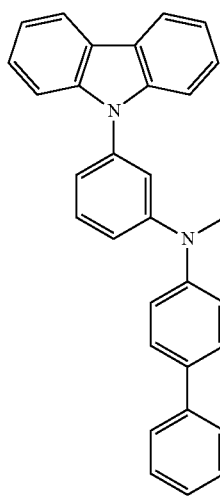

Compound 62

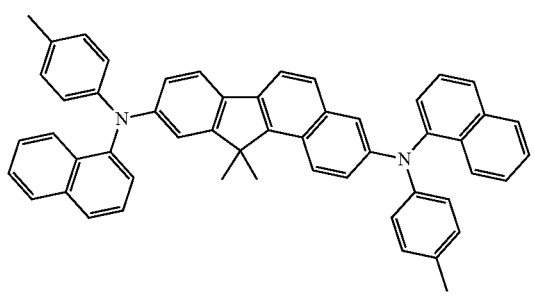

Compound 63

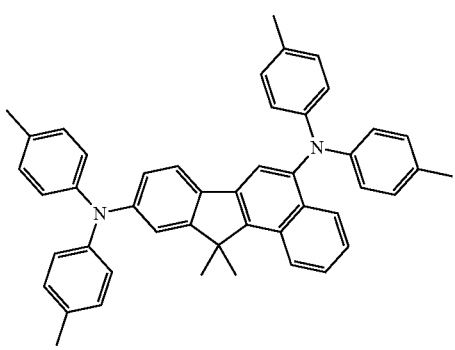

5. Devices

Organic electronic devices that may benefit from having one or more layers comprising the compounds having Formula I, Formula II, or Formula III described herein include, but are not limited to, (1) devices that convert electrical energy into radiation (e.g., a light-emitting diode, light emitting diode display, lighting device, luminaire, or diode laser), (2) devices that detect signals through electronics processes (e.g., photodetectors, photoconductive cells, photoresistors, photoswitches, phototransistors, phototubes, IR detectors, biosensors), (3) devices that convert radiation into electrical energy, (e.g., a photovoltaic device or solar cell), and (4) devices that include one or more electronic components that include one or more organic semi-conductor layers (e.g., a transistor or diode).

In some embodiments, the device includes a photoactive layer having a compound of Formula I.

In some embodiments, the device includes a photoactive layer having a compound of Formula I-a.

In some embodiments, the device includes a photoactive layer having a compound of Formula I-b. In some embodiments, the device includes a photoactive layer having a compound of Formula I-c.

In some embodiments, the device includes a photoactive layer having a compound of Formula I-d.

In some embodiments, the device includes a photoactive layer having a compound of Formula II.

In some embodiments, the device includes a photoactive layer having a compound of Formula II-a.

In some embodiments, the device includes a photoactive layer having a compound of Formula II-b.

In some embodiments, the device includes a photoactive layer having a compound of Formula II-c.

In some embodiments, the device includes a photoactive layer having a compound of Formula III.

In some embodiments, the device includes a photoactive layer having a compound of Formula III-a.

In some embodiments, the device includes a photoactive layer having a compound of Formula III-b.

In some embodiments, the device includes a photoactive layer having a compound of Formula III-c.

In some embodiments, the device includes a photoactive layer having a compound of Formula III-d.

In some embodiments, the device includes a photoactive layer having a compound of Formula III-e.

In some embodiments, the device includes an anode and a cathode with a photoactive layer therebetween, where the photoactive layer includes a compound having Formula I.

In some embodiments, the device includes an anode and a cathode with a photoactive layer therebetween, where the photoactive layer includes a compound having Formula I-a.

In some embodiments, the device includes an anode and a cathode with a photoactive layer therebetween, where the photoactive layer includes a compound having Formula I-b.

In some embodiments, the device includes an anode and a cathode with a photoactive layer therebetween, where the photoactive layer includes a compound having Formula I-c.

In some embodiments, the device includes an anode and a cathode with a photoactive layer therebetween, where the photoactive layer includes a compound having Formula I-d.

In some embodiments, the device includes an anode and a cathode with a photoactive layer therebetween, where the photoactive layer includes a compound having Formula II.

In some embodiments, the device includes an anode and a cathode with a photoactive layer therebetween, where the photoactive layer includes a compound having Formula II-a.

In some embodiments, the device includes an anode and a cathode with a photoactive layer therebetween, where the photoactive layer includes a compound having Formula II-b.

In some embodiments, the device includes an anode and a cathode with a photoactive layer therebetween, where the photoactive layer includes a compound having Formula II-c.

In some embodiments, the device includes an anode and a cathode with a photoactive layer therebetween, where the photoactive layer includes a compound having Formula III.

In some embodiments, the device includes an anode and a cathode with a photoactive layer therebetween, where the photoactive layer includes a compound having Formula III-a.

In some embodiments, the device includes an anode and a cathode with a photoactive layer therebetween, where the photoactive layer includes a compound having Formula III-b.

In some embodiments, the device includes an anode and a cathode with a photoactive layer therebetween, where the photoactive layer includes a compound having Formula III-c.

In some embodiments, the device includes an anode and a cathode with a photoactive layer therebetween, where the photoactive layer includes a compound having Formula III-d.

In some embodiments, the device includes an anode and a cathode with a photoactive layer therebetween, where the photoactive layer includes a compound having Formula III-e.

One illustration of an organic electronic device structure is shown in FIG. 1. The has a first electrical contact layer, an anode layer 110 and a second electrical contact layer, a cathode layer 160, and a photoactive layer 140 between them. Adjacent to the anode is a hole injection layer 120. Adjacent to the hole injection layer is a hole transport layer 130, comprising hole transport material. Adjacent to the cathode may be an electron transport layer 150, comprising an electron transport material. As an option, devices may use one or more additional hole injection or hole transport layers (not shown) next to the anode 110 and/or one or more additional electron injection or electron transport layers (not shown) next to the cathode 160. As a further option, devices may have an anti-quenching layer (not shown) between the photoactive layer 140 and the electron transport layer 150.

Layers 120 through 150, and any additional layers between them, are individually and collectively referred to as the active layers.

Figure 2:
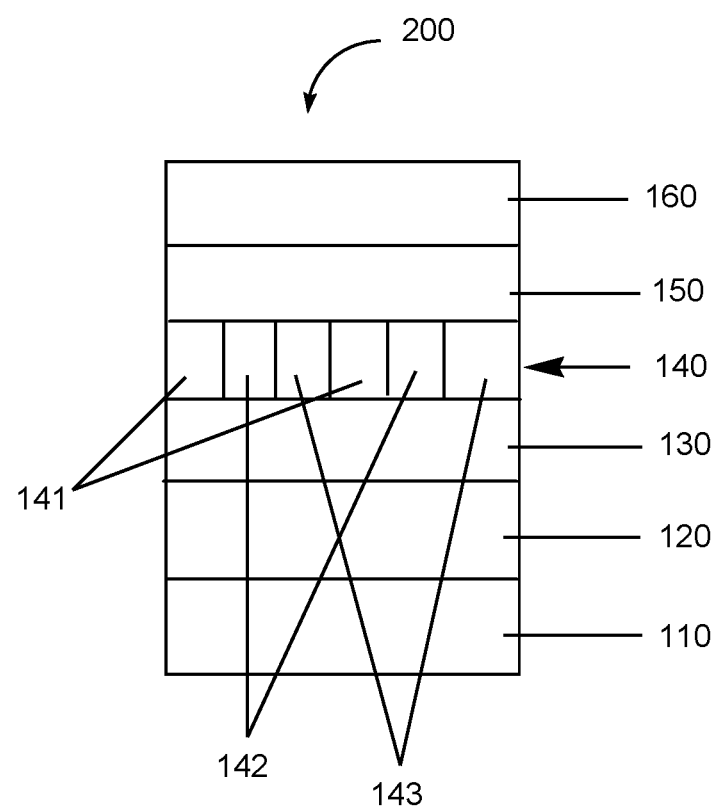
FIG. 2 includes another illustration of an organic light-emitting device.

In some embodiments, the photoactive layer is pixellated, as shown in FIG. 2. In device 200, layer 140 is divided into pixel or subpixel units 141, 142, and 143 which are repeated over the layer. Each of the pixel or subpixel units represents a different color. In some embodiments, the subpixel units are for red, green, and blue. Although three subpixel units are shown in the figure, two or more than three may be used.

In some embodiments, the different layers have the following range of thicknesses: anode 110, 500-5000 Å, in some embodiments, 1000-2000 Å; hole injection layer 120, 50-2000 Å, in some embodiments, 200-1000 Å; hole transport layer 130, 50-2000 Å, in some embodiments, 200-1000 Å; photoactive layer 140, 10-2000 Å, in some embodiments, 100-1000 Å; electron transport layer 150, 50-2000 Å, in some embodiments, 100-1000 Å; cathode 160, 200-10000 Å, in some embodiments, 300-5000 Å. The location of the electron-hole recombination zone in the device, and thus the emission spectrum of the device, can be affected by the relative thickness of each layer. The desired ratio of layer thicknesses will depend on the exact nature of the materials used.

In some embodiments, the compounds having Formula I, Formula I-a, Formula I-b, Formula I-c, Formula I-d, Formula II, Formula II-a, Formula II-b, Formula II-c, Formula III, Formula III-a, Formula III-b, Formula III-c, Formula III-d, or Formula III-e are useful as the emissive material in photoactive layer 140, having blue emission color. They can be used alone or as a dopant in a host material.

a. Photoactive Layer

In some embodiments, the photoactive layer includes a host material and a compound having Formula I, Formula I, Formula I-a, Formula I-b, Formula I-c, Formula I-d, Formula II, Formula II-a, Formula II-b, Formula II-c, Formula III, Formula III-a, Formula III-b, Formula III-c, Formula III-d, or Formula III-e as a dopant. In some embodiments, a second host material is present.

In some embodiments, the photoactive layer includes only a host material and a compound having Formula I, Formula I-a, Formula I-b, Formula I-c, Formula I-d, Formula II, Formula II-a, Formula II-b, Formula II-c, Formula III, Formula III-a, Formula III-b, Formula III-c, Formula III-d, or Formula III-e as a dopant. In some embodiments, minor amounts of other materials, are present so long as they do not significantly change the function of the layer.

In some embodiments, the photoactive layer includes only a first host material, a second host material, and a compound having Formula I, Formula I-a, Formula I-b, Formula I-c, Formula I-d, Formula II, Formula II-a, Formula II-b, Formula II-c, Formula III, Formula III-a, Formula III-b, Formula III-c, Formula III-d, or Formula III-e as a dopant. In some embodiments, minor amounts of other materials, are present so long as they do not significantly change the function of the layer.

The weight ratio of dopant to total host material is in the range of 5:95 to 70:30; in some embodiments, 10:90 to 20:80.

In some embodiments, the host material is selected from the group consisting of anthracenes, chrysenes, pyrenes, phenanthrenes, triphenylenes, phenanthrolines, naphthalenes, triazines, quinolines, isoquinolines, quinoxalines, phenylpyridines, benzodifurans, metal quinolinate complexes, indolocarbazoles, deuterated analogs thereof, and combinations thereof.

In some embodiments, the host material is a 9,10-diaryl anthracene compound or deuterated analog thereof.

In some embodiments, the host material is a chrysene derivative having one or two diarylamino substituents, or a deuterated analog thereof Any of the compounds of Formula I, Formula I-a, Formula I-b, Formula I-c, Formula I-d, Formula II, Formula II-a, Formula II-b, Formula II-c, Formula III, Formula III-a, Formula III-b, Formula III-c, Formula III-d, or Formula III-e represented by the embodiments, specific embodiments, specific examples, and combination of embodiments discussed above can be used in the photoactive layer.

b. Other Device Layers

The other layers in the device can be made of any materials which are known to be useful in such layers.

The anode 110 is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode may also be made of an organic material such as polyaniline as described in "Flexible light-emitting diodes made from soluble conducting polymer," Nature vol. 357, pp 477 479 (11 Jun. 1992). At least one of the anode and cathode should be at least partially transparent to allow the generated light to be observed.

The hole injection layer 120 includes hole injection material and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like.

The hole injection layer can include charge transfer compounds, and the like, such as copper phthalocyanine and the tetrathiafulvalene-tetracyanoquinodimethane system (TTF-TCNQ).

In some embodiments, the hole injection layer includes at least one electrically conductive polymer and at least one fluorinated acid polymer.

In some embodiments, the hole injection layer is made from an aqueous dispersion of an electrically conducting polymer doped with a colloid-forming polymeric acid. Such materials have been described in, for example, published U.S. patent applications US 2004/0102577, US 2004/0127637, US 2005/0205860, and published PCT application WO 2009/018009.

Examples of hole transport materials for layer 130 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino) phenyl]cyclohexane (TAPC), N,N'-bis(4-methylphenyl)-N,N'-bis(4-ethylphenyl)-[1,1'-(3,3'-dimethyl) biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino) benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis(naphthalen-1-yl)-N,N'-bis-(phenyl)benzidine (□-NPB), and porphyrinic compounds, such as copper phthalocyanine. In some embodiments, the hole transport layer includes a hole transport polymer. In some embodiments, the hole transport polymer is a distyrylaryl compound. In some embodiments, the aryl group has two or more fused aromatic rings. In some embodiments, the aryl group is an acene. The term "acene" as used herein refers to a hydrocarbon parent component that contains two or more ortho-fused benzene rings in a straight linear arrangement. Other commonly used hole transporting polymers are polyvinylcarbazole, (phenylmethyl)-polysilane, and polyaniline. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable.

In some embodiments, the hole transport layer further includes a p-dopant. In some embodiments, the hole transport layer is doped with a p-dopant. Examples of p-dopants include, but are not limited to, tetrafluorotetracyanoquinodimethane (F4-TCNQ) and perylene-3,4,9,10-tetracarboxylic-3,4,9,10-dianhydride (PTCDA).

In some embodiments, more than one hole transport layer is present (not shown).

Examples of electron transport materials which can be used for layer 150 include, but are not limited to, metal chelated oxinoid compounds, including metal quinolate derivatives such as tris(8-hydroxyquinolato)aluminum (AlQ), bis(2-methyl-8-quinolinolato)(p-phenylphenolato) aluminum (BAlq), tetrakis-(8-hydroxyquinolato)hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri (phenyl-2-benzimidazole)benzene (TPBI); quinoxaline derivatives such as 2,3-bis(4-fluorophenyl)quinoxaline; fluoranthene derivatives, such as 3-(4-(4-methylstyryl)phenyl-p-tolylamino)fluoranthene; phenanthrolines such as 4,7-diphenyl-1,10-phenanthroline (DPA) and 2,9-dimethyl-4,7-diphenyl-1,10-phenanthroline (DDPA); and mixtures thereof. In some embodiments, the electron transport layer further includes an n-dopant. N-dopant materials are well known. The n-dopants include, but are not limited to, Group 1 and 2 metals; Group 1 and 2 metal salts, such as LiF, CsF, and $Cs_2CO_3$; Group 1 and 2 metal organic compounds, such as Li quinolate; and molecular n-dopants, such as leuco dyes, metal complexes, such as $W_2(hpp)_4$ where hpp=1,3,4,6,7,8-hexahydro-2H-pyrimido-[1,2-a]-pyrimidine and cobaltocene, tetrathianaphthacene, bis(ethylenedithio)tetrathiafulvalene, heterocyclic radicals or diradicals, and the dimers, oligomers, polymers, dispiro compounds and polycycles of heterocyclic radical or diradicals.

In some embodiments, an anti-quenching layer may be present between the photoactive layer and the electron transport layer to prevent quenching of blue luminance by the electron transport layer. To prevent energy transfer quenching, the singlet energy of the anti-quenching material has to be higher than the singlet energy of the blue emitter. To prevent electron transfer quenching, the LUMO level of the anti-quenching material has to be shallow enough (with respect to the vacuum level) such that electron transfer between the emitter exciton and the anti-quenching material is endothermic. Furthermore, the HOMO level of the anti-quenching material has to be deep enough (with respect to the vacuum level) such that electron transfer between the emitter exciton and the anti-quenching material is endothermic. In general, anti-quenching material is a large band-gap material with high singlet and triplet energies.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used.

Alkali metal-containing inorganic compounds, such as LiF, CsF, $Cs_2O$ and $Li_2O$, or Li-containing organometallic compounds can also be deposited between the organic layer 150 and the cathode layer 160 to lower the operating voltage. This layer, not shown, may be referred to as an electron injection layer.

It is known to have other layers in organic electronic devices. For example, there can be a layer (not shown) between the anode 110 and hole injection layer 120 to control the amount of positive charge injected and/or to provide band-gap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

c. Device Fabrication

The device layers can be formed by any deposition technique, or combinations of techniques, including vapor deposition, liquid deposition, and thermal transfer.

In some embodiments, the device is fabricated by liquid deposition of the hole injection layer, the hole transport layer, and the photoactive layer, and by vapor deposition of the anode, the electron transport layer, an electron injection layer and the cathode.

The hole injection layer can be deposited from any liquid medium in which it is dissolved or dispersed and from which it will form a film. In some embodiments, the liquid medium includes only one or more organic solvents. In some embodiments, minor amounts of other materials are present, so long as they do not substantially affect the liquid medium.

In some embodiments, the liquid medium includes only water or includes only water and an organic solvent. In some embodiments, minor amounts of other materials are present, so long as they do not substantially affect the liquid medium.

The hole injection material is present in the liquid medium in an amount from 0.5 to 10 percent by weight.

In some embodiments, the hole injection layer is formed by any continuous or discontinuous liquid deposition technique. In some embodiments, the hole injection layer is applied by spin coating. In some embodiments, the hole injection layer is applied by ink jet printing. In some embodiments, the hole injection layer is applied by continuous nozzle printing. In some embodiments, the hole injection layer is applied by slot-die coating. After liquid deposition, the liquid medium can be removed in air, in an inert atmosphere, or by vacuum, at room temperature or with heating.

In some embodiments, the hole transport layer is formed by liquid deposition of hole transport material in a liquid medium. The liquid medium is one in which the hole transport material is dissolved or dispersed and from which it will form a film. In some embodiments, the liquid medium includes one or more organic solvents. In some embodiments, the liquid medium includes water or water and an organic solvent. In some embodiments, the organic solvent is an aromatic solvent. In some embodiments, the organic liquid is selected from chloroform, dichloromethane, chlorobenzene, dichlorobenzene, toluene, xylene, mesitylene, anisole, and mixtures thereof. The hole transport material can be present in the liquid medium in a concentration of 0.2 to 2 percent by weight. The hole transport layer can be applied by any continuous or discontinuous liquid deposition technique. In some embodiments, the hole transport layer is applied by spin coating. In some embodiments, the hole transport layer is applied by ink jet printing. In some embodiments, the hole transport layer is applied by continuous nozzle printing. In some embodiments, the hole transport layer is applied by slot-die coating. After liquid deposition, the liquid medium can be removed in air, in an inert atmosphere, or by vacuum, at room temperature or with heating.

In some embodiments, the photoactive layer is formed by vapor deposition. Such techniques are well known in the art.

In some embodiments, the photoactive layer is formed by liquid deposition of the photoactive material and one or more host materials in a liquid medium. The liquid medium is one in which the materials of the photoactive layer are dissolved or dispersed and from which it will form a film. In some embodiments, the liquid medium includes one or more organic solvents. In some embodiments, minor amounts of additional materials are present so long as they do not substantially affect the function of the photoactive layer.

Suitable classes of solvents include, but are not limited to, aliphatic hydrocarbons (such as decane and hexadecane), halogenated hydrocarbons (such as methylene chloride, chloroform, chlorobenzene, and perfluoroheptane), aromatic hydrocarbons (such as non-substituted and alkyl- and alkoxy-substituted toluenes and xylenes), aromatic ethers (such as anisole and dibenzyl ether), heteroaromatics (such as pyridine) polar solvents (such as tetrahydropyran ("THP"), dimethylacetamide ("DMAC") and N-methyl pyrrolidone ("NMP")), esters (such as ethylacetate, propylene carbonate, methyl benzoate), alcohols and glycols (such as isopropanol and ethylene glycol), glycol ethers and derivatives (such as propylene glycol methyl ether and propylene glycol methyl ether acetate), and ketones (such as cyclopentanone and diisobutyl ketone).

The photoactive material can be present in the liquid medium in a concentration of 0.2 to 2 percent by weight. Other weight percentages of photoactive material may be used depending upon the liquid medium. The photoactive layer can be applied by any continuous or discontinuous liquid deposition technique. In some embodiments, the photoactive layer is applied by spin coating. In some embodiments, the photoactive layer is applied by ink jet printing. In some embodiments, the photoactive layer is applied by continuous nozzle printing. In some embodiments, the photoactive layer is applied by slot-die coating. After liquid deposition, the liquid medium can be removed in air, in an inert atmosphere, or by vacuum, at room temperature or with heating.

The electron transport layer can be deposited by any vapor deposition method. In some embodiments, it is deposited by thermal evaporation under vacuum.

The electron injection layer can be deposited by any vapor deposition method. In some embodiments, it is deposited by thermal evaporation under vacuum.

The cathode can be deposited by any vapor deposition method. In some embodiments, it is deposited by thermal evaporation under vacuum.

EXAMPLES

The concepts described herein will be further described in the following examples, which do not limit the scope of the invention described in the claims.

Synthesis Example 1

This example illustrates the preparation of compounds having Formula I: Compound 3, Compound 1, and Compound 37.

Synthesis of N-[3-(3,6-diphenyl-9H-carbazol-9-yl)phenyl]biphenyl-4-amine

To a 500 mL round bottom flask under nitrogen were added 4-bromobiphenyl (2.70 g, 11.6 mmol), 3-(3,6-diphenyl-9H-carbazol-9-yl)aniline (5.00 g, 12.2 mmol), tris(dibenzylideneacetone) dipalladium(0) (212 mg, 0.232 mmol), tri-tert-butylphosphine (93.9 mg, 0.464 mmol), and toluene (120 mL). Sodium tert-butoxide (1.23 g, 12.7 mmol) was then added and the reaction stirred at room temperature overnight. The solvent was removed and the material was separated by column chromatography using silica gel and 1:2 chloroform in hexanes. Fractions were dried to yield a thick yellow oil, 5.71 g (87%).

Synthesis of N,N'-di(biphenyl-4-yl)-N,N'-bis[3-(3,6-diphenyl-9H-carbazol-9-yl)phenyl]-7,7-dimethyl-7H-benzo[c]fluorene-5,9-diamine To a 500 mL round bottom flask under nitrogen were added 5,9-dibromo-7,7-dimethyl-7H-benzo[c]fluorene (1.93 g, 4.81 mmol), N-[3-(3,6-diphenyl-9H-carbazol-9-yl)phenyl]biphenyl-4-amine (5.68 g, 10.1 mmol), tris(dibenzylideneacetone) dipalladium(0) (88.0 mg, 0.0961 mmol), tri-tert-butylphosphine (38.9 mg, 0.192 mmol), and toluene (100 mL). Sodium tert-butoxide (1.02 g, 10.6 mmol) was then added and the reaction stirred at 80° C. overnight. Solvent was removed and the resultant material was separated by column chromatography using silica gel and 2:3 chloroform in hexanes. Fractions were dried and recrystallized from 2:1 dichloromethane and acetonitrile. Yield 4.01 g (61%) yellow crystals.

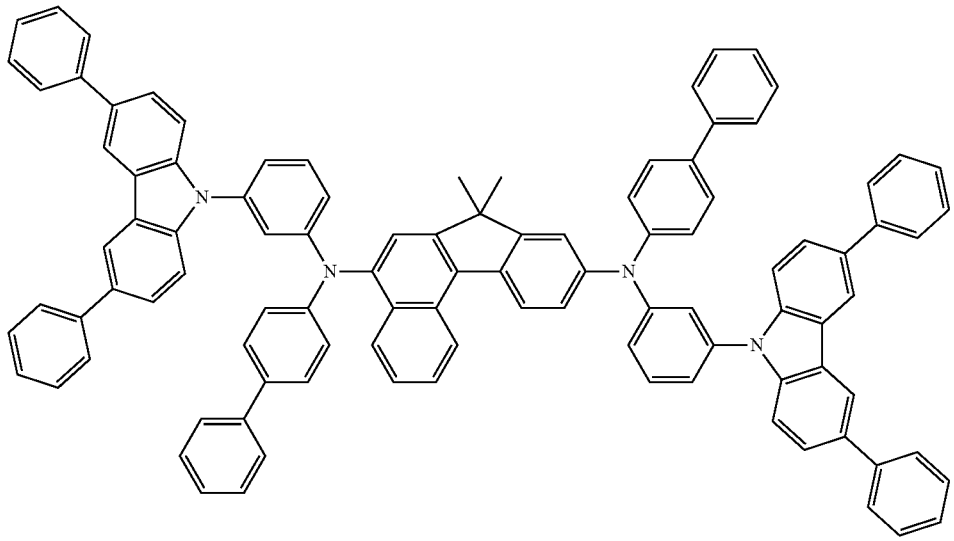

Compound 3

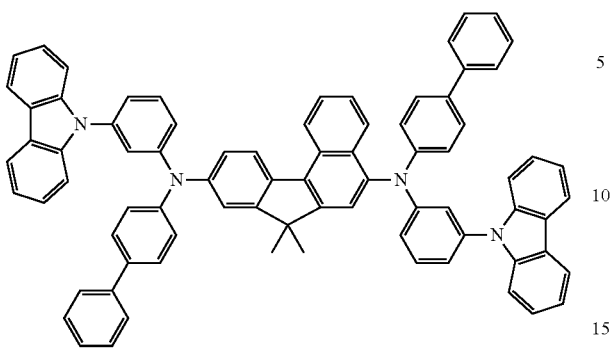

Compound 1

Compound 1 can be made in an analogous manner to Compound 3, starting with N-[3-(9H-carbazol-9-yl)phenyl]biphenyl-4-amine.
Compound 37 with 68% deuteration.

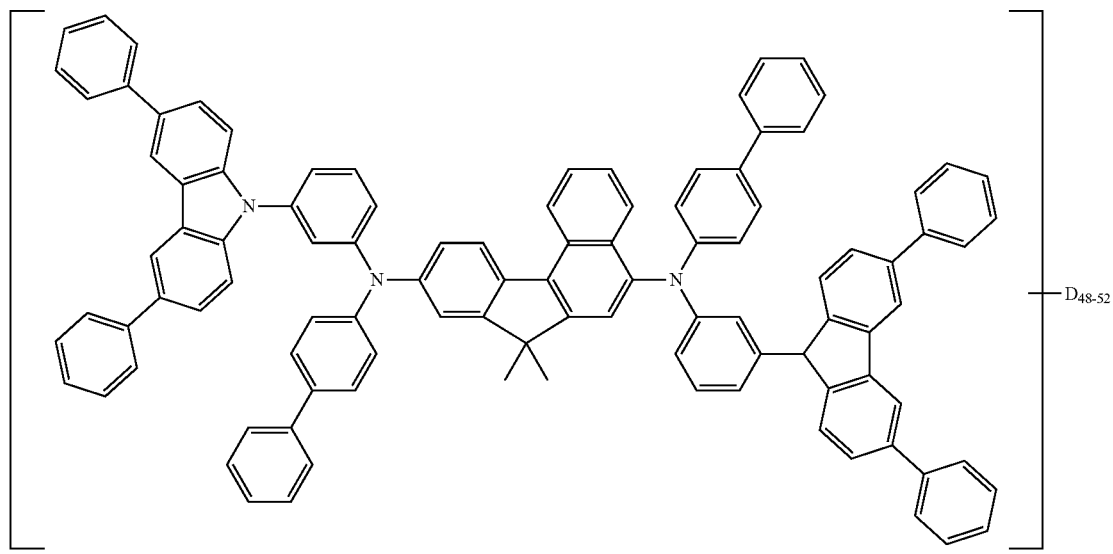

Compound 37 can be made by deuterating Compound 3.

Synthesis of D50-N,N'-di(biphenyl-4-yl)-N,N'-bis[3-(3,6-diphenyl-9H-carbazol-9-yl)phenyl]-7,7-dimethyl-7H-benzo[c]fluorene-5,9-diamine To a 50 mL round bottom flask under nitrogen were added N,N'-di(biphenyl-4-yl)-N,N'-bis[3-(3,6-diphenyl-9H-carbazol-9-yl)phenyl]-7,7-dimethyl-7H-benzo[c]fluorene-5,9-diamine (1.38 g, 1.01 mmol), benzene-d6 (17 mL), the mixture was stirred at ambient temperature for 10 min. Triflic Acid-d (1.52 g, 10.10 mmol) was added slowly. The reaction was then heated to 50 $^3$C and stirred under nitrogen for 18 hours. The reaction was quenched with 10 wt % sodium carbonate in D2O. The organic layer was separated and dried with magnesium sulfate. After filtering, the solvent was removed and the residue was purified on Silica gel column eluted with hexane/chloroform. The product containing fractions were collected and the solvent was removed. Crystallization from DCM/acetonitrile gave 1.19 g product in 99% purity. UPLC/MS analysis indicated that about 49 out of 72 protons (68%) had been exchanged.

Synthesis Example 2

This example illustrates the preparation of a compound having Formula I, Compound 5.

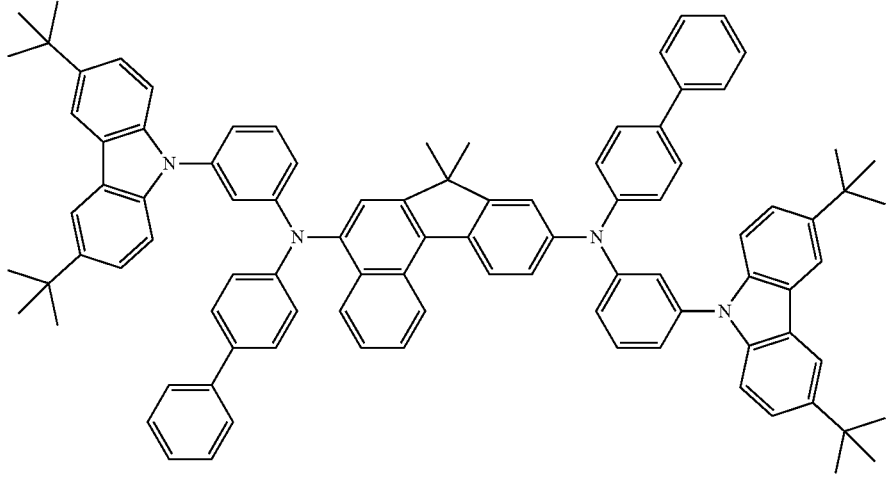 [SMILES: CC(C)(C)c1ccc2c(c1)c1cc(C(C)(C)C)ccc1n2-c1cccc(N(c2ccc(-c3ccccc3)cc2)c2ccc3c(c2)C(C)(C)c2cc(N(c4ccc(-c5ccccc5)cc4)c4cccc(-n5c6ccc(C(C)(C)C)cc6c6cc(C(C)(C)C)ccc65)c4)c4ccccc4c2-3)c1]

Synthesis of N-[3-(3,6-di-tert-butyl-9H-carbazol-9-yl)phenyl]biphenyl-4-amine To a 500 mL round bottom flask under nitrogen were added 4-bromobiphenyl (2.99 g, 12.8 mmol), 3-(3,6-di-tert-butyl-9H-carbazol-9-yl)aniline (5.00 g, 13.5 mmol), tris(dibenzylideneacetone) dipalladium(0) (235 mg, 0.257 mmol), tri-tert-butylphosphine (104 mg, 0.514 mmol), and toluene (135 mL). Sodium tert-butoxide (1.36 g, 14.1 mmol) was then added and the reaction stirred at room temperature overnight. The solvent was removed and the resultant material was separated by column chromatography using silica gel and 1:2 chloroform in hexanes. Fractions were dried to yield a thick yellow oil, 6.40 g (95%).

Synthesis of N,N'-di(biphenyl-4-yl)-N,N'-bis[3-(3,6-di-tert-butyl-9H-carbazol-9-yl)phenyl]-7,7-dimethyl-7H-benzo[c]fluorene-5,9-diamine To a 500 mL round bottom flask under nitrogen were added 5,9-dibromo-7,7-dimethyl-7H-benzo[c]fluorene (2.34 g, 5.83 mmol), N-[3-(3,6-di-tert-butyl-9H-carbazol-9-yl)phenyl]biphenyl-4-amine (6.40 g, 12.2 mmol), tris(dibenzylideneacetone) dipalladium(0) (107 mg, 0.117 mmol), tri-tert-butylphosphine (47.2 mg, 0.233 mmol), and toluene (120 mL). Sodium tert-butoxide (1.23 g, 12.8 mmol) was then added and the reaction stirred at 80° C. overnight. The solvent was removed and the resulting material was separated by column chromatography using silica gel and 2:3 chloroform in hexanes. Fractions were dried and passed through a basic alumina plug with 1:5 dichloromethane in hexanes. Fractions were dried and precipitated from dichloromethane into methanol. Yield 2.70 g (36%) yellow powder.

Synthesis Example 3

This example illustrates the preparation of a compound having Formula I, Compound 2.

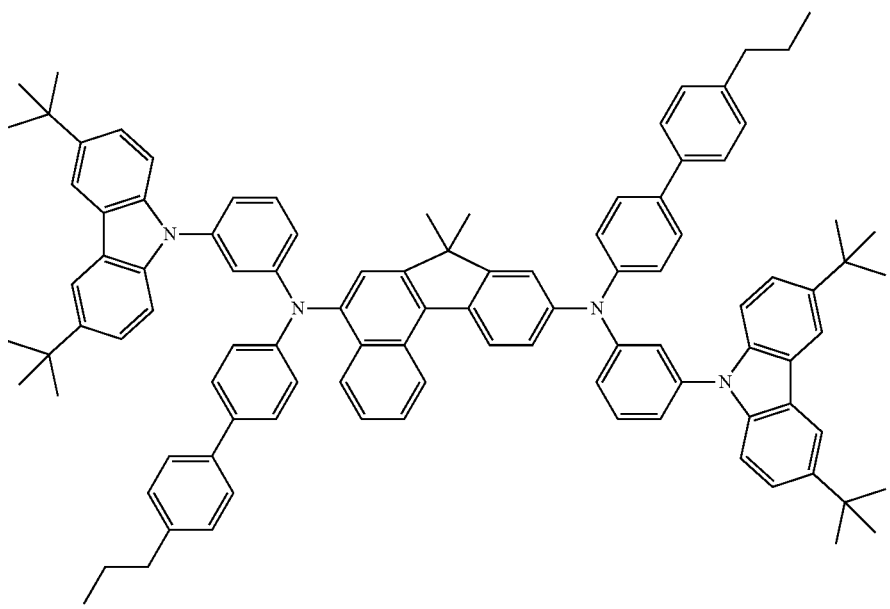 [SMILES: CCCc1ccc(-c2ccc(N(c3cccc(-n4c5ccc(C(C)(C)C)cc5c5cc(C(C)(C)C)ccc54)c3)c3ccc4c(c3)C(C)(C)c3cc(N(c5ccc(-c6ccc(CCC)cc6)cc5)c5cccc(-n6c7ccc(C(C)(C)C)cc7c7cc(C(C)(C)C)ccc76)c5)c5ccccc5c3-4)cc2)cc1]

Synthesis of N-(3-(3,6-di-tert-butyl-9H-carbazol-9-yl)phenyl)-4'-propyl-[1,1'-biphenyl]-4-amine 9-(3-Bromophenyl)-3,6-di-tert-butyl-9H-carbazole (30 g, 69.1 mmol), 4'-propyl-[1,1'-biphenyl]-4-amine (19 g, 89.8 mmol), tris (dibenzylideneacetone) dipalladium (0.32 g, 0.3 mmol), tri-tert-butylphosphine (0.14 g, 0.7 mmol) and sparged anhydrous toluene (325 ml) were taken in the 500 ml flask under nitrogen and stirred for 5 min. To this solution sodium t-butoxide (7.3 g, 76 mmol) was added in small portions with stirring at room temp and the reaction was allowed to stir until deemed complete when no more carbazole starting material was observed.

The reaction was quenched with 100 ml water and allowed to stir for 15 min. The reaction mixture was taken into a separatory funnel and the aqueous phase drained. The organic layer was washed twice more with 100 ml DI water.

The resulting dark brown solution was concentrated to ~1/3 its volume, diluted with hexanes and passed through a plug of dry silica to remove catalyst. The silica gel was rinsed with 600 ml of 50% toluene-hexane to remove product. The product started precipitating out upon sitting and was collected by filtration, and washed with methanol. On drying this yielded 30.2 g (77.4%) of off-white solid as crop1.

Synthesis of N5,N9-bis(3-(3,6-di-tert-butyl-9H-carbazol-9-yl)phenyl)-7,7-dimethyl-N5,N9-bis(4'-propyl-[1,1'-biphenyl]-4-yl)-7H-benzo[c]fluorene-5,9-diamine 5,9-Dibromo-7,7-dimethylbenzofluorene (8.72 g, 21.7 mmol), N-(3-(3,6-di-tert-butyl-9H-carbazol-9-yl)phenyl)-4'-propyl-[1,1'-biphenyl]-4-amine (25 g, 44.3 mmol), tris (dibenzylideneacetone) dipalladium (0.203 g, 0.2 mmol), tri-tert-butylphosphine (0.090 g, 0.4 mmol) and sparged anhydrous toluene (175 ml) were taken in the 500 ml flask under nitrogen and stirred for 5 min. To this solution sodium t-butoxide (4.47 g, 46.5 mmol) was added in small portions with stirring at room temperature. The resulting solution was warmed to 60° C. and allowed to stir until no more benzofluorene starting material was observed.

The reaction was quenched with 50 ml water and allowed to stir for 10 min. The reaction mixture was taken in a separatory funnel and the aqueous phase drained. The organic layer was washed twice more with 50 ml DI water.

The resulting dark brown solution was concentrated to yield crude product. Material was further purified via chromatography over silica gel using a toluene-hexane gradient as eluent. Product containing clean fractions were combined and concentrated. Process was repeated until absolutely clean product was achieved. The resulting concentrate was treated with methanol to yield the product as a solid which was collected via filtration. On drying this yielded 17.9 g (61%) of a pale yellow solid as the desired product.

Synthesis Example 4

This example illustrates the preparation of a compound having Formula I, Compound 4.

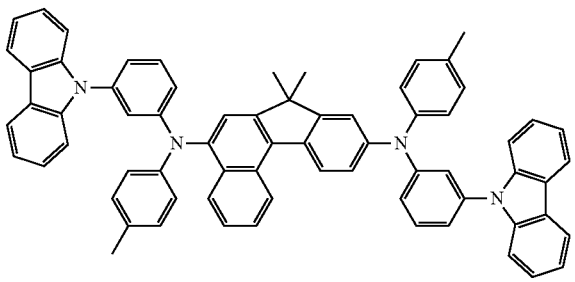 [SMILES: CC1(C)c2cc(N(c3ccccc3)c3cccc(-n4c5ccccc5c5ccccc54)c3)ccc2-c2c1cc(N(c1ccccc1)c1cccc(-n3c4ccccc4c4ccccc43)c1)c1ccccc21]

Synthesis of 3-(9H-carbazol-9-yl)-N-(4-methylphenyl)aniline

4-Bromotoluene (2.34 g, 13.7 mmol), 3-(9H-carbazol-9-yl)aniline (3.53 g, 13.7 mmol), tris (dibenzylideneacetone) dipalladium (250 mg, 0.27 mmol), tri-tert-butylphosphine (111 mg, 0.55 mmol) and anhydrous toluene (95 ml) were taken in the 250 ml flask under nitrogen and stirred for 5 min. To this solution sodium t-butoxide (1.44 g, 15.0 mmol) was added in small portions with stirring at room temp. The reaction was allowed to stir at room temperature overnight.

The reaction showed no remaining bromotoluene by UPLC analysis. The mixture was passed through a column and eluted with toluene. The solvent was removed, and the resulting material was dissolved in DCM/hexane (1/9 30 mL) and passed through a short Silica gel column, eluted with hexane first, then with DCM/hexane gradient. Fractions were identified by TLC, collected, and the solvent was removed by rotary evaporation. The product was obtained as a clear thick oil, yield, 3.84 g (81%) in 99.1% purity by UPLC analysis.

Synthesis of N,N'-bis[3-(9H-carbazol-9-yl)phenyl]-7,7-dimethyl-N,N'-bis(4-methylphenyl)-7H-benzo[c]fluorene-5,9-diamine 5,9-Dibromo-7,7-dimethylbenzofluorene (2.17 g, 5.40 mmol), 3-(9H-carbazol-9-yl)-N-(4-methylphenyl)aniline (3.84 g, 11.02 mmol), tris (dibenzylideneacetone) dipalladium (99 mg, 0.11 mmol), tri-tert-butylphosphine (45 mg, 0.22 mmol) and anhydrous toluene (100 ml) were taken in the 250 ml flask under nitrogen and stirred for 5 min. To this solution sodium t-butoxide (1.14 g, 11.9 mmol) was added in small portions with stirring at room temperature and the resulting solution allowed to stir until no more dibromobenzofluorene starting material was observed. The solvent was removed and the resulting material was separated by column chromatography using silica gel and 2:3 chloroform in hexanes. Fractions were dried and passed through a basic alumina plug with 1:5 dichloromethane in hexanes. Fractions were dried and precipitated from dichloromethane into methanol. Yield 2.55 g (50%) yellow powder.

Synthesis Example 5

This example illustrates the preparation of a compound having Formula I, Compound 6.

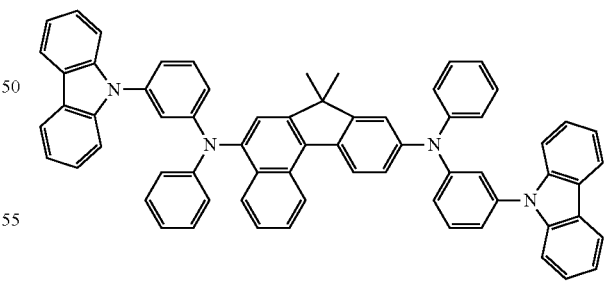

Synthesis of 3-(9H-carbazol-9-yl)-N-phenylaniline

To a 1 L round bottom flask under nitrogen were added 9-(3-bromophenyl)-9H-carbazole (14.5 g, 40.9 mmol), aniline (4.00 g, 42.9 mmol), tris(dibenzylideneacetone) dipalladium(0) (749 mg, 0.818 mmol), tri-tert-butylphosphine (331 mg, 1.64 mmol), and toluene (430 mL). Sodium tert-butoxide (4.32 g, 45.0 mmol) was then added and the reaction stirred at room temperature overnight. The solvent was removed and the resulting material was separated by column chromatography using silica gel and 1:2 chloroform in hexanes. Fractions were dried to yield a thick yellow oil, 12.3 g (90%).

Synthesis of N,N'-bis[3-(9H-carbazol-9-yl)phenyl]-7,7-dimethyl-N,N'-diphenyl-7H-benzo[c]fluorene-5,9-diamine To a 500 mL round bottom flask under nitrogen were added 5,9-dibromo-7,7-dimethyl-7H-benzo[c]fluorene (3.64 g, 9.06 mmol), 3-(9H-carbazol-9-yl)-N-phenylaniline (6.70 g, 19.0 mmol), tris(dibenzylideneacetone) dipalladium(0) (166 mg, 0.181 mmol), tri-tert-butylphosphine (73.3 mg, 0.362 mmol), and toluene (120 mL). Sodium tert-butoxide (1.92 g, 19.9 mmol) was then added and the reaction stirred at 80° C. overnight. The solvent was removed and the resulting material was separated by column chromatography using silica gel and 1:3 chloroform in hexanes. Fractions were dried and passed through a basic alumina plug with 1:5 dichloromethane in hexanes. Fractions were dried and precipitated from dichloromethane into methanol. Yield 814 mg (10%) yellow powder.

Synthesis Example 6

This example illustrates the preparation of a compound having Formula III-b, Compound 61.

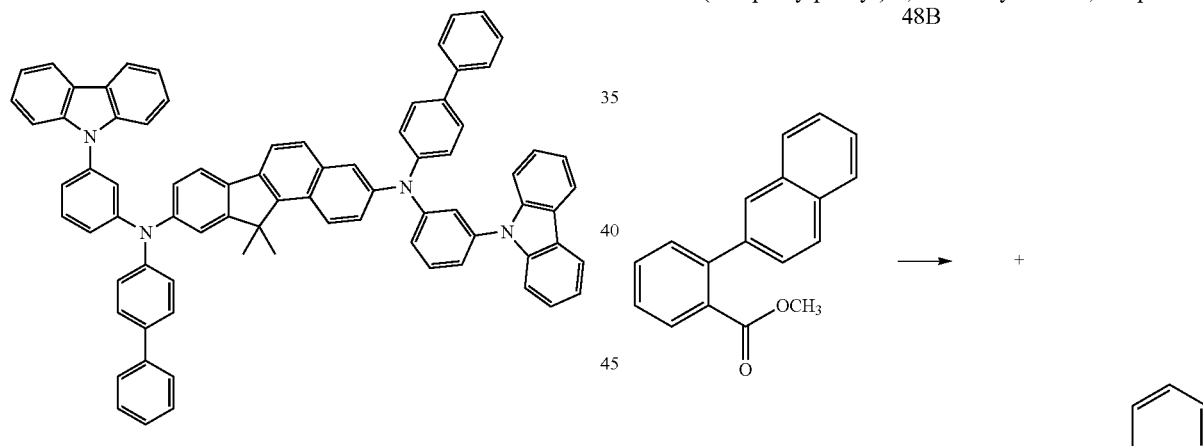

Synthesis of 2-(2-naphthyl)-methylbenzoate—Cmpd 48A

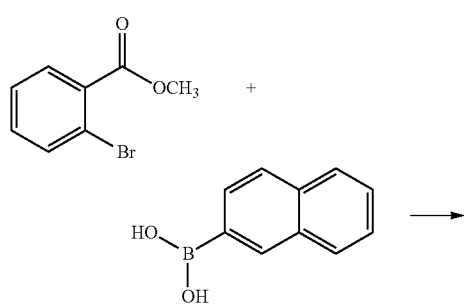

48A

Methyl-2-bromobenzoate (50 g, 0.2325 mol), naphthalene-2-boronic acid (50 g, 0.2907 mol), 400 ml water, potassium carbonate (102.5 g, 0.7416 mol) and 1 liter monoglyme were combined and sparged with nitrogen for 40 minutes. Tetrakistriphenylphosphine Pd(0) (10.0 g, 8.65 mmol) was quickly added and the mixture refluxed overnight. Upon completion, the mixture was concentrated and separated using a dichloromethane (DCM)/water partition. The DCM solution was preabsorbed 5:1 onto 300 grams of neutral-alumina. and chromatographed on a silica column with 10% DCM in hexanes followed by 50% DCM in hexanes. Eluted fractions were concentrated by rotary evaporation to 58.76 grams of white solid, 96% yield Cmpd 48A.

Synthesis of 2-(2-naphthylphenyl)-1,1-dimethylethanol, Cmpd 48B

48B (38 g, 0.3073 mol) Cmpd 48A from above, 300 mL anhydrous THF were combined and cooled using an ice/water bath. 116 ml of 3M methylmagnesium bromide in ether was added over one hour dropwise keeping the mixture under 20° C. The reaction was allowed to stir one hour. Upon removal of the cooling bath, the pot warmed to 28° C. 200 ml of 10% ammonium chloride was added through the same addition funnel slowly followed by 150 mL toluene. The toluene layer was separated and the aqueous layer was washed with more toluene. The toluene layers and washings were combined and concentrated to 37.3 grams of yellow oil. of Cmpd 48B Synthesis of Benzofluorene Core Materials Cmpds 48C1 and 48C2

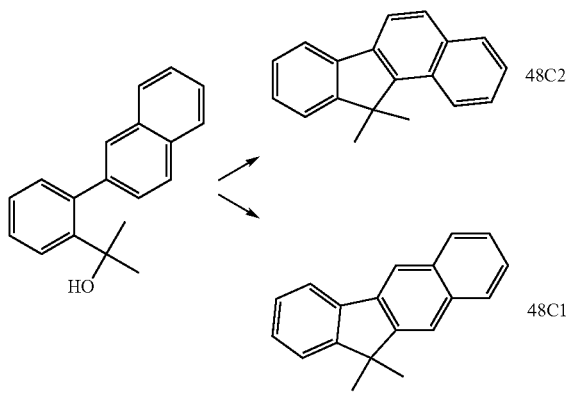

Trifluoroacetic acid (431 g, 2.265 mol) and dichloromethane, 890 mL were combined and sparged with nitrogen. Added 37.2 g of Cmpd 48B from above in 170 mL dichloromethane dropwise over an hour. 50% NaOH solution was slowly added to neutralize the acid. The organic layer was separated and preabsorbed onto 136 grams of silica. Performed column chromatography with a 4"×10" silica column with 100% hexanes followed by 1% DCM in hexanes increasing gradient to 4% DCM in hexanes. The leading spot of four was the intended product concentrated to 21.5 grams (61%) of white solid as a mixture of Cmpds 48C1 and 48C2.

Synthesis of dibromo-7,7-dimethyl-7H-benzofluorenes

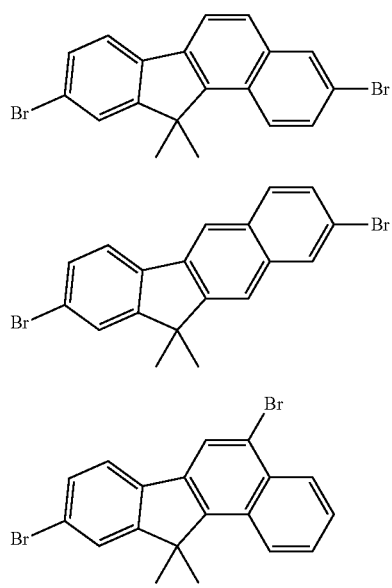

A mixture of cmpds 48C1 and 48C2 above (9.68 g, 0.0396 mol), 80 mL dichloromethane, 55 mL acetic acid and zinc chloride (13.66 g, 0.1 mol) was stirred and cooled to −6° C. A solution of 150 mL dichloromethane, 5 mL acetic acid and trimethylammonium benzyltribromide (34.11 g, 0.0396 mol) was added dropwise over 90 minutes. A further, 20 mL dichloromethane and acetic acid, 20 mL was added to the pot during the addition. The reaction was stirred overnight and slowly warmed to ambient temperature. Sodium hydrogen sulfite was added until the color was eliminated and the solution was then evaporated to dryness. The solid was partitioned with dichloromethane and water and neutralized with potassium carbonate. The organic layer was concentrated to 17.8 g of brown solid which was pre-absorbed from DCM onto 35 g of silica gel and then chromatographed on silica eluting with hexanes. The first fraction, was concentrated to 9.4 g white solid which was a mixture of compounds 48D1, 48D2, and 48D3—rich in compound 48D1, while the second fraction was concentrated to 4.6 grams white solid which was pure 48D3 (confirmed by x-ray single crystallography). Compound 48D1 was isolated by careful chromatography of the mixture (compounds 48D1, 48D2, and 48D3) using hexane eluent on a silica gel column.

Synthesis of 3-(9H-carbazol-9-yl)-N-4-biphenyl-aniline

To a 1 L round bottom flask under nitrogen were added 9-(3-bromophenyl)-9H-carbazole (14.5 g, 40.9 mmol), 4-aminobiphenyl (7.25 g, 42.9 mmol), tris(dibenzylideneacetone) dipalladium(0) (749 mg, 0.818 mmol), tri-tert-butylphosphine (331 mg, 1.64 mmol), and toluene (430 mL). Sodium tert-butoxide (4.32 g, 45.0 mmol) was then added and the reaction stirred at room temperature overnight. The solvent was removed and the material was separated by column chromatography using silica gel eluting with 1:2 chloroform in hexanes. Fractions were dried to yield a yellow solid, 12.8 g Synthesis of Compound 61

To a 500 mL round bottom flask under nitrogen were added cmpd 48D1 above (3.64 g, 9.06 mmol), 3-(9H-carbazol-9-yl)-N-4-biphenylaniline (7.80 g, 19.0 mmol), tris(dibenzylideneacetone) dipalladium(0) (166 mg, 0.181 mmol), tri-tert-butylphosphine (73.3 mg, 0.362 mmol), and toluene (120 mL). Sodium tert-butoxide (1.92 g, 19.9 mmol) was then added and the reaction stirred at 80° C. overnight. The solvent was removed and the material was separated by column chromatography using silica gel and 1:3 chloroform in hexanes. Fractions were dried and precipitated from dichloromethane into methanol to give an off-white solid for which 1-H nmr spectroscopy confirms the desired structure.

Synthesis Example 7

This example illustrates the preparation of a compound having Formula III-b, Compound 62.

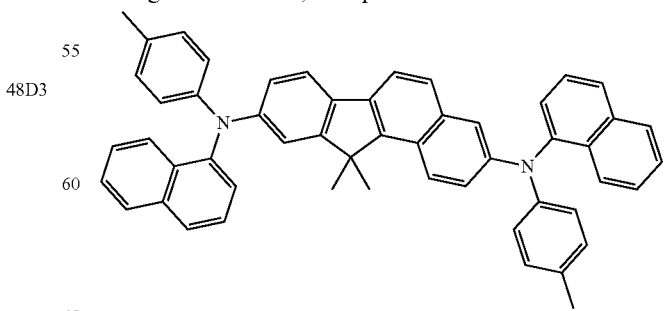

The compound was made using the same procedure as in Synthesis Example 6 above, except that N-(1-naphthyl)-4- methylaniline was used in place of 3-(9H-carbazol-9-yl)-N-4-biphenylaniline. The product was isolated by column chromatography on silica gel eluting with hexanes. 1-H nmr spectroscopy confirmed the expected structure and the material was sublimed in high vacuum for purification.

Synthesis Example 9

This example illustrates a method which could be carried out for the preparation of a compound having Formula II-b, Compound 50.

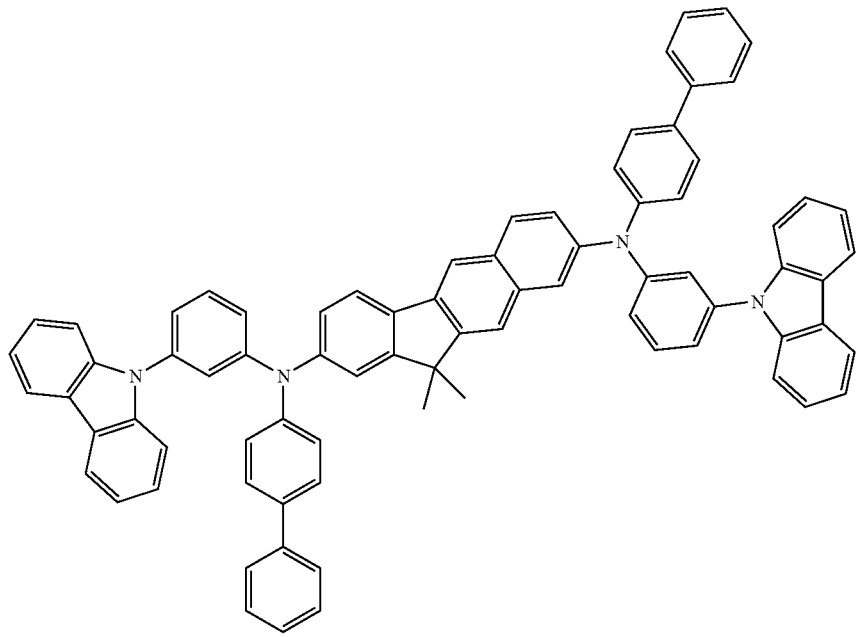

Synthesis Example 8

This example illustrates the preparation of a compound having Formula III-d, Compound 63.

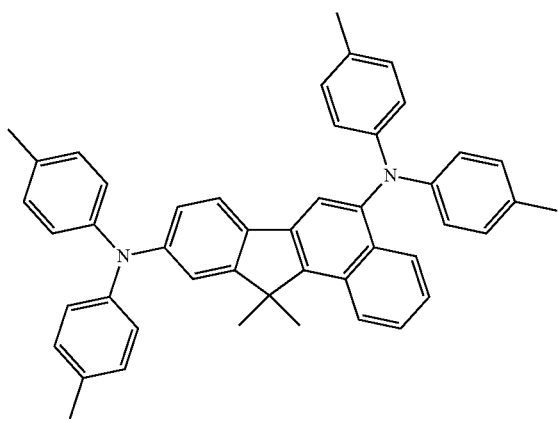

Compound 48D3, described in Synthesis Example 6 above, was isolated by careful chromatography of the mixture (compounds 48D1, 48D2, and 48D3) prepared in Synthesis Example 6, using hexane eluent on a silica gel column. This material was used in place of compound 48D1 in a reaction with the secondary amine bis-4-methylphenylamine, as described in the last step of Synthesis Example 6, to result in Compound 63 instead of Compound 61.

Compound 48D2, described in Synthesis Example 6 above, could be isolated by careful chromatography of the mixture (compounds 48D1, 48D2, and 48D3) prepared in Synthesis Example 6, using hexane eluent on a silica gel column. This material could be used in place of compound 48D1 in a reaction with the secondary amine 3-(9H-carbazol-9-yl)-N-4-biphenylaniline, as described in the last step of Synthesis Example 6.

Device Examples

These examples demonstrate the fabrication and performance of OLED devices.
(1) Materials
HIJ-1 is an electrically conductive polymer doped with a polymeric fluorinated sulfonic acid.
HT-1 is a triarylamine polymer.
HT-2 is a triarylamine polymer.
Host-1 is a deuterated 9,10-diarylanthracene compound.
ET-1 is a fluoranthene derivative.
EIJ-1 is a quinolate compound.
The devices had the following structure on a glass substrate:
  anode=ITO (50 nm)
  hole injection layer=HIJ-1 (100 nm)
  hole transport layer=HT-1 (4 nm)
  hole transport layer=HT-2 (96 nm)
  photoactive layer, discussed below=Host-1:dopant (40 nm), weight ratios given below;
  electron transport layer=ET-1 (20 nm)
  electron injection layer/cathode=EIJ-1/Al (3.5/100 nm)
(2) Device Fabrication
OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 30 ohms/square and 80% light transmission.

The patterned ITO substrates were cleaned and spin-coated with an aqueous dispersion of HIJ-1. The first and second hole transport layers were sequentially formed by spin-coating HT-1 and HT-2, respectively, from solvent solutions. The workpieces were then spin-coated with a solution of the photoactive layer materials in methyl benzoate and heated to remove solvent. The workpieces were masked and placed in a vacuum chamber. A layer of ET-1 was deposited by thermal evaporation, followed by a layer of EIJ-1. Masks were then changed in vacuo and a layer of Al was deposited by thermal evaporation. The chamber was vented, and the devices were encapsulated using a glass lid, desiccant, and UV curable epoxy.

(3) Device Characterization

The OLED samples were characterized by measuring their (1) current-voltage (I-V) curves, (2) electroluminescence luminance versus voltage, and (3) electroluminescence spectra versus voltage. All three measurements were performed at the same time and controlled by a computer. The current efficiency of the device at a certain voltage is determined by dividing the electroluminescence luminance of the LED by the current density needed to run the device. The unit is a cd/A. The color coordinates were determined using either a Minolta CS-100 meter or a Photoresearch PR-705 meter.

Examples 1 and 2

These examples illustrate the use of compounds having Formula I as the light emitting material in a device.

The host:dopant weight ratio was 93:7, by weight.

In Example 1, the dopant was Compound 37.

In Example 2, the dopant was Compound 3.

The results are given in Table 1 below.

TABLE 1

Device results

| Example | Dopant | CE (cd/A) | EQE (%) | Voltage @ 15 mA/cm2 (V) | CIE (x, y) | T70, hrs |
|---|---|---|---|---|---|---|
| 1 | Compound 37 | 4.3 | 5.8 | 4.9 | 0.143 0.080 | 1360 |
| 2 | Compound 3 | 4.5 | 5.8 | 4.9 | 0.144 0.083 | 1280 |

All data @1000 nits. CE is the current efficiency; EQE is the external quantum efficiency; CIE(x,y) are the x and y color coordinates according to the C.I.E. chromaticity scale (Commission Internationale de L'Eclairage, 1931); T70 is the time, in hours, to reach 70% of the initial luminance at 23 mA/cm$^2$ and 50° C.

It can be seen from Table 1 that the devices have good efficiency, low voltage, and lifetime with deep blue color.

Examples 3 and 4

These examples illustrate the use of compounds having Formula I as the light emitting material in a device.

The host:dopant weight ratio was 93:7, by weight.

In Example 3, the dopant was Compound 1.

In Example 4, the dopant was Compound 3.

The results are given in Table 2 below.

TABLE 2

Device results

| Example | Dopant | CE (cd/A) | EQE (%) | Voltage @ 15 mA/cm2 (V) | CIE (x, y) | T70, hrs |
|---|---|---|---|---|---|---|
| 3 | Compound 1 | 4.5 | 5.8 | 4.7 | 0.143 0.084 | 2020 |
| 4 | Compound 3 | 4.1 | 5.5 | 4.6 | 0.145 0.080 | 1350 |

All data @1000 nits. CE is the current efficiency; EQE is the external quantum efficiency; CIE(x,y) are the x and y color coordinates according to the C.I.E. chromaticity scale (Commission Internationale de L'Eclairage, 1931); T70 is the time, in hours, to reach 70% of the initial luminance at 23 mA/cm$^2$ and 50° C.

It can be seen from Table 2 that the devices have good efficiency, low voltage, and lifetime with deep blue color.

Examples 5 and 6

These examples illustrate the use of compounds having Formula I as the light emitting material in a device.

In Example 5, the dopant was Compound 5, with a host:dopant ratio of 93:7, by weight.

In Example 6, the dopant was Compound 5, with a host:dopant ratio of 90:10, by weight.

The results are given in Table 3 below.

TABLE 3

Device results

| Example | Dopant | CE (cd/A) | EQE (%) | Voltage @ 15 mA/cm2 (V) | CIE (x, y) | T70, hrs |
|---|---|---|---|---|---|---|
| 5 | Compound 5 | 4.9 | 6.2 | 4.7 | 0.142 0.086 | 1700 |
| 6 | Compound 5 | 4.8 | 6.0 | 4.7 | 0.143 0.086 | 1700 |

All data @1000 nits. CE is the current efficiency; EQE is the external quantum efficiency; CIE(x,y) are the x and y color coordinates according to the C.I.E. chromaticity scale (Commission Internationale de L'Eclairage, 1931); T70 is the time, in hours, to reach 70% of the initial luminance at 23 mA/cm$^2$ and 50° C.

It can be seen from Table 3 that the devices have good efficiency, low voltage, and lifetime with deep blue color.

Examples 7 and 8

These examples illustrate the use of compounds having Formula I as the light emitting material in a device.

The host:dopant weight ratio was 93:7, by weight.

In Example 7, the dopant was Compound 2.

In Example 8, the dopant was Compound 5.

The results are given in Table 4 below.

TABLE 4

Device results

| Example | Dopant | CE (cd/A) | EQE (%) | Voltage @ 15 mA/cm2 (V) | CIE (x, y) | T70, hrs |
|---|---|---|---|---|---|---|
| 7 | Compound 2 | 4.8 | 6.0 | 5.0 | 0.143 0.085 | 1830 |

TABLE 4-continued

| | | Device results | | | |
|---|---|---|---|---|---|
| Example | Dopant | CE (cd/A) | EQE (%) | Voltage @ 15 mA/cm2 (V) | CIE (x, y) | T70, hrs |
| 8 | Compound 5 | 4.8 | 6.1 | 4.9 | 0.143 0.084 | 1610 |

All data @1000 nits. CE is the current efficiency; EQE is the external quantum efficiency; CIE(x,y) are the x and y color coordinates according to the C.I.E. chromaticity scale (Commission Internationale de L'Eclairage, 1931); T70 is the time, in hours, to reach 70% of the initial luminance at 23 mA/cm$^2$ and 50° C.

It can be seen from Table 4 that the devices have good efficiency, low voltage, and lifetime with deep blue color.

Examples 9-12

These examples illustrate the use of compounds having Formula I as the light emitting material in a device.

The host:dopant weight ratio was 93:7, by weight, for Examples 9-11. The host:dopant weight ratio was 90:10, by weight, for Example 12.

In Example 9, the dopant was Compound 5.
In Example 10, the dopant was Compound 1.
In Examples 11-12, the dopant was Compound 4
The results are given in Table 5 below.

TABLE 5

| | | Device results | | | |
|---|---|---|---|---|---|
| Example | Dopant | CE (cd/A) | EQE (%) | Voltage @ 15 mA/cm2 (V) | CIE (x, y) |
| 9 | Compound 5 | 5.2 | 6.4 | 5.3 | 0.141 0.090 |
| 10 | Compound 1 | 5.0 | 6.2 | 5.0 | 0.141 0.089 |
| 11 | Compound 4 | 5.2 | 6.4 | 5.1 | 0.143 0.088 |
| 12 | Compound 4 | 5.3 | 6.4 | 5.1 | 0.141 0.091 |

All data @1000 nits. CE is the current efficiency; EQE is the external quantum efficiency; CIE(x,y) are the x and y color coordinates according to the C.I.E. chromaticity scale (Commission Internationale de L'Eclairage, 1931.

It can be seen from Table 5 that the devices have good efficiency, low voltage, with deep blue color.

Examples 13-15

These examples illustrate the use of compounds having Formula I as the light emitting material in a device.
The host:dopant ratio is given in Table 6.
The dopant was Compound 2.
The results are given in Table 6 below.

TABLE 6

| | | Device results | | | |
|---|---|---|---|---|---|
| Example | Dopant | Host to Dopant Ratio (weight) | CE (cd/A) | EQE (%) | Voltage @ 15 mA/cm2 (V) | CIE (x, y) |
| 13 | Compound 2 | 93:7 | 4.9 | 6.1 | 5.1 | 0.142 0.087 |
| 14 | Compound 2 | 90:10 | 4.9 | 6.1 | 5.0 | 0.142 0.089 |
| 15 | Compound 2 | 95:5 | 4.9 | 6.1 | 5.1 | 0.142 0.087 |

All data @1000 nits. CE is the current efficiency; EQE is the external quantum efficiency; CIE(x,y) are the x and y color coordinates according to the C.I.E. chromaticity scale (Commission Internationale de L'Eclairage, 1931.

It can be seen from Table 6 that the devices have good efficiency, and low voltage, with deep blue color.

Examples 16 and 17

These examples illustrate the use of compounds having Formula I as the light emitting material in a device.
The host:dopant weight ratio was 93:7.
In Example 16, the dopant was Compound 2.
In Example 17, the dopant was Compound 6.
The results are given in Table 7 below.

TABLE 7

| | | Device results | | | |
|---|---|---|---|---|---|
| Example | Dopant | CE (cd/A) | EQE (%) | Voltage @ 15 mA/cm2 (V) | CIE (x, y) |
| 16 | Compound 2 | 5.3 | 6.3 | 5.1 | 0.140 0.093 |
| 17 | Compound 6 | 4.3 | 5.9 | 5.0 | 0.144 0.077 |

All data @1000 nits. CE is the current efficiency; EQE is the external quantum efficiency; CIE(x,y) are the x and y color coordinates according to the C.I.E. chromaticity scale (Commission Internationale de L'Eclairage, 1931.

It can be seen from Table 7 that the devices have good efficiency, and low voltage, with deep blue color.

In a first embodiment, a compound is provided having Formula I.

In a second embodiment, a compound is provided having Formula I-a.

In a third embodiment, a compound is provided having Formula I-b.

In a fourth embodiment, a compound is provided having Formula I-c.

In a fifth embodiment, a compound is provided having Formula I-d.

In a sixth embodiment, a compound is provided having Formula II.

In a seventh embodiment, a compound is provided having Formula II-a.

In a eighth embodiment, a compound is provided having Formula II-b.

In a ninth embodiment, a compound is provided having Formula II-c.

In a tenth embodiment, a compound is provided having Formula III.

In a eleventh embodiment, a compound is provided having Formula III-a.

In a twelfth embodiment, a compound is provided having Formula III-b.

In a thirteenth embodiment, a compound is provided having Formula III-c.

In a fourteenth embodiment, a compound is provided having Formula III-d.

In a fifteenth embodiment, a compound is provided having Formula III-e.

In a sixteenth embodiment, there is provided a compound according to any one of the first, fourth, fifth, seventh, ninth, eleventh, thirteenth or fifteenth embodiments wherein at least one $R^1$ and $R^{1a}$ is selected from the group consisting of pyrrole, pyridine, pyrimidine, carbazole, imidazole, benzimidazole, imidazolobenzimidazole, triazole, benzotriazole, triazolopyridine, thiophene, benzothiophene, dibenzothiophene, furan, benzofuran, dibenzofuran, oxazole, benzoxazole, thiazole, benzothiazole, substituted derivatives thereof, and deuterated analogs thereof.

In a seventeenth embodiment, there is provided a compound according to the sixteenth embodiment wherein the carbazole is selected from the group consisting of Cz-1, Cz-2, Cz-3, and deuterated analogs thereof.

In an eighteenth embodiment, there is provided a compound according to the sixteenth embodiment wherein the dibenzothiophene is selected from the group consisting of DBT-1, DBT-2, and deuterated analogs thereof.

In a nineteenth embodiment, there is provided a compound according to the sixteenth embodiment wherein the dibenzofuran is selected from the group consisting of DBF-1, DBF-2, and deuterated analogs thereof.

In a twentieth embodiment, there is provided a compound according to any one of the first, fourth, fifth, seventh, ninth, eleventh, thirteenth or fifteenth through nineteenth embodiments wherein one of $R^2$ and $R^{2a}$ is alkyl or deuterated alkyl, and the other of $R^2$ and $R^{2a}$ is H or D.

In a twenty-first embodiment, there is provided a compound according to any one of the second, third, fourth, fifth, or fifteenth through twentieth embodiments wherein at least one $R^{2b}$ is H or D.

In a twenty-second embodiment, there is provided a compound according to any one of the first, fourth, fifth, seventh, ninth, eleventh, thirteenth or fifteenth through twenty-first embodiments wherein at least one $R^3$ is present and is selected from the group consisting of phenyl, naphthyl, anthracenyl, combinations of such groups linked together covalently, and deuterated analogs thereof, where the groups may be further substituted with alkyl or deuterated alkyl groups.

In a twenty-third embodiment, there is provided a compound according to any one of the first, fourth, fifth, seventh, ninth, eleventh, thirteenth or fifteenth through twenty-second embodiments wherein at least one $R^{3a}$ is present and is selected from the group consisting of phenyl, naphthyl, anthracenyl, combinations of such groups linked together covalently, and deuterated analogs thereof, where the groups may be further substituted with alkyl or deuterated alkyl groups.

In a twenty-fourth embodiment, there is provided a compound according any one of the first, fourth, fifth, seventh, ninth, eleventh, thirteenth or fifteenth through twenty-third embodiments wherein at least one $R^4$ is present and is selected from the group consisting of alkyl and deuterated alkyl having 1-12 carbons; in some embodiments, 3-8 carbons; in some embodiments 1-4 carbons.

In a twenty-fifth embodiment, there is provided a compound according any one of the first, fourth, fifth, seventh, ninth, eleventh, thirteenth or fifteenth through twenty-fourth embodiments wherein at least one $R^{4a}$ is present and is selected from the group consisting of alkyl and deuterated alkyl having 1-12 carbons; in some embodiments, 3-8 carbons; in some embodiments 1-4 carbons.

In a twenty-sixth embodiment, there is provided a compound according to any one of the second, third, sixth, eighth, tenth, twelfth or fourteenth embodiments wherein at least one $R^{10}$ group is present and is selected from the group consisting of phenyl, naphthyl, anthracenyl, combinations of such groups linked together covalently, and deuterated analogs thereof, where the groups may be further substituted with alkyl or deuterated alkyl groups.

In a twenty-seventh embodiment, there is provided a compound according to any one of the first through twenty-sixth embodiments wherein $R^5$ is H or D.

In a twenty-eighth embodiment, there is provided a compound according to any one of the first through twenty-seven embodiments wherein $R^6$ is H or D.

In a twenty-ninth embodiment, there is provided a compound according to any one of the first through twenty-eight embodiments wherein $R^7$ is selected from the group consisting of alkyl and deuterated alkyl having 1-12 carbons.

In a thirtieth embodiment, there is provided a compound according to any one of the first through twenty-nine embodiments wherein a=b=1.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A compound having Formula I, Formula I-a, Formula I-b, Formula I-c, Formula I-d, Formula II-a, Formula II-c, Formula III, Formula III-a, Formula III-b, Formula III-c, Formula III-d, or Formula III-e:

(I)
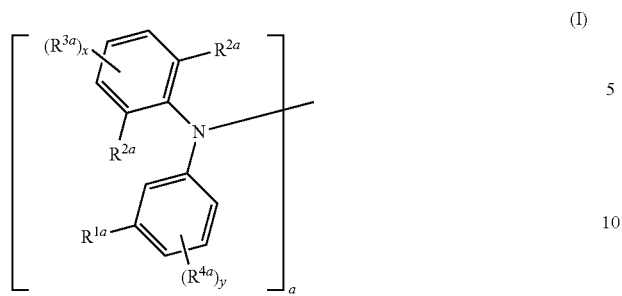
(I-a)
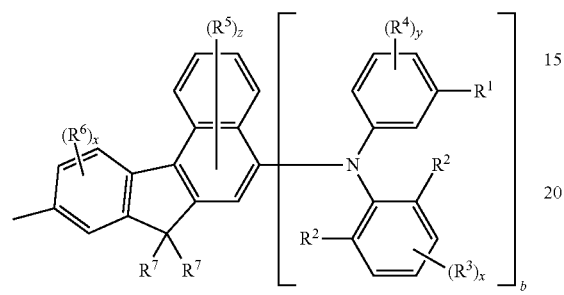
(I-b)
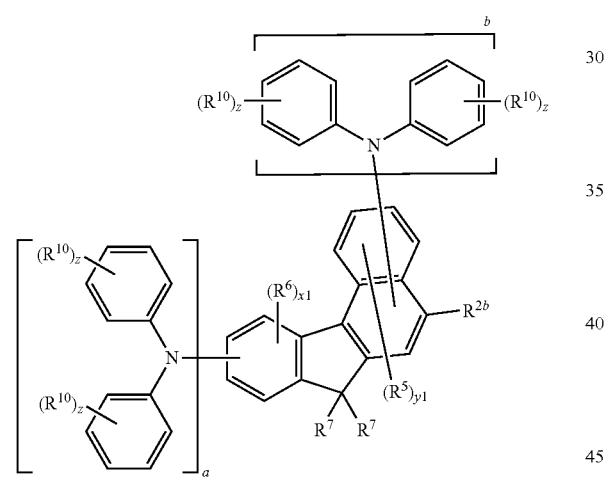
(I-c)
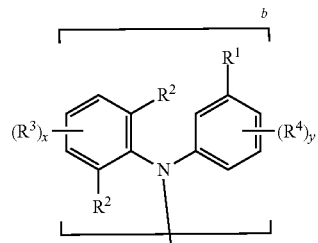
(I-d)
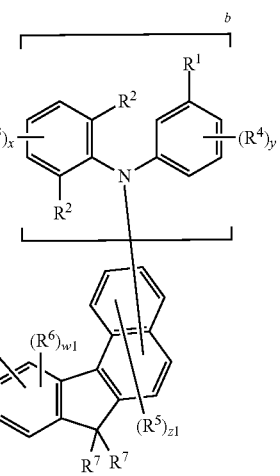
(II-a)
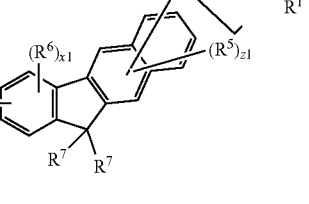

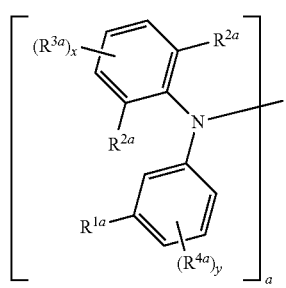
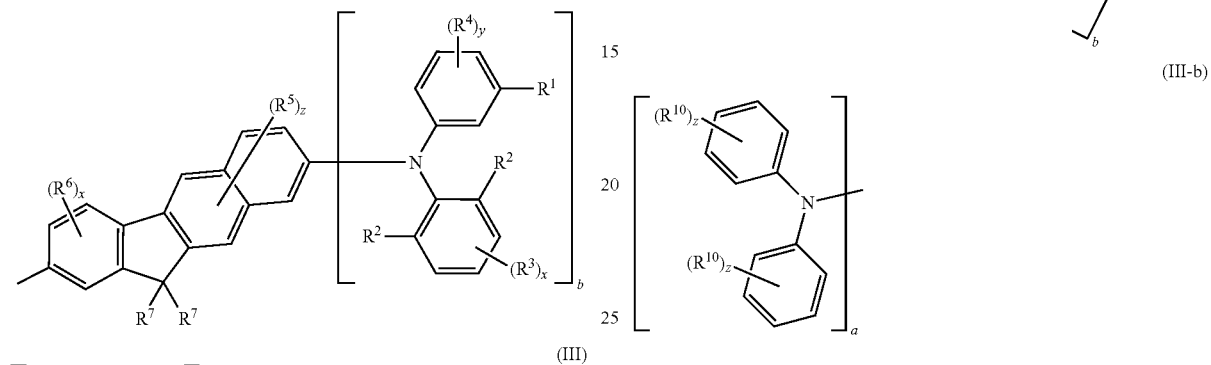
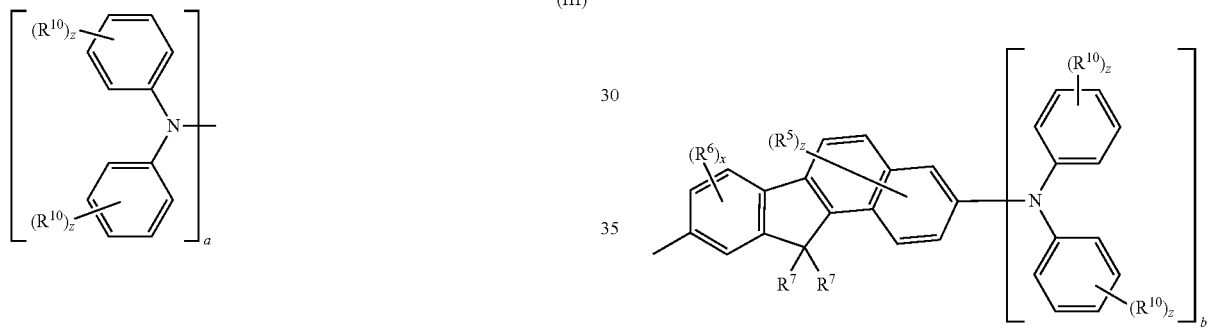
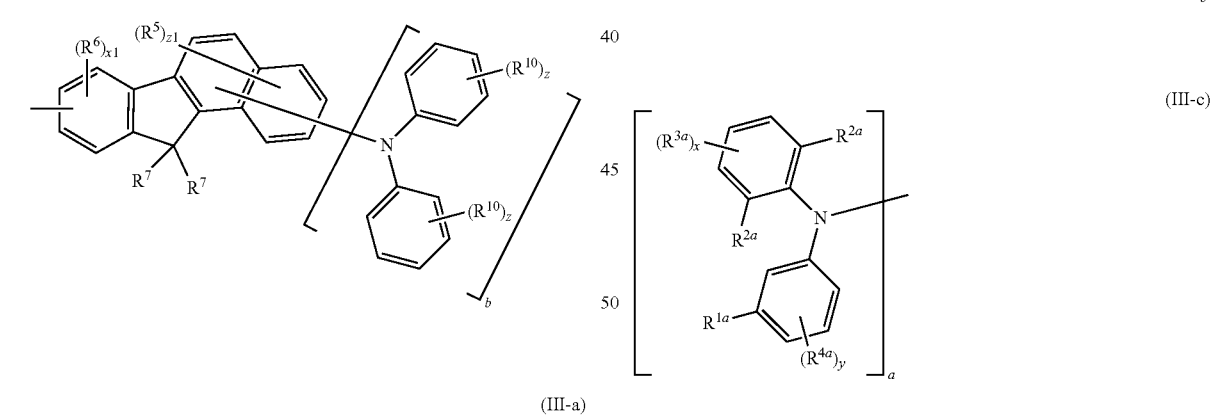
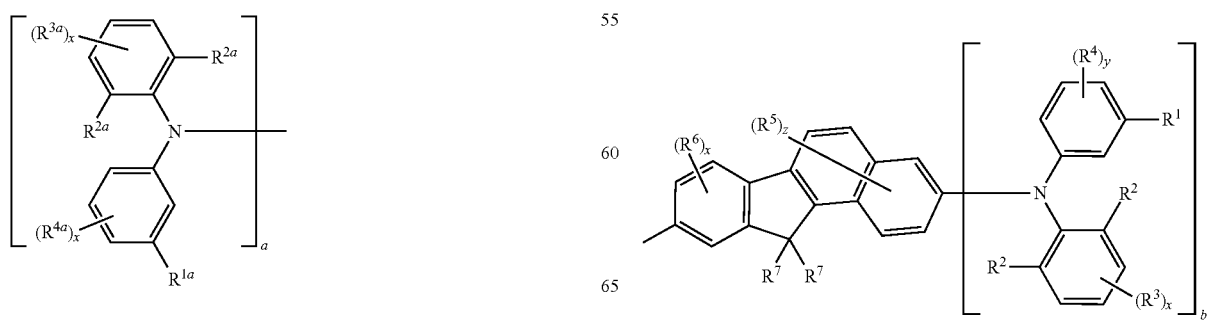

-continued

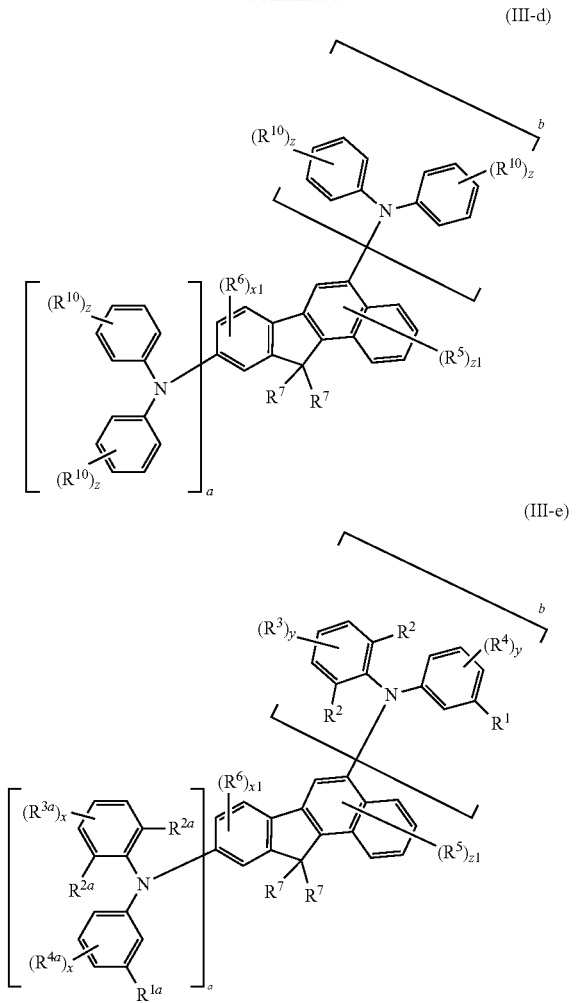

wherein:
$R^1$, $R^{1a}$, $R^2$, $R^{2a}$ and $R^{2b}$ are the same or different at each occurrence and are selected from the group consisting of H, D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, with the proviso that at least one of $R^1$ and $R^{1a}$ is heteroaryl or deuterated heteroaryl;

$R^3$, $R^{3a}$, $R^4$, $R^{4a}$, $R^5$, and $R^6$ are the same or different at each occurrence and are selected from the group consisting of D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, wherein adjacent groups selected from $R^3$, $R^{3a}$, $R^4$, and $R^{4a}$ can be joined together to form a fused ring;

$R^7$ is the same or different at each occurrence and is selected from the group consisting of alkyl, aryl, and deuterated analogs thereof, where two alkyl $R^7$ groups can be joined together to make a cycloalkyl spiro ring, and where two $R^7$ phenyl groups can be joined to form a spiro fluorene group;

$R^{10}$ is the same or different at each occurrence and is selected from the group consisting of D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, where adjacent $R^{10}$ groups can be joined together to form a fused ring;

a and b are the same or different and are 0 or 1, with the proviso that a+b≥1;
w1 is an integer of 0-3, with the proviso that when a=1, w1 is 0-2;
x is an integer of 0-3;
x1 is an integer of 0-4, with the proviso that when a=1, x1 is 0-3;
y is an integer of 0-4;
y1 is an integer of 0-5, with the proviso that when b=1, y1 is 0-4;
z is an integer of 0-5; and
z1 is an integer of 0-6, with the proviso that when b=1, z1 is 0-5.

2. The compound of claim 1 having Formula I.
3. The compound of claim 1 having Formula I-a.
4. The compound of claim 1 having Formula I-b.
5. The compound of claim 1, having Formula I-c.
6. The compound of claim 1, having Formula I-d.
7. The compound of claim 1 having Formula II-a.
8. The compound of claim 1 having Formula II-c.
9. The compound of claim 1 having Formula III.
10. The compound of claim 1 having Formula III-a.
11. The compound of claim 1 having Formula III-b.
12. The compound of claim 1 having Formula III-c.
13. The compound of claim 1 having Formula III-d.
14. The compound of claim 1 having Formula III-e.
15. The compound of claim 1, wherein at least one $R^1$ and $R^{1a}$ is selected from the group consisting of pyrrole, pyridine, pyrimidine, carbazole, imidazole, benzimidazole, imidazolobenzimidazole, triazole, benzotriazole, triazolopyridine, thiophene, benzothiophene, dibenzothiophene, furan, benzofuran, dibenzofuran, oxazole, benzoxazole, thiazole, benzothiazole, substituted derivatives thereof, and deuterated analogs thereof.
16. The compound of claim 15, wherein the carbazole is selected from the group consisting of Cz-1, Cz-2, Cz-3, and deuterated analogs thereof

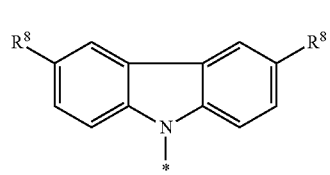

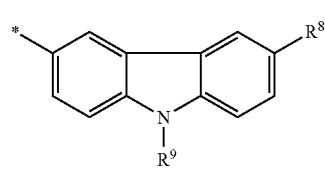

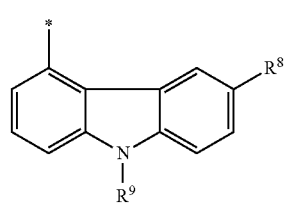

wherein:
R[8] is the same or different at each occurrence and is selected from the group consisting of alkyl, silyl, aryl, and deuterated analogs thereof;
R[9] is selected from the group consisting of aryl and deuterated aryl; and
* represents the point of attachment.

17. The compound of claim 15, wherein the dibenzothiophene is selected from the group consisting of DBT-1, DBT-2, and deuterated analogs thereof

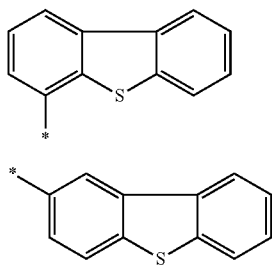

DBT-1

DBT-2 wherein:
* represents the point of attachment.

18. The compound of claim 15, wherein the dibenzofuran is selected from the group consisting of DBF-1, DBF-2, and deuterated analogs thereof

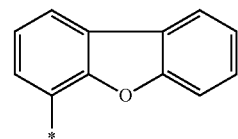

DBF-1

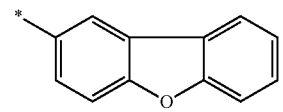

DBF-2 wherein:
* represents the point of attachment.

19. An electronic device comprising at least one photoactive layer, wherein the photoactive layer comprises a compound having Formula I, Formula I-a, Formula I-b, Formula I-c, Formula I-d, Formula II-a, Formula II-c, Formula III, Formula III-a, Formula III-b, Formula III-c, Formula III-d, or Formula III-e:

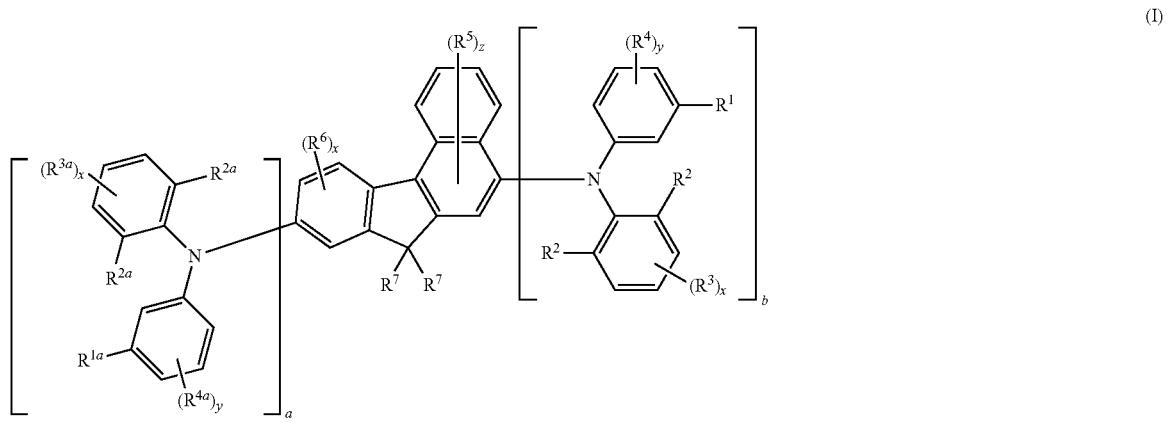

(I)

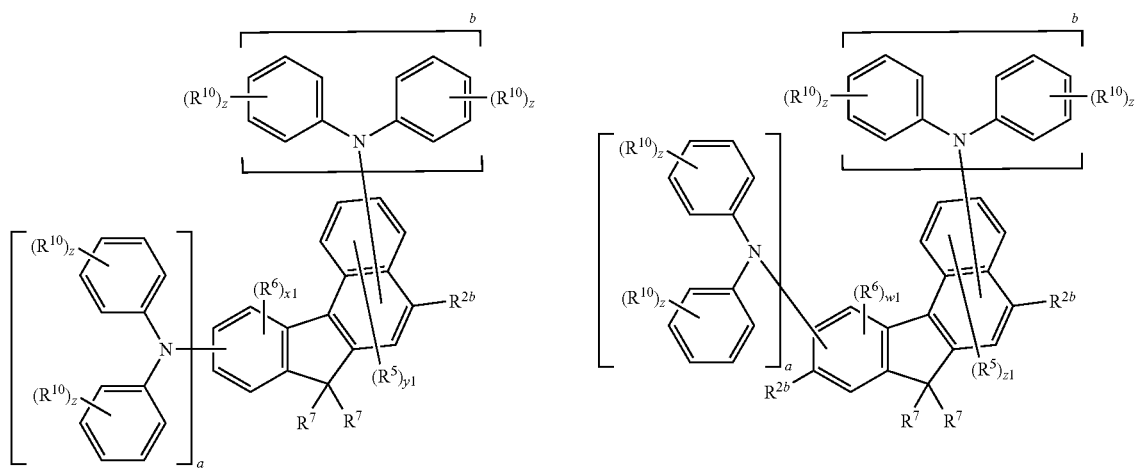

(I-a)         (I-b)

-continued
(I-c)
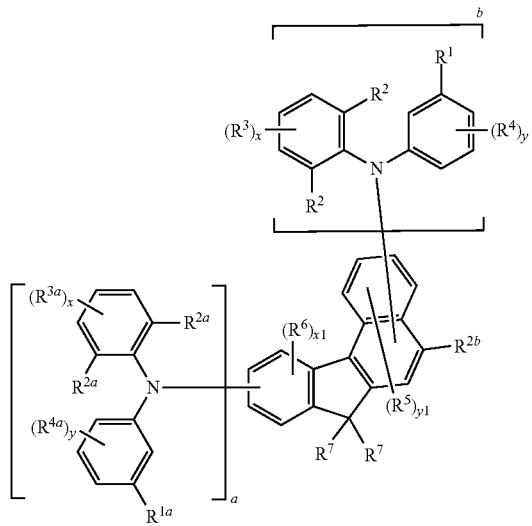
(I-d)
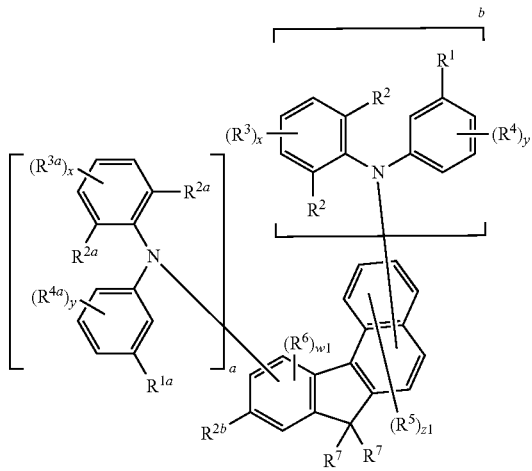
(II-a)
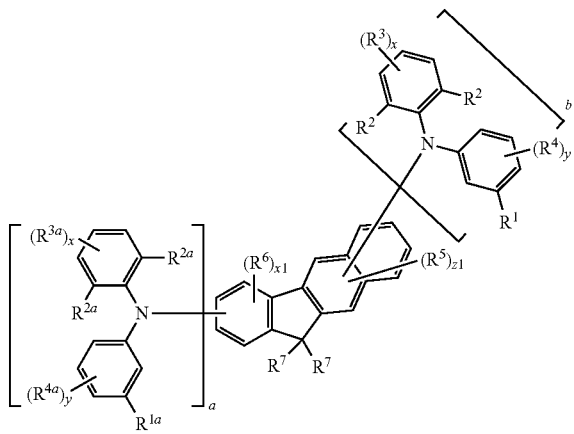
(II-c)
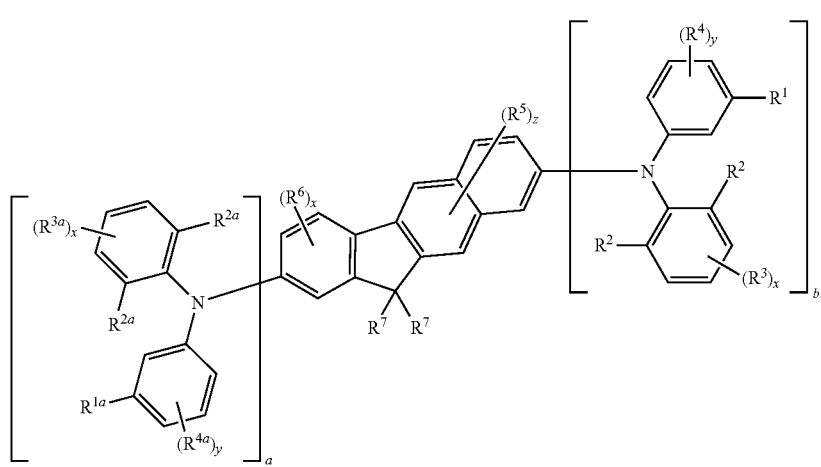

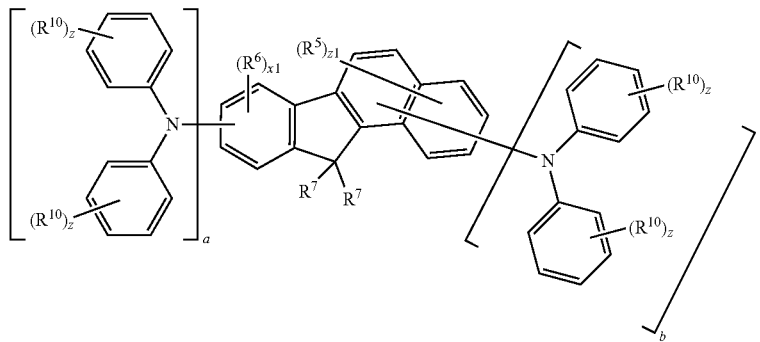
(III)
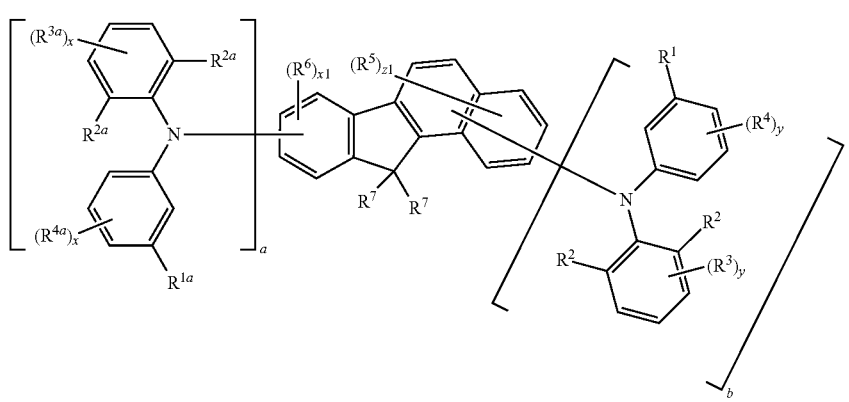
(III-a)
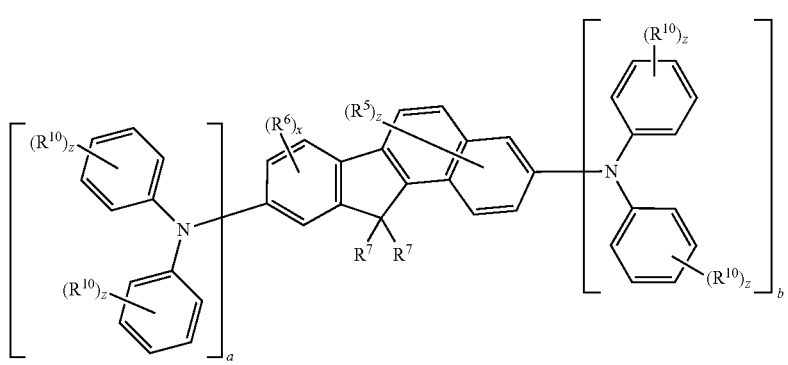
(III-b)
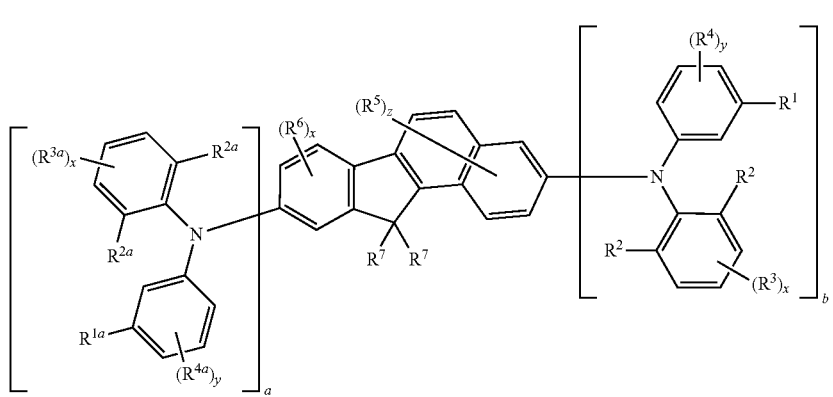
(III-c)

-continued (III-d)

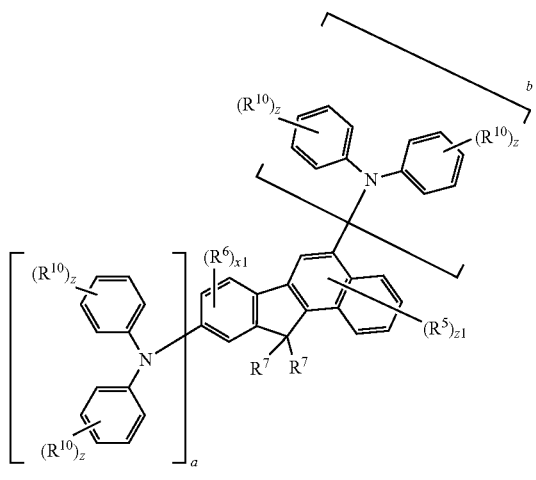

(III-e)

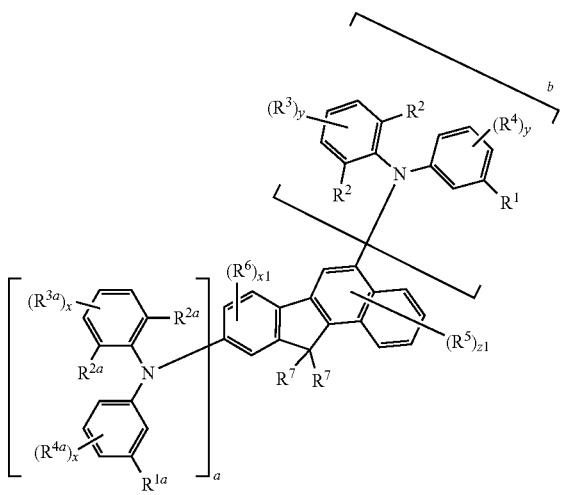

wherein:
$R^1$, $R^{1a}$, $R^2$, $R^{2a}$ and $R^{2b}$ are the same or different at each occurrence and are selected from the group consisting of H, D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, with the proviso that at least one of $R^1$ and $R^{1a}$ is heteroaryl or deuterated heteroaryl;
$R^3$, $R^{3a}$, $R^4$, $R^{4a}$, $R^5$, and $R^6$ are the same or different at each occurrence and are selected from the group consisting of D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, wherein adjacent groups selected from $R^3$, $R^{3a}$, $R^4$, and $R^{4a}$ can be joined together to form a fused ring;
$R^7$ is the same or different at each occurrence and is selected from the group consisting of alkyl, aryl, and deuterated analogs thereof, where two alkyl $R^7$ groups can be joined together to make a cycloalkyl spiro ring, and where two $R^7$ phenyl groups can be joined to form a spiro fluorene group;
$R^{10}$ is the same or different at each occurrence and is selected from the group consisting of D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy, where adjacent $R^{10}$ groups can be joined together to form a fused ring;
a and b are the same or different and are 0 or 1, with the proviso that a+b≥1;
w1 is an integer of 0-3, with the proviso that when a=1, w1 is 0-2;
x is an integer of 0-3;
x1 is an integer of 0-4, with the proviso that when a=1, x1 is 0-3;
y is an integer of 0-4;
y1 is an integer of 0-5, with the proviso that when b=1, y1 is 0-4;
z is an integer of 0-5; and
z1 is an integer of 0-6, with the proviso that when b=1, z1 is 0-5.

20. A compound having Formula II or Formula II-b:

(II)

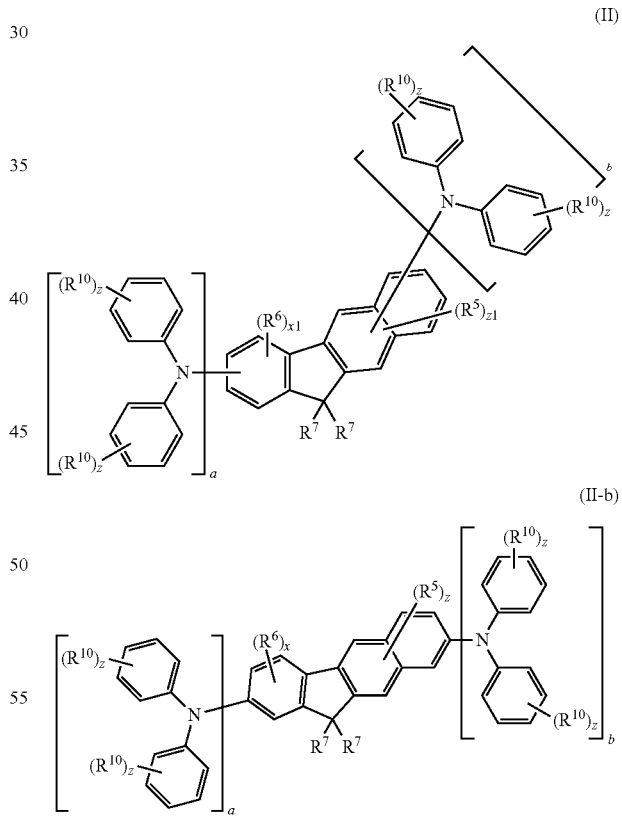

(II-b)

wherein:
$R^5$ and $R^6$ are the same or different at each occurrence and are selected from the group consisting of D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy;

$R^7$ is the same or different at each occurrence and is selected from the group consisting of alkyl, aryl, and deuterated analogs thereof, where two alkyl $R^7$ groups can be joined together to make a cycloalkyl spiro ring, and where two $R^7$ phenyl groups can be joined to form a spiro fluorene group;

$R^{10}$ is the same or different at each occurrence and is selected from the group consisting of D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy;

a and b are the same or different and are 0 or 1, with the proviso that a+b≥1;

x is an integer of 0-3;
x1 is an integer of 0-4;
z is an integer of 0-5; and
z1 is an integer of 0-6.

21. An electronic device comprising at least one photoactive layer, wherein the photoactive layer comprises a compound having Formula II or Formula II-b:

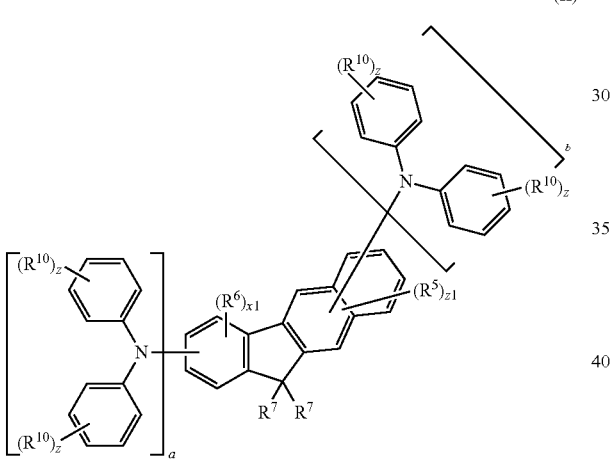

(II)

-continued

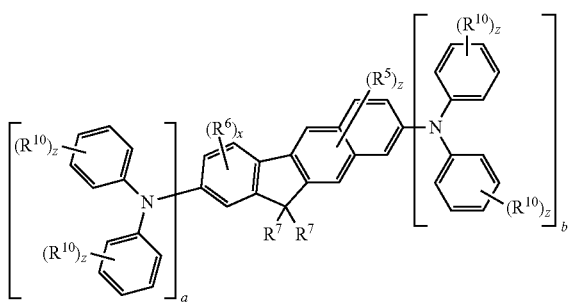

(II-b)

wherein:

$R^5$ and $R^6$ are the same or different at each occurrence and are selected from the group consisting of D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy;

$R^7$ is the same or different at each occurrence and is selected from the group consisting of alkyl, aryl, and deuterated analogs thereof, where two alkyl $R^7$ groups can be joined together to make a cycloalkyl spiro ring, and where two $R^7$ phenyl groups can be joined to form a spiro fluorene group;

$R^{10}$ is the same or different at each occurrence and is selected from the group consisting of D, F, CN, alkyl, fluoroalkyl, aryl, heteroaryl, silyl, deuterated alkyl, deuterated partially-fluorinated alkyl, deuterated aryl, deuterated heteroaryl, deuterated silyl, alkoxy, aryloxy, fluoroalkoxy, siloxane, siloxy, deuteroalkoxy, deuteroaryloxy, deuterofluoroalkoxy, deuterosiloxane, and deuterosiloxy;

a and b are the same or different and are 0 or 1, with the proviso that a+b≥1, x is an integer of 0-3;
x1 is an integer of 0-4;
z is an integer of 0-5; and
z1 is an integer of 0-6.

* * * * *